US012590309B2

(12) United States Patent
Peng et al.

(10) Patent No.: US 12,590,309 B2
(45) Date of Patent: Mar. 31, 2026

(54) REPROGRAMMING OF LIPID METABOLISM TO INHIBIT T CELL SENESCENCE AND ENHANCE TUMOR IMMUNOTHERAPY

(71) Applicant: Saint Louis University, St. Louis, MO (US)

(72) Inventors: Guangyong Peng, St. Louis, MO (US); Xia Liu, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 1121 days.

(21) Appl. No.: 17/613,130

(22) PCT Filed: May 19, 2020

(86) PCT No.: PCT/US2020/033530
§ 371 (c)(1),
(2) Date: Nov. 22, 2021

(87) PCT Pub. No.: WO2020/236777
PCT Pub. Date: Nov. 26, 2020

(65) Prior Publication Data
US 2022/0220482 A1    Jul. 14, 2022

Related U.S. Application Data

(60) Provisional application No. 62/850,258, filed on May 20, 2019.

(51) Int. Cl.
| | |
|---|---|
| *A61K 40/11* | (2025.01) |
| *A61K 31/7088* | (2006.01) |
| *A61K 40/42* | (2025.01) |
| *A61P 35/00* | (2006.01) |
| *C12N 5/0783* | (2010.01) |
| *C12N 15/113* | (2010.01) |
| *G01N 33/50* | (2006.01) |
| *G01N 33/573* | (2006.01) |
| *C12N 9/18* | (2006.01) |
| *C12Q 1/44* | (2006.01) |

(52) U.S. Cl.
CPC ...... *C12N 15/1137* (2013.01); *A61K 31/7088* (2013.01); *A61K 40/11* (2025.01); *A61K 40/4271* (2025.01); *A61K 40/4273* (2025.01); *A61P 35/00* (2018.01); *C12N 5/0637* (2013.01); *G01N 33/5011* (2013.01); *G01N 33/505* (2013.01); *G01N 33/573* (2013.01); *A61K 2239/31* (2023.05); *A61K 2239/57* (2023.05); *G01N 2333/916* (2013.01)

(58) Field of Classification Search
CPC .......... C12N 2501/00; C12N 2501/999; C12N 5/0637
See application file for complete search history.

(56) References Cited

U.S. PATENT DOCUMENTS

2007/0004719 A1    1/2007  McKew et al.

FOREIGN PATENT DOCUMENTS

| WO | WO 2018/187698 | 10/2018 |
| WO | WO 2019/006427 | 1/2019 |

OTHER PUBLICATIONS

Liu et al., (2021) Reprogramming lipid metabolism prevents effector T cell senescence and enhances tumor immunotherapy. Sci. Transl. Med., 13: https://doi.org/10.1016/j.ijbiomac.2025.141573 (Year: 2021).*
Liu et al., (2018) Regulatory T cells trigger effector T cell DNA damage and senescence caused by metabolic competition. Nat Commun., 9: 249 (Year: 2018).*
Liu et al., (2021) Reprogramming lipid metabolism prevents effector T cell senescence and enhances tumor immunotherapy. Science Translational Medicine, 13(587): eaaz6314 (Year: 2021).*
Tessier et al., (2002) Implication of three isoforms of PLA2 in human T-cell proliferation. FEBS Letters, 520(1-3): pp. 111-116 (Year: 2002).*
Berod, et al. "De novo fatty acid synthesis controls the fate between regulatory T and T helper 17 cells", *Nature medicine* 20, 1327-1333, 2014.
Buck, et al. "Mitochondrial Dynamics Controls T Cell Fate through Metabolic Programming". *Cell* 166, 63-76, 2016.
Chuang et al., "Cytosolic phospholipase A2 plays a crucial role in ROS/NO signaling during microglial activation through the lipoxygenase pathway", *Journal of Neuroinflammation*, 12:199, 2015.
Feuerherm et al., "Cytosolic group IVA phospholipase A2 inhibitors, AVX001 and AVX002, ameliorate collagen-induced arthritis", *Arthritis Research & Therapy*, 21(29):1-13, 2019.
Ford, "Saturated fatty acid metabolism is key link between cell division, cancer, and senescence in cellular and whole organism aging", *Age (Dordr)* 32, 231-237, 2010.
Fujimoto, "Not just fat: the structure and function of the lipid droplet", *Cold Spring Harbor perspectives in biology* 3, 2011.
Gubern, et al. "Group IVA phospholipase A2 is necessary for the biogenesis of lipid droplets", *J Biol Chem* 283, 27369-27382, 2008.
International Search Report and Written Opinion for PCT/US2020/033530 dated Aug. 28, 2020 (16 pages).
Kalyvas et al., "Cytosolic Phospholipase A2 Plays a Key Role in the Pathogenesis of Multiple Sclerosis-like Disease", 4, pp. 323-333, 2004.
Linkous et al., "Cytosolic Phospholipase A2 and Lysophospholipids in Tumor Angiogenesis", *J. Nat'l Cancer Inst.*, 102(18):1398-412, 2010.

(Continued)

*Primary Examiner* — Kara D Johnson
(74) *Attorney, Agent, or Firm* — pH IP Law

(57) ABSTRACT

The present disclosure provides compositions and methods for inhibiting T cell senescence and improving T cell immunotherapies. In particular, inhibitors of group IV A phospholipase A2 are disclosed as useful in modulating the lipid metabolism of cells, in particular effector T cells, such that T reg- and tumor cell-induced cell senescence is abrogated. These methods may be employed with particular utility in adoptive T cell therapies and/or enhanced T cell effector functions in vivo, including those performed in combination with checkpoint blockade therapies.

13 Claims, 22 Drawing Sheets

Specification includes a Sequence Listing.

(56)                    References Cited

OTHER PUBLICATIONS

Liu et al., "Regulatory T cells trigger effector T cell DNA damage and senescence caused by metabolic competition" *Nature Communications*, 9(249):1-16, 2018.

Malda-Edelstein et al., "Regulatory role of cytosolic phospholipase A2 alpha in the induction of CD40 in microglia", *Journal of Neuroinflammation*, 14(1):33, 2017.

Michalek, et al. Cutting edge: distinct glycolytic and lipid oxidative metabolic programs are essential for effector and regulatory CD4+ T cell subsets. *J Immunol* 186, 3299-3303, 2011.

NCBI, "PLA2G4A phospholipase A2 group IVA [*Homo sapiens* (human)]", Gene ID: 5321, pp. 1-12, Nov. 3, 2016.

Patel et al., Cytosolic Phospholipase A2-α: A Potential Therapeutic Target for Prostate Cancer, *Clin Cancer Res*, 14(24):8070-8079, 2008.

Pearce, E. L. et al. Enhancing CD8 T-cell memory by modulating fatty acid metabolism. *Nature* 460, 103-107, 2009.

Peng, et al. "Toll-like receptor 8-mediated reversal of CD4+ regulatory T cell function", *Science* 309, 1380-1384, 2005.

Peng, et al. "Tumor-infiltrating gamma-delta T cells suppress T and dendritic cell function via mechanisms controlled by a unique toll-like receptor signaling pathway", *Immunity* 27, 334-348, 2007.

Penno, "Phospholipids and lipid droplets", *Biochimica et biophysica acta* 1831, 589-594, 2013.

Sharma, "Immune checkpoint targeting in cancer therapy: toward combination strategies with curative potential", *Cell* 161, 205-214, 2015.

Shi, et al. "HIF1alpha-dependent glycolytic pathway orchestrates a metabolic checkpoint for the differentiation of TH17 and Treg cells", *The Journal of experimental medicine* 208, 1367-1376, 2011.

Thotala et al., "Cytosolic PhospholipaseA2 Inhibition with PLA-695 Radiosensitizes Tumors in Lung Cancer Animal Models" *PLoS*, 8(7):e69688, 2013.

Topalian, "Immune checkpoint blockade: a common denominator approach to cancer therapy", *Cancer Cell* 27, 450-461, 2015.

Yang et al. "Potentiating the antitumour response of CD8(+) T cells by modulating cholesterol metabolism." *Nature*, 531, 651-655, 2016.

Yang, "Protective Effect of Cytosolic Phospholipase A2 Inhibition against Inflammation and Degeneration by Promoting Regulatory T Cells in Rats with Experimental Autoimmune Encephalomyelitis", *Mediators of Inflammation*, 2014(890139):1-17, 2014.

Ye & Peng, "Controlling T cell senescence in the tumor microenvironment for tumor immunotherapy", *Oncoimmunology* 4, e994398, 2015.

Ye, J. et al. Human regulatory T cells induce T-lymphocyte senescence. Blood 120, 2021-2031, doi:blood-2012-03-416040 [pii] 10.1182/blood-2012-03-416040 (2012).

Ye, J. et al. TLR8 signaling enhances tumor immunity by preventing tumor-induced T-cell senescence. *EMBO molecular medicine* 6, 1294-1311, 2014.

Ye, J. et al. Tumor-derived gammadelta regulatory T cells suppress innate and adaptive immunity through the induction of immunosenescence. *Journal of immunology* 190, 2403-2414,2013/.

Zou, "PD-L1 (B7-H1) and PD-1 pathway blockade for cancer therapy: Mechanisms, response biomarkers, and combinations", *Science translational medicine* 8, 328rv324, 2016.

* cited by examiner

REPROGRAMMING OF LIPID METABOLISM TO INHIBIT T CELL SENESCENCE AND ENHANCE TUMOR IMMUNOTHERAPY

PRIORITY CLAIM

This application is a national phase application under 35 U.S.C. § 371 of International Application No. PCT/US2020/033530, filed May 19, 2020, which claims benefit of priority to U.S. Provisional Application Ser. No. 62/850,258, filed May 20, 2019, the entire contents of each of which are hereby incorporated by reference.

FEDERAL FUNDING SUPPORT CLAUSE

This invention was made with government support under grant numbers CA184379, CA242188, CA237149, AG078822 and AG067441 awarded by the National Institutes of Health/National Cancer Institute/National Institute on Aging. The government has certain rights in the invention.

FIELD OF THE DISCLOSURE

The present disclosure relates to the fields of medicine, oncology, cellular biochemistry, immunology and molecular biology. In particular, the disclosure relates to the use of inhibitors of group IVA phosopholipase $A_2$ for the enhancing immune response and treating cancer in a subject in need thereof.

BACKGROUND

Immunotherapies, including immune checkpoint blockage therapy and adoptive T cell therapy, have resulted in promising results in certain types of cancer patients, but the overall effective rates are still varied among the tumor types (Topalian et al., 2015; Sharm and Allison, 2015; Rosenberg and Restifo, 2015). One of the key determinants for the therapeutic efficacy and immune responses is functional state of the transferred/preexisting T cells in the suppressive tumor microenvironment (Thommen and Schumacher, 2018; Zou et al., 2016). It is now well-recognized that T cells are exhausted with expression of inhibitory receptors in the tumor microenvironment in cancer patients, which is also accompanied with the loss of effector functions and proliferation (Thomman and Schumacher, 2018; Baitsch et al., 2011; Fourcade et al., 2010). However, the current checkpoint blockage therapy using antibodies to target PD1/PDL1 or/and CTLA4 only have limited success rates from 15% to 35%, further suggesting that there are other mechanisms and/or checkpoint signaling involved in T cell dysfunction mediated by malignant tumors (Topalian et al., 2015; Sharm and Allison, 2015; Zou et al., 2016). A better understanding of the distinct mechanisms responsible for T cell dysfunctional states within the tumor suppressive microenvironment should provide novel avenues for tumor immunotherapy.

Cellular energy metabolism directs T cell survival, proliferation and their specific functions (Macintyre et al., 2014; Pearce, 2010; Zeng and Chi, 2015; McIver et al., 2013). Aerobic glycolysis is the main metabolic pathway and is specifically required for T cell effector function upon activation (Macintyre et al., 2014; McIver et al., 2013; Michalek et al., 2011; Chang et al., 2013; 2015). Furthermore, different T cell subsets have different metabolic profiles (Pearce, 2010; Zeng and Chi, 2015; McIver et al., 2013). Activated CD4+ T cells increase both glycolysis and fatty acid metabolism; while CD8+ T cells dominantly shift metabolism to glycolysis to rapidly produce ATP (Sinclair et al., 2013; Angela et al., 2016). Increasing evidence suggests that malignant tumors rewrite T cell metabolic programs and functions, sustaining a tumor suppressive microenvironment (Thommen and Schumacher, 2018; Huang et al., 2018; Zhang and Romero, 2018; Kouidhi et al., 2017). Tumor cells and tumor-infiltrating T cells (TILs) directly compete for key nutrients, such as glucose and glutamine within the tumor suppressive microenvironment, which impair T cell metabolism and effector functions, and drive tumor suppression and progression (Chang et al., 2015; Kouidhi et al., 2017; Sukumar et al., 2015; Beckermann et al., 2017; Zhao et al., 2016). Furthermore, tumor-derived Treg cells also mediate acceleration of glucose consumption and trigger cell senescence and DNA damage in responder T cells during their cross-talk (Liu et al., 2018; Ye et al., 2014). In addition, tumor cells highly expressing checkpoint molecules PD-1 and CTLA4 alter T cell metabolic program via inhibiting Glut1 and glycolysis, as well as enhance lipid oxidation (Patsoukis et al., 2015; Bengsch et al., 2016). The tumor microenvironment also decreases PPAR-γ coactivator 1α (PGC1α) and mitochondrial biogenesis and function in TILs (Scharping et al., 2016). Although these more recent studies have progressed for improved understanding of reprogramming of glucose metabolism in T cells within the tumor microenvironment, the active metabolic pathways and regulations in lipid metabolism in TILs modulated by malignant tumors are still unclear. Actually, lipids are not only structural molecules, but also play important roles in regulating fundamental cellular processes, including different cell fates of cell death and division (Antilla-Gokcumen et al., 2014; Magatanong et al., 2016). Recent studies suggested that tumor-derived DCs with tolerogenic functions have inhibited glycolysis but with a promoted lipid droplet (LD) accumulation, resulting in impaired antigen-presenting functions and T cell priming (Ramakrishnan et al., 2014; Herber et al., 2010). However, whether and how rewriting lipid metabolism happens in T cells within the tumor microenvironment are unknown. Comprehensively exploring the metabolic profiles of T cells and the causative molecular interactions within the tumor suppressive microenvironment will facilitate the development of novel strategies for cancer therapy via metabolic reprogramming of cell fate and functions.

In addition to exhaustion, immunosenescence is another state of T cell dysfunction within the tumor microenvironment, which is a key strategy utilized by malignant tumors to evade immune surveillance (Ye et al., 2014; 2012; 2013; Ye and Peng; 2015). Senescent T cells exhibit dysfunctional anti-tumor activity but are not functionally exhausted nor anergic (Liu et al., 2018). Significant accumulation of senescent CD8+ T cells has been found in TILs from various types of cancer patients, including lung, colorectal, ovarian, and breast cancers (Meloni et al., 2006; Gruber et al., 2008; Urbaniak-Kujda et al. 2009). Furthermore, multiple types of tumor cells can directly induce T cell senescence via tumor-derived metabolite cAMP (Ye et al., 2014; 2015). In addition, tumor-derived Treg cells can induce cell senescence in responder effector T cells (Liu et al., 2018; Ye et al., 2012; 2013). These studies provide important mechanisms responsible for the accumulation of senescent T cells in cancer patients. However, the metabolic signature of senescent T cells in the tumor microenvironment is unknown, although studies from other types of senescent cells have demonstrated that senescent cells have permanent cell cycle arrest but exhibit active metabolism with elevated glycolysis during senescence (James et al., 2015; Liao et al., 2014; Takebayashi et al., 2015). Furthermore, how the tumor microenvironment reprograms metabolism in TILs during their senescence development should be investigated urgently in order to develop effective immunotherapies.

SUMMARY

Thus, the present disclosure provides a method of modulating lipid metabolism in a cell comprising contacting said cell with an inhibitor of group IVA phosopholipase $A_2$. Also provide is a method of inhibiting induction of senescence in a cell comprising contacting said cell with an inhibitor of group IVA phosopholipase $A_2$. Yet a further embodiment involves a method of enhancing immunotherapeutic efficacy of a cell therapy comprising contacting a therapeutic cell with an inhibitor of group IVA phosopholipase $A_2$.

The cell may be a T cell, such as a CD4+ T cell or a CD8+ T cell. The inhibitor of group IVA phosopholipase $A_2$ may be contacted with said cell more than once. The cell may be located in a tumor microenvironment. The inhibitor of group IVA phosopholipase $A_2$ may be delivered systemically or delivered to the tumor microenvironment.

The cell may be contacted ex vivo and may also introduced into a subject following contacting. The cell may have been originally obtained from said subject prior to contacting with the inhibitor of group IVA phosopholipase $A_2$.

The inhibitor of group IVA phosopholipase $A_2$ may be a pharmacologic inhibitor of group IVA phosopholipase $A_2$, or may be an inhibitory oligonucleotide, such as a ribozyme, an antisense oligonucleotide, an shRNA, an siRNA or a CRISPR-Cas9 gRNA.

In a further embodiment, there is provided a method of treating a subject having cancer comprising administering to said subject a T cell that has been treated with an inhibitor of group IVA phosopholipase $A_2$. Also provided is method of treating a subject having cancer comprising administering to said subject an inhibitor of group IVA phosopholipase $A_2$, such as where the subject is also administered a T cell.

T cell may be a CD4+ T cell or a CD8+ T cell. The inhibitor of group IVA phosopholipase $A_2$ may be contacted with said T cell more than once. The inhibitor of group IVA phosopholipase $A_2$ may be administered more than once. The T cell and/or said inhibitor of group IVA phosopholipase $A_2$ may be delivered to a tumor microenvironment or delivered systemically.

The T cell may be autologous to said subject, and the method may further comprise the step of removing said T cell from said subject and treating said T cell with said inhibitor of group IVA phosopholipase $A_2$.

The inhibitor of group IVA phosopholipase $A_2$ may be a pharmacologic inhibitor of group IVA phosopholipase $A_2$ or may be an inhibitory oligonucleotide, such as a ribozyme, an antisense oligonucleotide, an shRNA, an siRNA or a CRISPR-Cas9 gRNA.

The method may further comprise administering to said subject a second therapy, such as a chemotherapy, an immunotherapy (e.g., a checkpoint inhibitor therapy), radiation, surgery, a toxin therapy, a hormonal therapy or a gene therapy. The cancer may be recurrent, metastatic and/or drug-resistant.

Also provided is a method of assessing T cell senescence comprising assessing group IVA phosopholipase $A_2$ expression level or activity in said cell, wherein an elevated group IVA phosopholipase $A_2$ expression level or activity as compared to a populational average for normal T cells indicates said T cell is senescent or is undergoing senescence. Another embodiment involves a method of assessing therapeutic efficacy of a T cell-based immunotherapy comprising assessing group IVA phosopholipase $A_2$ expression level or activity in said cell, wherein an elevated group IVA phosopholipase $A_2$ expression level or activity as compared to a populational average for normal T cells indicates a reduced likelihood of therapeutic efficacy.

Assessing may comprise measuring group IVA phosopholipase $A_2$ expression level, such as by measuring mRNA level, such as by RT-PCR or Northern blot, or measuring protein expression level, such as by ELISA, RIA or immunoblotting. Assessing may comprise measuring group IVA phosopholipase $A_2$ activity level. The method may further comprise assessing group IVA phosopholipase $A_2$ expression level or activity a second time. The T cell may be a CD4+ T cell or a CD8+ T cell. The T cell may be obtained from a tumor microenvironment. The method may further comprise treating said subject with immunotherapy when group IVA phosopholipase $A_2$ expression level or activity is not elevated. The method may further comprise treating said subject with a cancer therapy other than immunotherapy when group IVA phosopholipase $A_2$ expression level or activity is elevated.

It is contemplated that any embodiment discussed in this specification can be implemented with respect to any method or composition of the disclosure, and vice versa. Furthermore, compositions of the disclosure can be used to achieve methods of the disclosure.

The use of the word "a" or "an" in the claims and/or the specification may mean "one," but it is also consistent with the meaning of "one or more," "at least one," and "one or more than one."

The phrase "one or more" as found in the claims and/or the specification is defined as 1, 2, 3, 4, 5, 6, 7, 8, 9, 10, or more.

Throughout this application, the terms "about" and "approximately" indicate that a value includes the inherent variation of error for the device, the method being employed to determine the value, or the variation that exists among the study subjects. In one non-limiting embodiment, the terms are defined to be within 10%, preferably within 5%, more preferably within 1%, and most preferably within 0.5%.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 1A) nTreg treatment significantly increased SA-β-gal+ T-cell populations in responder naïve CD4+ T cells. Naïve CD4+ T cells were incubated alone or co-cultured with nTreg cells or control effector CD4+CD25-T cells at a ratio of 4:1 in the presence of plate-bound anti-CD3 (2 μg/ml) for 3 days, and then performed SA-β-gal staining. The SA-β-gal+ T-cells were identified with dark blue granules as indicated by the arrows. Scale bar: 20 μm. Data shown in the right panel are means+SD from three independent experiments, and paired t-test was performed. **p<0.01, compared with the medium only and control T cell treatment groups. (FIG. 1B) Tumor cell treatment increased SA-β-gal+ T-cell populations in co-cultured naïve CD4+ T cells. Anti-CD3-activated naïve CD4+ T cells were co-cultured with breast cancer (MCF-7) or melanoma (M586) cells at a ratio of 1:1 for 1 day. The treated CD4+ T cells were then separated and stained with SA-B-gal staining reagents after culture for additional 3 days (dark granules as indicated by the arrows). Scale bar: 20 μm. Data shown in the right panel are means+SD from three independent experiments, and paired t-test was performed. *p<0.05 and **p<0.01 compared with the medium only group. (FIG. 1C) and (FIG. 1D) Naïve CD4+ T cells treated with nTreg (in FIG. 1C) or MCF-7 cells (in FIG. 1D) produced high levels of multiple cytokines. Cell treatments and ratios were identical to the respective experiments in (FIG. 1A) and (FIG. 1B) and cultured for 24 hours. mRNA expression levels of each cytokine were determined by the Real-time PCR analyses. The expression level was normalized to GAPDH expression and adjusted to the levels in naïve CD4+ T cells. Data are means+SD from 3 representative naïve CD4+ T cells. *p<0.05 and **p<0.01, compared with the respective medium only group determined by paired t-test. (FIG. 1E) and (FIG. 1F) Increased senescent T cell populations with a secretory inflammatory cytokine phenotype were developed in both CD4+ and CD8+ T cells from different organs and tumor tissues in melanoma B16F0-bearing mice. Blood, lymph nodes (LN), spleens (SP) and tumor tissues were harvested from the tumor-bearing mice and tumor free littermates when primary tumors reached 10-15 mm in diameters. CD4+ and CD8+ T cells were purified for SA-B-gal staining (in FIG. 1E) and evaluation of cytokine mRNA expression by real-time qPCR (in FIG. 1F). Data shown are means+SD from 7 mice in each group. *p<0.05 and **p<0.01, compared with the respective T cells in wild-type (WT) mice. ##p<0.01 compared with the T cells from blood in WT mice. (FIG. 1G) and (FIG. 1H) Increased senescent T cell populations with a secretory inflammatory cytokine phenotype were developed in T cells from different organs and tumor tissues in breast cancer E0771-bearing mice. When primary tumors reached 10-15 mm in diameters, the tumor-bearing mice and tumor free-littermate controls were sacrificed. T cells from different organs and tumor tissues were purified for SA-β-gal staining (in FIG. 1G) and evaluation of cytokine mRNA expression by real-time qPCR (in FIG. 1H). Data shown are means+SD from 7 mice in each group. *p<0.05 and p<0.01, compared with the respective T cells in WT mice. ##p<0.01 compared with the T cells from blood in WT mice. (FIG. 1I) Accumulated senescent T cells in the TILs from human breast cancer and melanoma tumor tissues. CD3+ T cells were purified from the TILs obtained from freshly digested tumor tissues of melanoma and breast cancer patients by microbeads and SA-β-gal+ cells were determined (dark blue granules as shown by the arrows). Scale bar: 20 μm. Naïve CD4+ and CD8+ T cells from healthy donors were included as controls. Data shown in the right panel are means+SD from T cells of cancer patients and healthy donors. Each dot represents an individual donor/patient. p<0.01, compared between the indicated two groups. BTIL and MTIL: TILs obtained from breast cancer or melanoma patients. (FIG. 1J) TILs from melanoma cancer patients produced high levels of multiple cytokines. Cytokines mRNA expression levels of purified CD3+ TILs from melanoma patients were evaluated by the real-time qPCR. Purified naïve CD4+ or CD8+ T cells from health donors were served as controls. Data shown are means±SD from melanoma patients and healthy T cells. Each dot represents an individual donor/patient. *p<0.05, compared between the indicated two groups.

(FIG. 2A) Alterations of genes involved in glycolysis were identified and ranked in senescent CD8+ T cells after co-culture with nTreg cells for different time points. Gene alterations were normalized to log 2 expression level. Human naïve CD8+ T cells and nTreg cells were isolated from PBMCs of healthy donors and co-cultured at a ratio of 5:1 for different time points. Total RNA was purified and transcriptome analyses of nTreg-treated CD8+ T cells were performed using the Illumina whole-genome Human HT-12 BeadChips. (FIG. 2B) and (FIG. 2C) Gene expression levels of glucose transporters (Glut1 and Glut3) and the key enzymes in glycolysis (HK2, GPI, PFK1, TPI, ENO1, PKM2 and LDHα) in senescent CD4+ (in FIG. 2B) and CD8+ (in FIG. 2C) T cells induced by nTreg cells. CFSE-labeled naïve CD4+ or CD8+ T cells were co-cultured with nTreg cell or control CD4+CD25-T cells at a ratio of 4:1 in the presence of plate-bound anti-CD3 (2 μg/ml) for 3 days. Treated CD4+ and CD8+ T cells were purified and glucose metabolism related gene expression levels were evaluated by the real-time qPCR. Expression levels of each gene were normalized to B-actin expression level and adjusted to the levels in respective naïve CD4+ or CD8+ T cells (served as 1). Data shown are mean±SD from different independent donors. Each dot represents one individual donor. *p<0.05 and **p<0.01, compared with the medium group. (FIG. 2D) and (FIG. 2E) CD4+ T cells purified from blood and TILs had higher gene expression levels of key enzymes in glycolysis in melanoma B16F0-bearing (in FIG. 2D) and breast cancer E0771-bearing (in FIG. 2E) mice than those from blood T cells in wild type mice. Tumor injections and experimental procedures were described as in FIGS. 1A-J. mRNA expression levels of glucose metabolism related genes in purified CD4+ T cells from blood and tumor tissues were evaluated by real-time qPCR. Data shown are means±SD from 7 mice each group. *p<0.05 and **p<0.01, compared with blood T cells in WT mice. (FIG. 2F) TILs from melanoma cancer patients had a normal gene expression profile of glucose metabolism compared with naïve T cells. Gene expression levels of glucose transporters and the key enzymes in glycolysis of purified CD3+ TILs from melanoma patients were evaluated by the real-time qPCR. Purified naïve CD4+ or CD8+ T cells from health donors were served as controls. Data shown are means±SD from melanoma patients and healthy T cells. Each dot represents an individual donor/patient. *p<0.05, compared between the indicated two groups. (FIG. 2G) Addition of high concentration of glucose markedly rescued responder T cell senescence induced by Treg cells. Naïve CD4+ or CD8+ T cells were co-cultured with nTreg or control CD4+CD25-T cells in anti-CD3-coated (2 μg/ml) plates in the presence of different dosages of glucose for 3 days. The treated CD4+ or CD8+ T cells were performed SA-β-gal staining. Data shown are mean±SD from three independent experiments. p<0.01, compared with the medium group. ##p<0.01, compared with the Treg-treated group with normal concentration of glucose (11 mM). (FIG. 2H) High concentration of glucose prevented T-cell senescence induced by tumor cells. Anti-CD3-activated naïve CD4+ or CD8+ T cells were co-cultured with breast cancer MCF-7 at a ratio of 1:1 in the presence of different dosages of glucose for 1 day. The treated T cells were then separated and SA-β-gal+ T cells were determined after culture for additional 3 days. Data shown are mean±SD from three independent experiments. p<0.01, compared with the medium group. ##p<0.01, compared with the MCF7-treated group with normal concentration of glucose (11 mM). (FIG. 2I) Addition of high concentration of glucose did not reduce senescence in already developed senescent T cells. Induction of senescent CD8+ T cells by nTreg cells or MCF-7 tumor cells was identical to the description in FIGS. 1A-J. The senescent CD8+ T cells were purified and cultured in the presence of normal (11 mM) or high (25 mM) dosages of glucose for additional 2 days, and then SA-β-gal+ T cells were determined. Data shown are mean±SD from three independent experiments with similar results.

(FIG. 3A) Alterations of genes involved in lipid metabolism were identified and ranked in senescent CD8+ T cells after co-cultured with nTreg cells for different time points. Cell treatments and analyses were the same as FIG. 2A. Transcriptome analyses of nTreg-treated CD8+ T cells were performed using the Illumina whole-genome Human HT-12 BeadChips. Gene alterations were normalized to log 2 expression level. (FIG. 3B) and (FIG. 3C) Gene expression levels of key enzymes in fatty acid oxidation (CPT-1) and synthesis (ACC1 and FASN), as well as in cholesterol synthesis (HMGCR, HMGCS1, SQLE, and IDI1) in senescent CD4+ (in FIG. 3B) and CD8+ (in FIG. 3C) T cells induced by nTreg cells. CFSE-labeled naïve CD4+ or CD8+ T cells were co-cultured with nTreg cell or control CD4+ CD25-T cells at a ratio of 4:1 in the presence of plate-bound anti-CD3 (2 μg/ml) for 3 days. Treated CD4+ and CD8+ T cells were purified and lipid metabolism related gene expression levels were evaluated by the real-time qPCR. Expression levels of each gene were normalized to B-actin expression level and adjusted to the levels in respective naïve CD4+ or CD8+ T cells (served as 1). Data shown are mean±SD from the independent donors. Each dot represents one individual donor. *p<0.05 and **p<0.01, compared with the medium group. (FIG. 3D) and (FIG. 3E) Gene expression levels of key enzymes in fatty acid and cholesterol metabolism in senescent CD4+ (in FIG. 3D) and CD8+ (in FIG. 3E) T cells induced by MCF-7 tumor cells. Anti-CD3-activated naïve CD4+ and CD8+ T cells were co-cultured with breast cancer MCF-7 cells at a ratio of 1:1 for 1 day. The treated CD4+ and CD8+ T cells were then separated and cultured for additional 3 days, and lipid metabolism related gene expression levels were evaluated by the real-time qPCR. Expression levels of each gene were normalized to B-actin expression level and adjusted to the levels in respective naïve CD4+ or CD8+ T cells (served as 1). Data shown are mean±SD from the independent donor. Each dot represents one individual donor. *p<0.05 and **p<0.01, compared with the medium group. (FIG. 3F) Kinetic gene expression of lipid metabolism-related enzymes in CD8+ T cells treated by nTreg cells at a ratio of 5:1 in the presence of plate-bound anti-CD3 (2 μg/ml) for different time points. Treated CD8+ T cells were purified and gene expression levels of lipid metabolism related enzymes were evaluated by the real-time qPCR. Expression levels of each gene were normalized to B-actin expression level and adjusted to the levels in naïve CD8+ T cells at 8 hour (served as 1). Data shown are mean±SD from 3 independent donors. *p<0.05 and **p<0.01, compared with the medium group. (FIG. 3G) TILs from melanoma cancer patients had a mixed gene expression profile of lipid metabolism. Gene expression levels of key enzymes in fatty acid oxidation and synthesis, as well as in cholesterol synthesis of purified CD3+ TILs from melanoma patients were evaluated by the real-time qPCR. Purified naïve CD4+ or CD8+ T cells from health donors were served as controls. Data shown are means±SD from patient TILs and healthy donor T cells. Each dot represents an individual donor/patient. *p<0.05 and **p<0.01, compared between the indicated two groups.

(FIG. 4A) Flow chart for lipid categories. Lipids mainly consist of cholesterol, fatty acids, triglyceride (TAG), phospholipids and sphingolipids. The main biological functions of lipids are acting as structural components of cell membranes. (FIG. 4B) and (FIG. 4C) Increased levels of total and multiple molecular species in FFA (in FIG. 4B) and CE and decreased total and multiple species in PC, PE and Ceramide (in FIG. 4C) in senescent T cells induced by nTreg cells. Naïve CD8+ T cells were co-cultured with nTreg or control CD4+ CD25-T cells at a ratio of 4:1 in the presence of plate-bound anti-CD3 (2 μg/ml) for 3 days. Treated CD8+ T cells were purified and lipid extracts of T cells from different treatment groups were subjected to the ESI-MS/MS analysis. Data shown are mean±SD from T cells purified from 3 independent donors. *p<0.05 and **p<0.01, compared with the medium group. (FIG. 4D) ESI-MS/MS analysis of the abundance of PE, CE, and Ceramide species in tumor-induced senescent T cells. Anti-CD3-activated naïve CD4+ T cells were co-cultured with breast cancer MCF-7 cells at a ratio of 1:1 for 1 day. The treated CD4+ T cells were then separated and cultured for additional 3 days. Lipid extracts of T cells from different treatment groups were subjected to the ESI-MS/MS analysis. Data shown are mean±SD from T cells purified from 4 independent donors. *p<0.05 and p<0.01, compared with the medium group. (FIG. 4E) Summary of lipidomic analysis results in senescent T cells induced by Treg and tumor cells. Cell treatments are identical to the description in FIGS. 4B-D. Senescent T cells have up-regulated CE and FFA but down-regulated phospholipids. Data are summarized from T cells of 3-4 independent donors with similar results. (FIG. 4F) Addition of the lost phospholipids prevented induction of T cell senescence mediated by Treg cells. Naïve CD4+ T cells were co-cultured with nTreg cells at a ratio of 4:1 in anti-CD3 coated (2 μg/ml) plate in the presence or absence of the indicated dosages of the lipid fractions for 3 days. The treated naïve CD4+ T cells were then analyzed for SA-β-gal expression. Data shown are mean±SD from three independent experiments. p<0.01, compared with the medium and control T cell treatment groups. ##p<0.01, compared with naïve CD4+ T cells treated with nTreg cell group.

(FIG. 5A) Flowchart of pathways for LD synthesis and degradation. ① ACAT1/2 catalyzes the formation of CE from cholesterol and long-chain fatty-acyl-coenzyme A. ② LAL is a key enzyme involved in intracellular hydrolysis of CE and TAG, which breaks down CE and TAG into free cholesterol and fatty acids. ③ cPLA2α generates lysophospholipids from the endoplasmic reticulum (ER) to involve LD formation. (FIG. 5B) and (FIG. 5C) Accumulated LDs in senescent T cells induced by nTreg cells (in FIG. 5B) and tumor cells (in C). Naïve CD4+ and CD8+ T cells were co-cultured with nTreg cells, or with MCF-7 and M586 tumor cells, respectively. The culture condition and ratios are the same as described in FIGS. 1A-J. The co-cultured naïve CD4+ and CD8+ T cells were purified and Oil-red O staining performed. The Oil-red O+ T cells were identified with red granules as indicated by the arrows. Scale bar: 20 μm. Data shown in the right panels are means±SD from three independent experiments. p<0.01, compared with the medium only group. (FIG. 5D) Senescent T cells induced by Treg cells dominantly existed in the Bodipyhi cell populations. Treg-treated senescent T cells were stained with Bodipy 493/503, sorted based on Bodipy 493/503 expression levels (high, medium and low) by FACS, and followed to analyze SA-β-gal expression. Scale bar: 20 μm. Data shown in histogram are mean±SD from 3 independent donor T cells with similar results. p<0.01, compared with naïve T cell only group. ##p<0.01, compared with Bodipy$^{me}$ and Bodipy$^{lo}$ groups. (FIG. 5E) Supplement of the phospholipids inhibited LD formation in T cells treated by Treg cells. Naïve CD4+ T cells were co-cultured with nTreg cells at a ratio of 4:1 in anti-CD3 coated (2 μg/ml) plate in the presence or absence of the indicated dosages of the lipid fractions for 3 days. Oil-red O+ T cells in treated naïve CD4+ T cells were analyzed. Data shown are mean±SD from three independent experiments. **p<0.01, compared with the medium and control T cell treatment groups. #p<0.05 and ##p<0.01, compared with naïve CD4+ T cells treated with nTreg cell group. (FIGS. 5F-G) Gene expression levels of ACAT1 and ACAT2 in senescent T cells were not increased. Naïve CD4+ and CD8+ T cells were co-cultured with nTreg cells (in FIG. 5F), or with MCF-7 breast cancer cells (in FIG. 5G), respectively. The culture condition and ratios are as described in FIGS. 1A-J. The co-cultured naïve CD4+ and CD8+ T cells were purified and mRNA expression levels of ACAT1 and ACAT2 were determined by the Real-time qPCR. The expression level was normalized to GAPDH expression and adjusted to the levels in naïve T cells. Data are means±SD from three independent experiments with similar results. *p<0.05 and p<0.01, compared with the T cells in respective medium only group. (FIG. 5H) Treatment with ACAT inhibitor avasimible did not down-regulate CE in senescent CD8+ T cells induced by Treg cells. Naïve CD8+ T cells were pretreated with ACAT inhibitor avasimible for 24 hours and then co-cultured with nTreg cells at a ratio of 4:1 in anti-CD3 coated (2 μg/ml) plate for 3 days. The treated naïve CD8+ T cells were then purified and CE species were evaluated by the ESI-MS/MS. Data shown are mean±SD from T cells purified from 2 independent donors. (FIGS. 5I-J) Treatment with avasimible dramatically reduced senescent T (in FIG. 5I) and Oil red O+ T cell (in FIG. 5J) populations in naïve CD4+ and CD8+ T cells induced by Treg cells. Naïve CD4+ and CD8+ T cells were pretreated with ACAT inhibitor avasimible for 24 hours and then co-cultured with nTreg cells at a ratio of 4:1 in anti-CD3 coated (2 μg/ml) plate for 3 days. The treated naïve CD4+ and CD8+ T cells were purified and performed SA-β-gal staining (in FIG. 5I), and Oil-red O staining (in FIG. 5J), respectively. Data shown are mean±SD from 3 independent experiments with similar results. p<0.01, compared with the medium only group. (FIG. 5K) LIPA was significantly down-regulated in senescent T cells during the senescence development mediated by Treg cells. Naïve CD8+ T cells were co-cultured with nTreg cell at a ratio of 5:1 in the presence of plate-bound anti-CD3 (2 μg/ml) for different time points. Treated CD8+ T cells were purified and gene expression levels of LIPA were evaluated by real-time qPCR. The expression level was normalized to GAPDH expression and adjusted to the levels in naïve T cells at 8 hours. Data are means±SD from three independent experiments with similar results p<0.01, compared with the T cells in respective medium only group. (FIGS. 5L-M) Inhibition of lipase with the inhibitor orlistat dramatically increased cell senescence (in FIG. 5L) and promoted LD formation (in FIG. 5M) in naïve T cells. Naïve CD8+ T cells were cultured in anti-CD3 coated (2 μg/ml) plates in the presence or absence of lipase inhibitor orlistat (5 μM) for 3 days. The treated CD8+ T cells were performed SA-β-gal (in FIG. 5L) and Oil-red O (in FIG. 5M) staining. Data shown are mean±SD from T cells purified from 3 independent donors with similar results. p<0.01, compared with the medium only group.

(FIGS. 6A-B) Kinetically increased gene expression levels of cPLA2α in T cells during the senescence induction. Naïve CD8+ and CD4+ T cells were co-cultured with nTreg cells (in FIG. 6A) or with MCF-7 breast cancer cells (in FIG. 6B) for different time points, respectively. The culture condition and ratios are same as described in FIGS. 1A-J. The co-cultured naïve CD4+ and CD8+ T cells were purified and mRNA expression levels of cPLA2α gene were determined by the Real-time qPCR. The expression level was normalized to GAPDH expression and adjusted to the levels in naïve T cells at 4 hours. Data are means±SD from three independent experiments with similar results. *p<0.05 and **p<0.01, compared with the T cells in respective medium only group. (FIG. 6C) Increased cPLA2α protein expression in Treg-induced senescent T cells. Naïve CD4+ and CD8+ T cells were co-cultured with or without Treg cells or control CD4+CD25-T cells at a ratio of 4:1 in the presence of plate-bound anti-CD3 (2 μg/ml) for 3 days. Protein expression levels of cPLA2α in treated T cells were analyzed by the western-blot. nTreg-1 and nTreg-2 cells are nTreg cells purified from 2 healthy donors. (FIGS. 6D-E) T cells purified from blood and tumors had high gene expression levels of cPLA2α in melanoma B16F0-bearing (in FIG. 6D) and breast cancer E0771-bearing (in FIG. 6E) mice. Tumor injections and experimental procedures were described same as in FIGS. 1A-J. mRNA expression levels of cPLA2α in purified CD4+ and CD8+ T cells from blood and tumor tissues were evaluated by the real-time qPCR. Data shown are means±SD from 7 mice in each group. *p<0.05 and p<0.01, compared with the blood T cells in WT mice. (FIG. 6F) The cPLA2α expression was co-existed with the accumulated LDs in Treg-induced senescent T cells. Immunofluorescence double staining with anti-cPLA2α antibody and bodipy 493/503 respectively in the same slide from responder CD4+ T cells treated with nTreg or control CD4+CD25-effector T cells. Scale bar: 20 μm. (FIG. 6G) Inhibition of cPLA2α by specific pharmacologic inhibitor blocked LD formation in Treg-induced senescent T cells. Naïve CD4+ and CD8+ T cells were pretreated with cPLA2α inhibitor MAFP for 24 hours and then co-cultured with nTreg cells at a ratio of 4:1 in anti-CD3 coated (2 μg/ml) plate for 3 days. The treated naïve CD4+ and CD8+ T cells were then purified and performed Oil-red O staining. Data are means±SD from three independent experiments with similar results p<0.01, compared with the medium group without inhibitor treatment. (FIG. 6H) Inhibition of cPLA2α dramatically reversed the down-regulation of phospholipids (SM, PC and LPC) and up-regulation of CE in senescent T cells induced by Treg cells. Cell treatment and co-culture condition are same as in FIG. 6G. The treated CD8+ T cells were then purified and the abundance of different lipids species were evaluated by the ESI-MS/MS. (FIG. 6I) cPLA2α signaling regulated cell cycle regulatory molecules in senescent T cells. Cell treatment and co-culture condition are same as in FIG. 6G. The treated naïve CD4+ T cells were purified and protein expression levels of cPLA2α, p53, and p21 were analyzed by the western-blot. Protein levels of cPLA2α, P53 and P21 shown in the bottom histogram were quantitatively analyzed and compared against the GAPDH expression levels with a densitometer. Results shown in the histogram are mean #SD from three independent experiments. **p<0.01, compared with the medium only treatment group; and ##p<0.01, compared with CD4 and Treg co-culture group without MAFP treatment. (FIG. 6J) and (FIG. 6K) Inhibition of cPLA2α significantly prevented induction of cell senescence (in FIG. 6J) and lost costimulatory molecules CD27 and CD28 (in FIG. 6K) in responder T cells mediated by Treg cells. Cell treatment and co-culture condition are same as in FIG. 6G. The treated CD4+ and CD8+ T cells were purified, and SA-β-gal expression in treated T cells was determined (in FIG. 6J), and CD27 and CD28 expression determined with flow cytometry analyses (in FIG. 6K). Data shown are mean±SD from representative of three independent experiments with similar results. *p<0.05 and p<0.01, compared with the T cells without MAFP treatment. (FIG. 6L) MAFP treatment markedly blocked inflammatory cytokine release in responder T cells induced by Treg cells. Cell treatment and co-culture condition are same as in FIG. 6G. The treated naïve CD4+ and CD8+ T cells were purified and mRNA expression levels of each cytokine were determined by the Real-time qPCR. The expression level was normalized to GAPDH expression and adjusted to the levels in naïve CD8+ T cells in medium. Data are means±SD from 3 representative naïve CD8+ T cells. p<0.01, compared with the naïve CD8+ T cells in medium only group; #p<0.05 and ##p<0.01, compared with CD8 and Treg co-culture group without MAFP treatment.

(FIG. 7A) Pretreatment of naïve CD8+ T cells with an ATM inhibitor KU55933 significantly prevented Treg-induced up-regulated CE and FFA in responder T cells. Anti-CD3 activated CD8+ T cells were pretreated with or without KU55933 (10 μM) for 1 day, and then co-cultured with nTreg cells at a ratio of 4:1 for 3 days. The treated CD8+ T cells were purified and the abundance of CE and FFA species were evaluated by the ESI-MS/MS analysis. Results shown in the histogram are mean±SD from 2 independent CD8+ T cells. *p<0.05, compared with the co-culture group without inhibitor treatment. (FIGS. 7B-C) KU55933 treatment decreased the cPLA2α expression in responder T cells mediated by Treg cells. Cell treatment and ratios were identical as in (FIG. 7A), and the treated CD8+ T cells with different time points were then purified. cPLA2α mRNA expression levels in Treg-induced senescent T cells were evaluated with the Real-time qPCR and then normalized to GAPDH expression level and adjusted to the levels in CD8+ T cells without MAFP treatment (served as 1) (in FIG. 7B). Protein expression levels of cPLA2α in senescent T cells were determined by the flow cytometry analysis (in FIG. 7C). Data shown in (FIG. 7B) are mean±SD from 3 independent experiments with similar results. p<0.01, compared with the naïve CD8+ T cells in medium only group; and ##p<0.01, compared with CD8 and Treg co-culture group without KU55933 treatment. (FIGS. 7D-E) Treatment with KU55933 dramatically reduced senescent T (in FIG. 7D) and Oil red O+ T cell (in FIG. 7E) populations in naïve CD4+ and CD8+ T cells induced by Treg cells. Naïve CD4+ and CD8+ T cells were pretreated with ATM inhibitor KU55933 (10 μM) for 24 hours and then co-cultured with nTreg cells at a ratio of 4:1 in anti-CD3 coated (2 μg/ml) plate for 3 days. The treated naïve CD4+ and CD8+ T cells were purified and performed SA-β-gal staining (in FIG. 7D) and Oil-red O staining (in FIG. 7E), respectively. Data shown are mean±SD from 3 independent experiments with similar results. p<0.01, compared with the naïve T cells in medium only group; and ##p<0.01, compared with naïve T cells and Treg co-culture group without KU55933 treatment. (FIG. 7F) Phosphorylated P38 and ERK were co-localized with LDs in human Treg-induced senescent CD4+ T cells. Immunofluoresence double staining with antibodies against p-ERK or p-P38 with Bodipy 493/503 in the same slide of responder T cells treated with Treg or control CD4+CD25-effector T cells. Scale bar: 20 μm. (FIG. 7G) LDs and phosphorylated STAT1/STAT3 were co-localized in Treg-induced senescent CD4+ T cells. Immunofluorescence double staining with antibodies against p-STAT1 or p-STAT3 with bodipy 493/503 in the same slide from responder T cells treated with Treg or control CD4+CD25-effector T cells. Scale bar: 20 μm. (FIG. 7H) Blockages of ATM, MAPK and STAT1/STAT3 signaling pathways significantly down-regulated cPLA2α expression in senescent T cells induced by Treg cells. Naïve CD4+ T cells were pretreated with different inhibitors for 24 hours and then co-cultured with Treg cells at a ratio of 4:1 in anti-CD3 coated (2 μg/ml) plate for 3 days. cPLA2α protein expression levels in treated naïve CD4+ T cells were analyzed by the western-blot. Protein levels of cPLA2α shown in the lower histogram were quantitatively analyzed and compared against the GAPDH expression levels with a densitometer. p<0.01, compared with the medium group; ##p<0.01, compared with CD4 and Treg co-culture group without inhibitor treatment. (FIGS. 7I-J) Inhibitions of MAPK and STAT1/STAT3 signaling pathways dramatically reduced Oil red O+ T (in FIG. 7I) and senescent T (in FIG. 7J) cell populations in naïve CD4+ and CD8+ T cells induced by Treg cells. Cell treatment and ratios were the same in FIGS. 7I and 7J. The treated naïve CD4+ and CD8+ T cells were purified and then Oil-red O+ (in FIG. 7I) and SA-β-gal+ (in FIG. 7J) T cell populations were detected, respectively. Data shown are mean±SD from 3 independent experiments with similar results. p<0.01, compared with the naïve T cells in medium only group.

(FIG. 8A) Administration of MAFP enhanced anti-tumor immunity against melanoma mediated by Pmel-1 T cells. Mouse B1610 tumor cells (2× 10⁵/mouse) were subcutaneously injected into C57BL/6 mice. The activated Pmel-1 T cells (2×10⁶) were adoptively transferred into B16F10-bearing mice at day 6 post tumor inoculation. MAFP (7.5 mg kg-1/mouse) was injected intraperitoneally into the mice at day 1, 4, 7, and 10 after T cell transfer. Tumor volumes were measured and presented as mean±SD (n=6 mice per group). (FIG. 8B) MAFP treatment significantly decreased the cPLA2α expression in Pmel-1 T cells in B16F10-bearing mice. Cell treatment and adoptive trans-

US 12,590,309 B2

Figure 1:
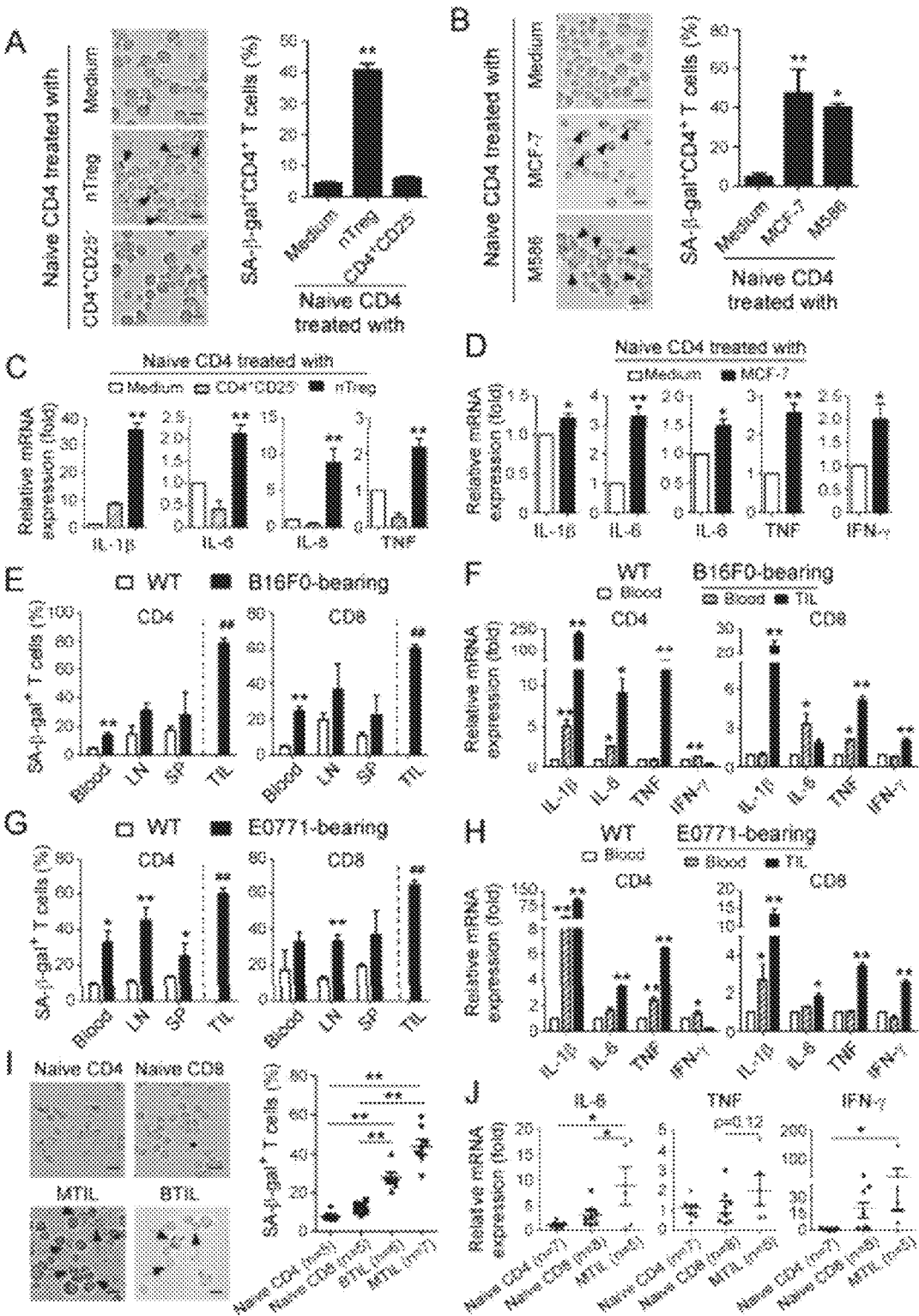
FIGS. 1A-J. Accumulation of senescent T cells in the tumor microenvironments.
Figure 2:
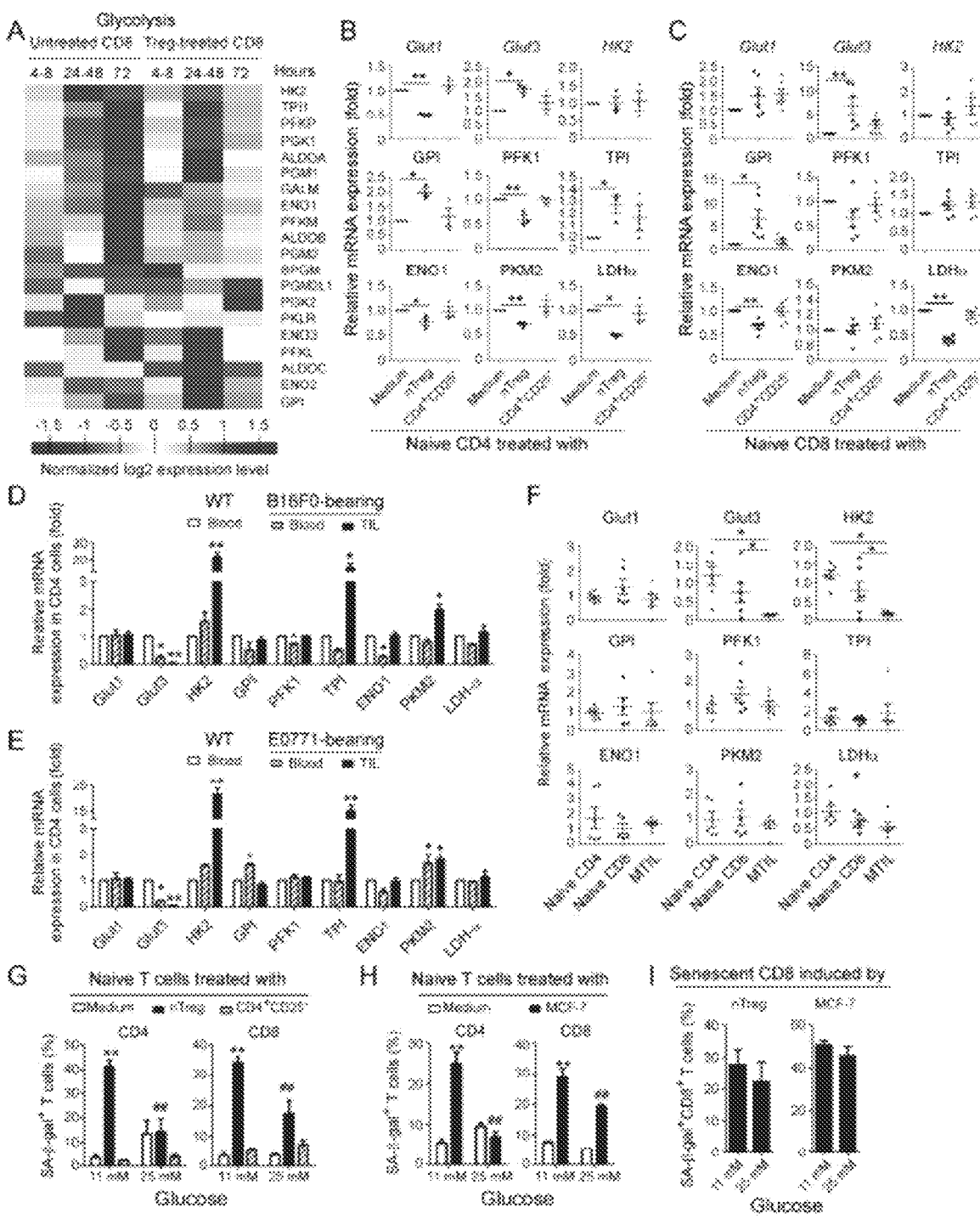
FIGS. 2A-I. Senescent T cells have active glucose metabolism.
Figure 3:
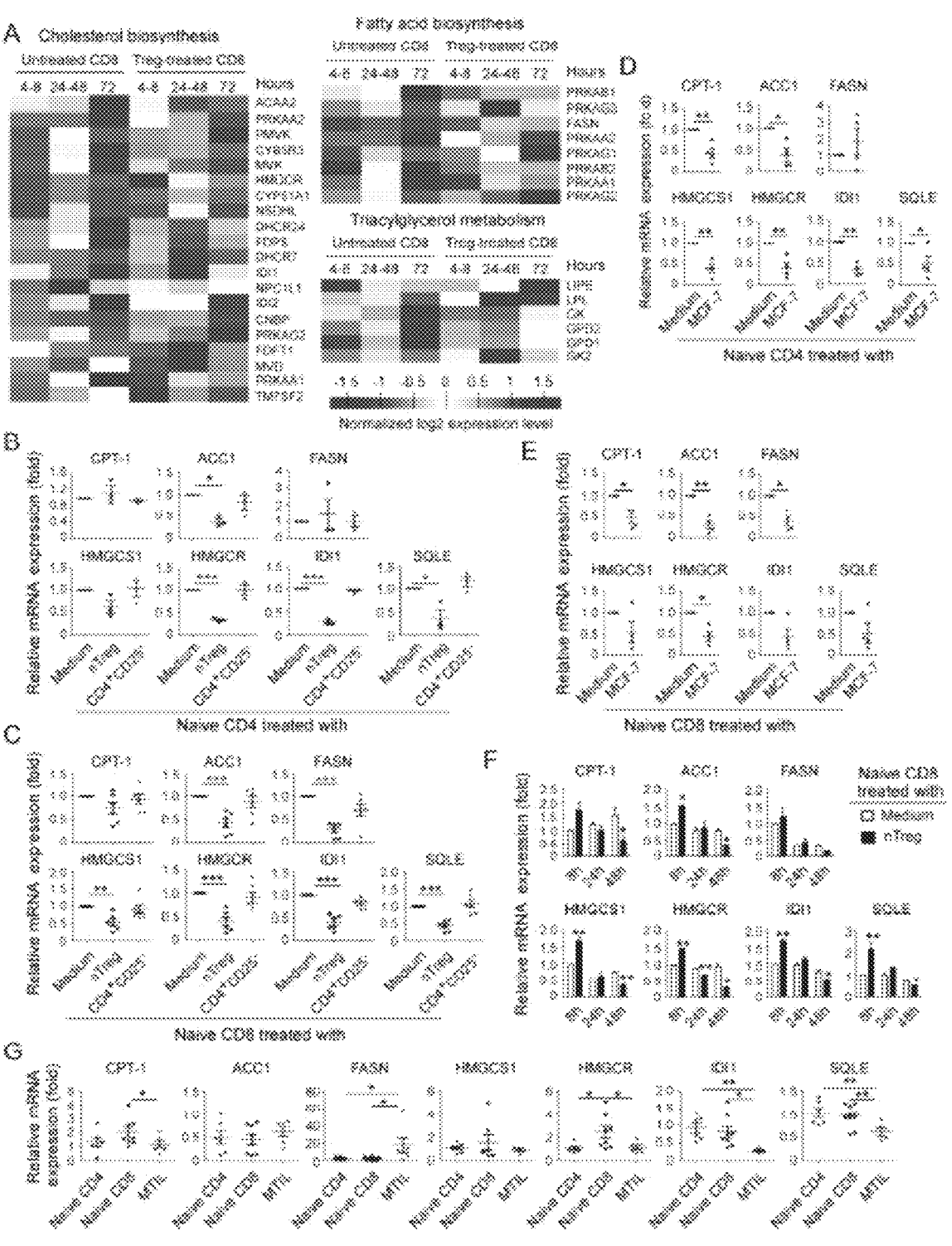
FIGS. 3A-G. Senescent T cells have unbalanced lipid metabolism.
Figure 4:
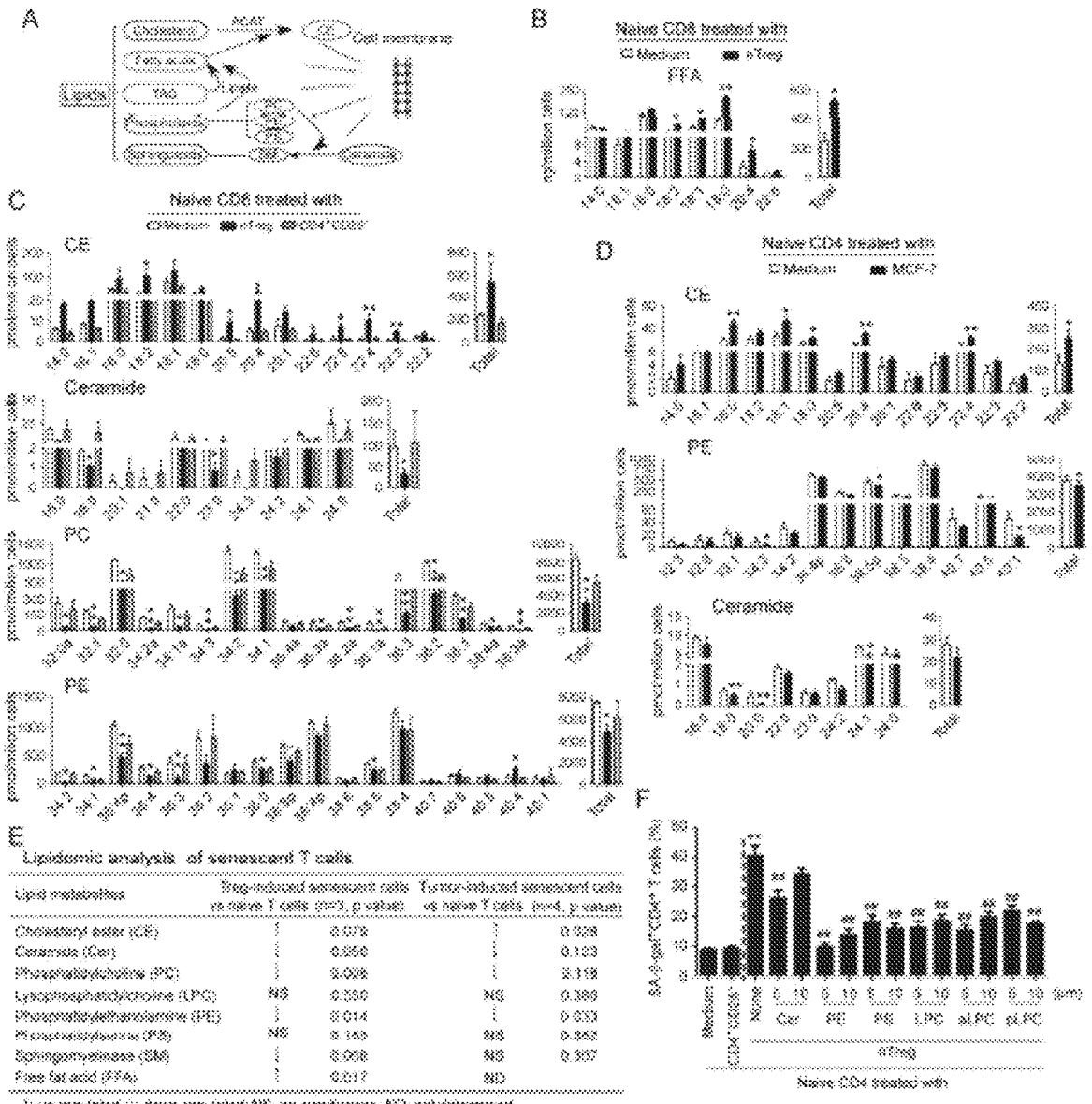
FIGS. 4A-F. Alterations of lipid species in senescent T cells induced by Treg cells and tumor cells.
Figure 5:
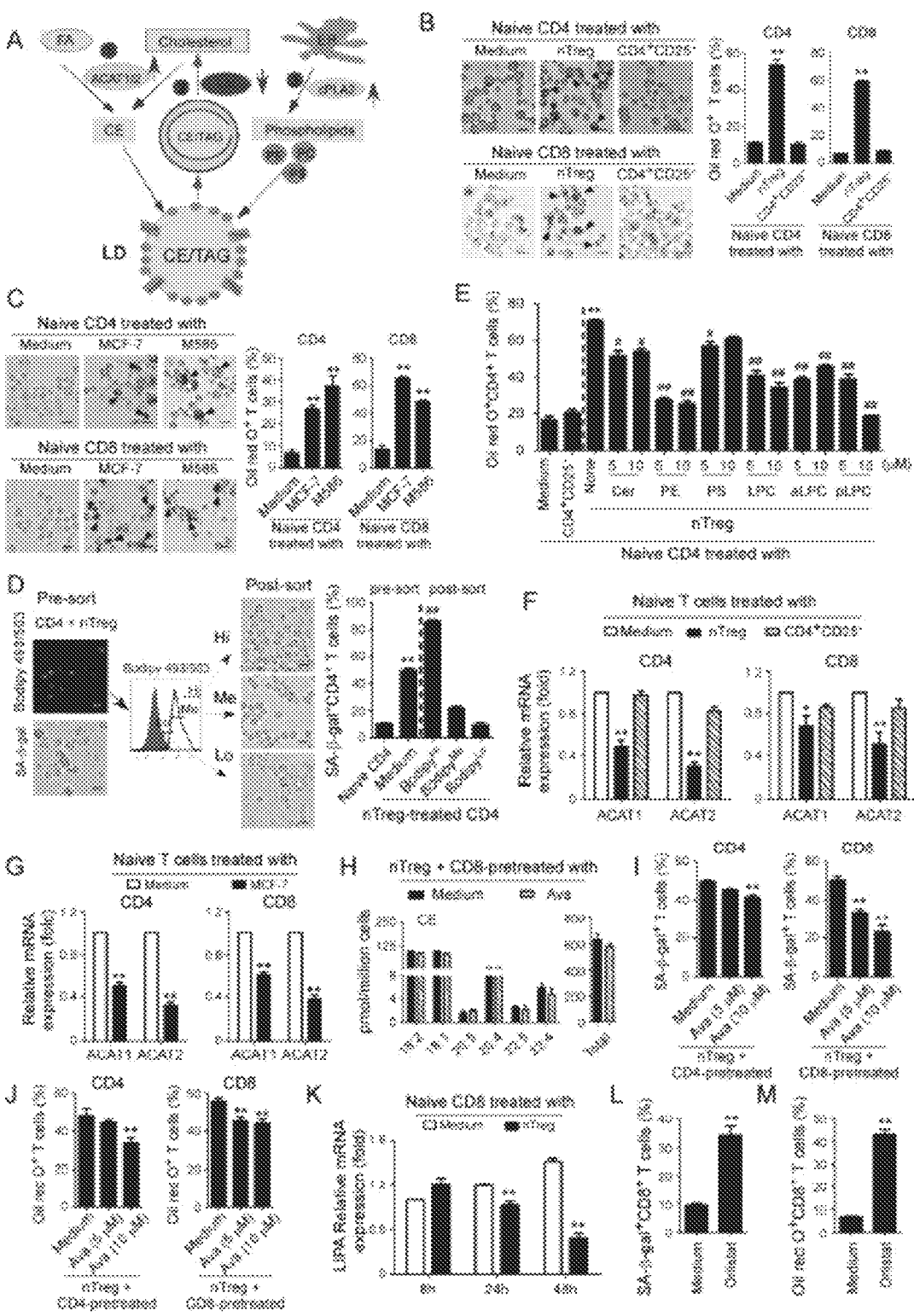
FIGS. 5A-M. Accumulated LDs involve the development of T cell senescence mediated by Treg cells and tumor cells.
Figure 6:
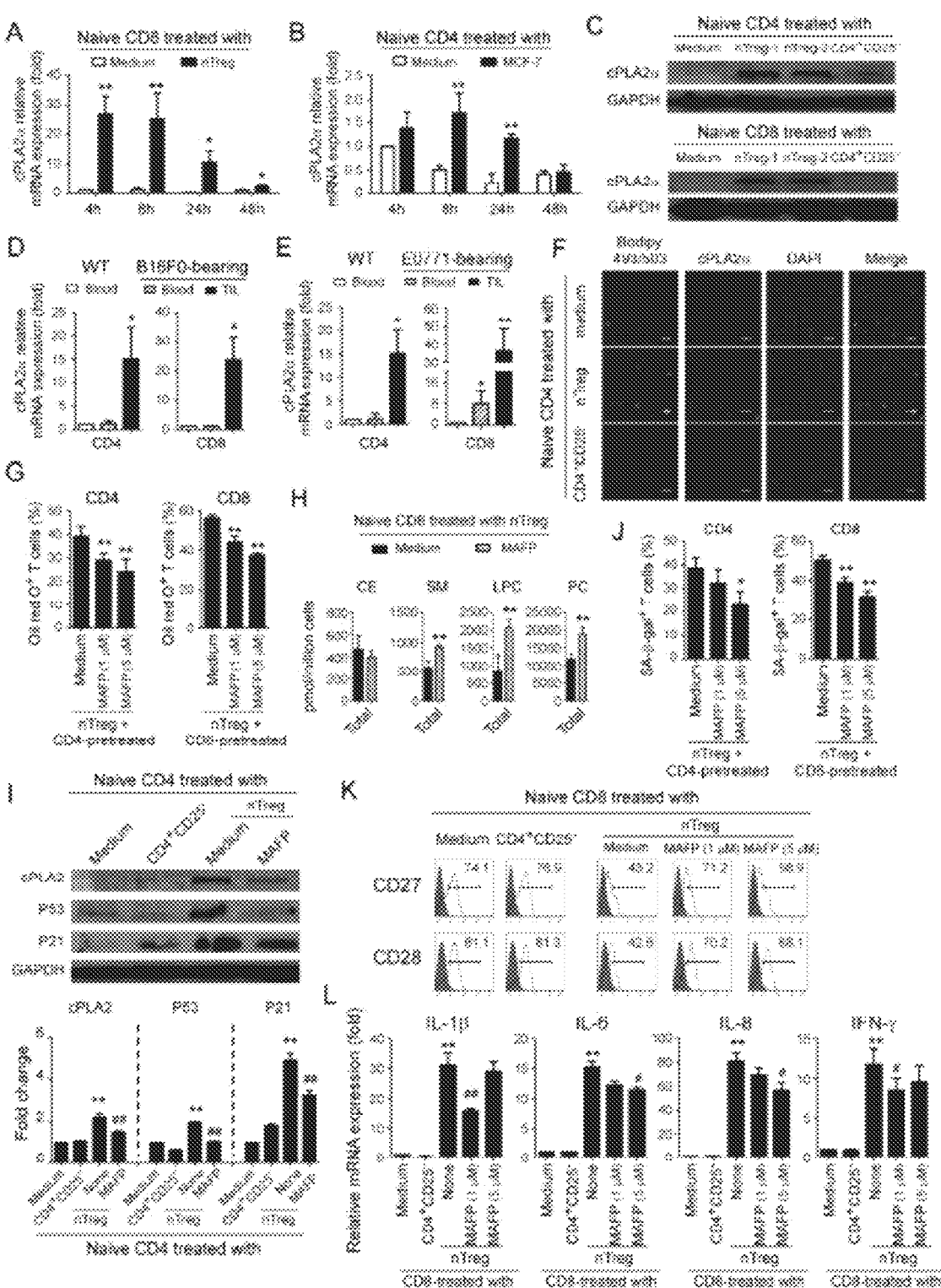
FIGS. 6A-L. Elevated cPLA2a directs the LD accumulation and senescence induction in T cells.
Figure 7:
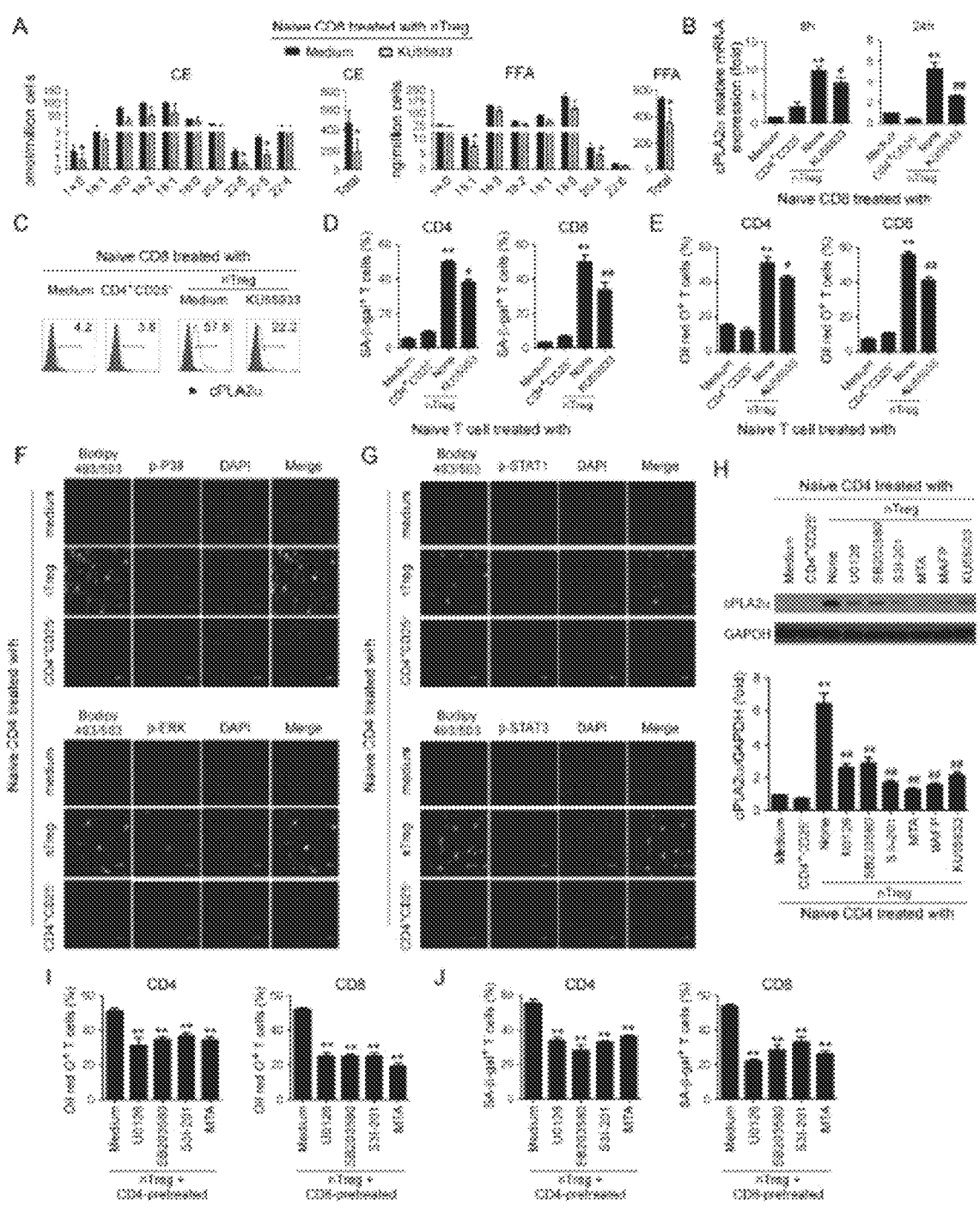
FIGS. 7A-J. MAPK signaling cooperates with STAT signaling to regulate cPLA2α and lipid metabolism in senescent T cells.
Figure 8:
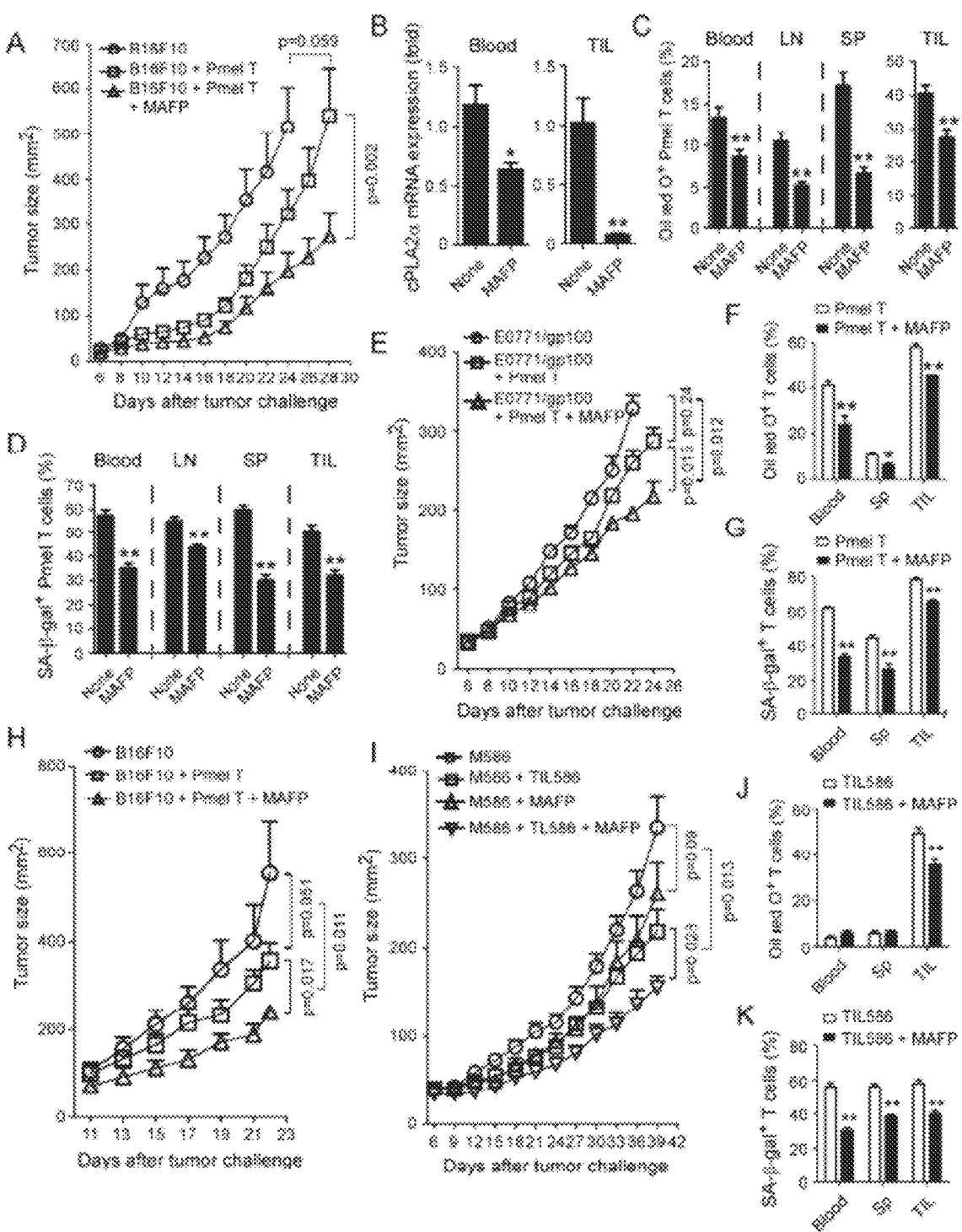
FIGS. 8A-K. Reversal of T cell senescence via reprogramming of T cell lipid metabolism through cPLA2α inhibition enhances anti-tumor immunity and tumor immunotherapy in vivo.

13 fer procedure were identical as in FIG. 8A. The transferred Peml-1 T cells were isolated and recovered at day 28 post tumor injection from blood and tumor tissues for subsequent qPCR analysis. Expression levels were normalized to B-actin expression level and adjusted to the levels in T cells without MAFP treatment (served as 1). Data shown are mean±SD (n=6 mice per group).p<0.01 between the two groups. (FIGS. 8C-D) Inhibition of cPLA2α with MAFP markedly blocked the induction of senescence and formation of LDs in transferred Pmel-1 T cells in B16F10-bearing mice. Cell treatment and adoptive transfer procedure were identical as in (FIG. 8A). Blood, spleens, lymph nodes and tumors were harvested at day 28 post tumor injection. The transferred Pmel-1 T cells in different organs and tumors were isolated for Oil-red O staining (in FIG. 8C) and SA-β-gal staining (in FIG. 8D), respectively. Data shown are mean±SD from 6 mice each group. p<0.01, compared with T cells from the group without MAFP treatment. (FIG. 8E) MAFP treatment enhanced anti-tumor immunity against breast cancer mediated by Pmel-1 T cells in NSG mice. Mouse E0771 tumor cells transduced with retroviral vector encoding melanoma tumor antigen gp100 were subcutaneously injected into NSG mice on day 0. On day 6, activated Pmel-1 T cells were adoptively transferred into tumor-bearing mice. MAFP were injected intraperitoneally into the mice at day 1, 4, 7, and 10 after adoptive transfer of Pmel-1 T cells. Tumor sizes were measured and presented as mean±SD (n=5 mice per group). (FIGS. 8F-G) MAFP treatment significantly blocked the induction of senescence and formation of LDs in transferred Pmel-1 T cells in E0771-bearing mice. Cell treatment and adoptive transfer procedure were identical as in (FIG. 8E). Blood, spleens, and tumors were harvested at day 24 post tumor injection. The transferred Pmel-1 T cells in different organs and tumors were isolated for Oil-red O staining (in FIG. 8F) and SA-B-gal staining (in FIG. 8G), respectively. Data shown are mean±SD from 5 mice each group. p<0.01, compared with T cells from the group without MAFP treatment. (FIG. 8H) Treatment with MAFP markedly inhibited tumor growth of late stage melanoma. Mouse B16F10 tumor cells (2× 105/mouse) were subcutaneously injected into C57BL/6 mice. The activated Pmel-1 T cells (2×10⁶) were adoptively transferred into B16F10-bearing mice at day 11 post tumor inoculation. MAFP (7.5 mg kg-1/mouse) was injected intraperitoneally into the mice at day 1, 4, 7, and 10 after T cell transfer. Tumor volumes were measured and presented as mean±SD (n=6 mice per group). (FIGS. 8I-K) Treatment with MAFP prevented tumor-specific T cell senescence and enhanced anti-tumor immunity in human melanoma in NSG mice. Human 586mel tumor cells (5×10⁶/mouse) were subcutaneously injected into NSG mice. Tumor-specific CD8+ TIL586 cells (5× 10⁶/mouse) were i.v. injected on day 5 post tumor injection. MAFP was injected intraperitoneally into the mice at day 1, 4, 7, and 10 day after adoptive transfer of CD8+ TIL586 T cells. Tumor volumes were measured and presented as means±SD (in FIG. 8I) (n=5 mice per group). Blood, spleens, and tumors were harvested at day 39 post injection. The transferred human TIL586 T cells in different organs and tumors were isolated for subsequent Oil-red O staining (in FIG. 8J) and SA-β-gal staining (in FIG. 8K), respectively. p<0.01, compared with the group of TIL586 without MAFP treatment.

FIGS. 9A-F. Increased senescent T cell populations and accumulated lipids in T cells in old mice compared those in adult mice. CD4+ and CD8+ T cells were purified from blood and spleens of old mice (age is around 12 months) and adult mice (age is about 8-week). SA-β-gal expression was

Figure 9:
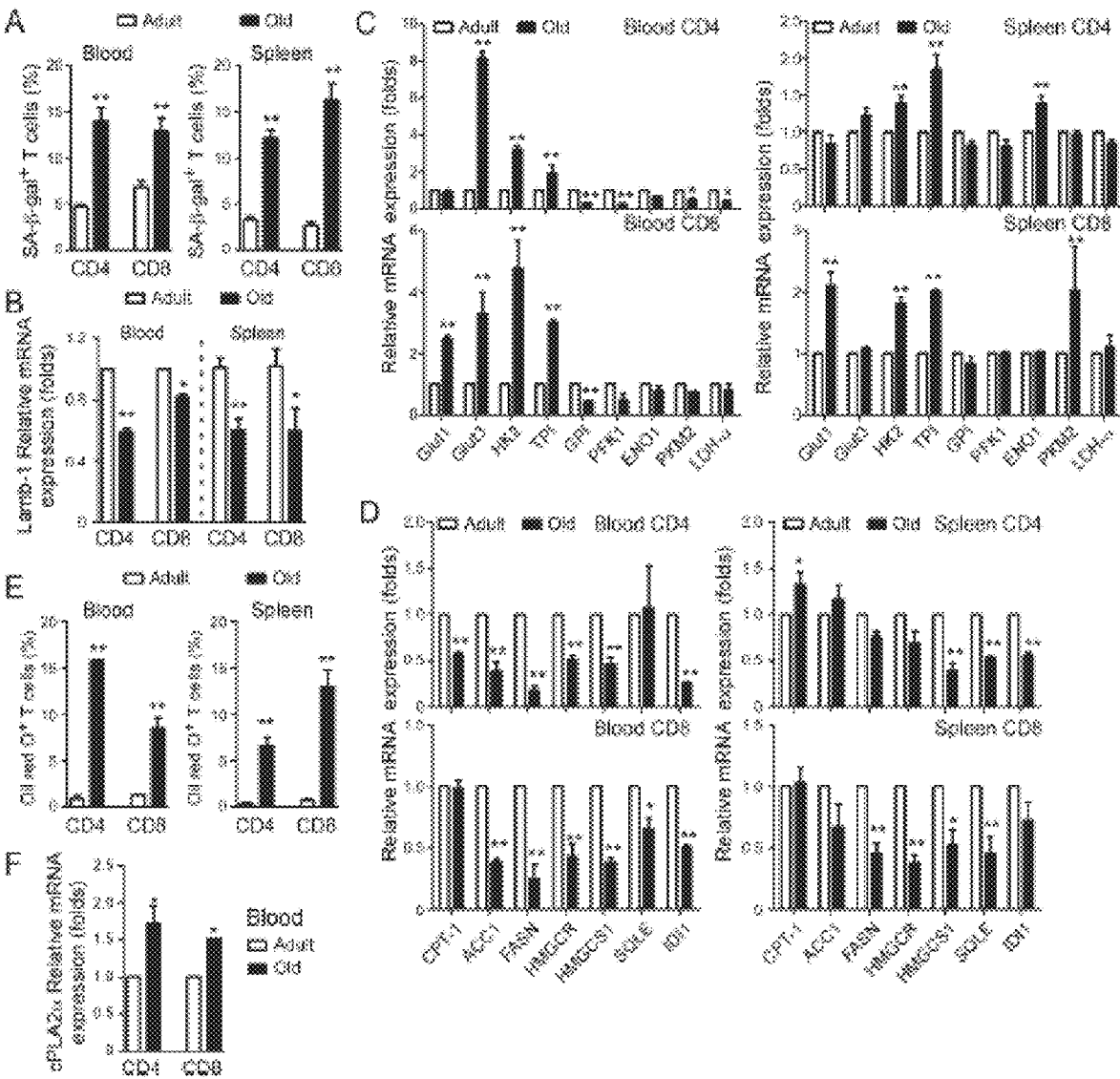

14 determined (in FIG. 9A). Lamb-1 mRNA expression was determined by RT-qPCR analysis (in FIG. 9B). Glucose (FIG. 9C) and Lipid (FIG. 9D) metabolism related gene expressions were determined by RT-qPCR analysis. Lipid accumulation in T cells was determined by the Oil red O staining (in FIG. 9E). cPLA2α expression was determined by RT-qPCR analysis (in FIG. 9F). Data (in A to F) are means±SD from three independent experiments with similar results *p<0.05 and **p<0.01, compared with the adult mice.

Figure 10:
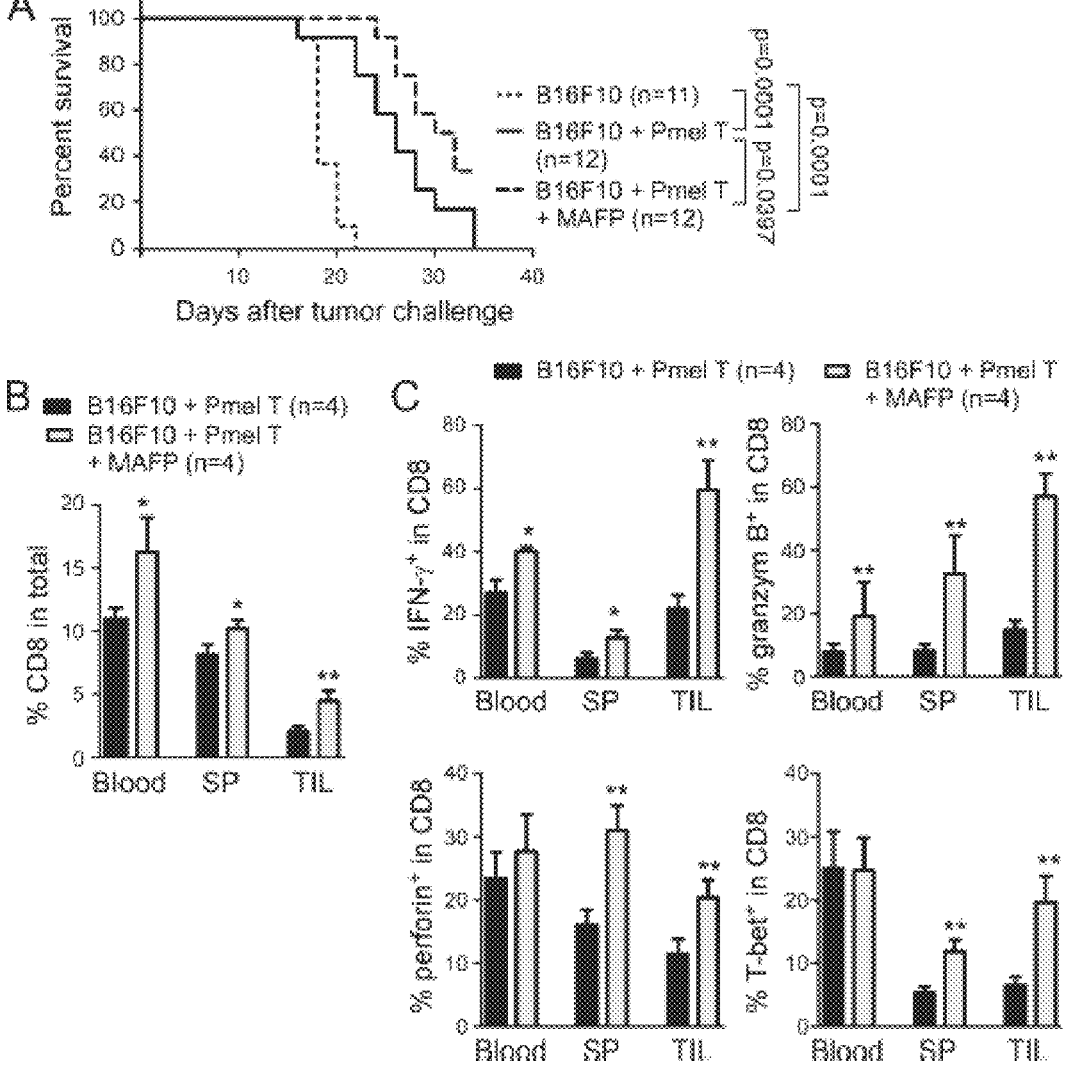

FIGS. 10A-C. cPLA2α inhibition by MAFP improves the overall survival and enhances anti-tumor immunity in vivo. Mouse B1610 tumor cells (2× 105/mouse) were subcutaneously injected into C57BL/6 mice. The activated Pmel-1 T cells (2×10⁶) were adoptively transferred into B16F10-bearing mice at day 6 post tumor inoculation. MAFP (7.5 mg·kg-1/mouse) was injected intraperitoneally into the mice at day 1, 4, 7, and 10 after T cell transfer. Tumor sizes were measured every other day and calculated according to a standard formula (length×width²×0.52) (n=11-12 mice per group). The experiments were terminated at the endpoint determined by the ethical considerations (tumor volume>2000 mm³). Kaplan-Meier survival analysis shows that mice treated with Pmel T cells combined with MAFP treatment had longer survival than other groups (p<0.05) (in FIG. 10A). The percentages of CD8+ T cells (in FIG. 10B), IFN-γ+CD8+, Granzyme B+CD8+, perforin+CD8+ and T-bet+CD8+ (in FIG. 10C) were determined by the flow cytometry analyses. Data are means±SD from three independent experiments with similar results. *p<0.05 and **p<0.01, compared with the tumor-bearing mice with Pmel T cell treatment only group.

Figure 11:
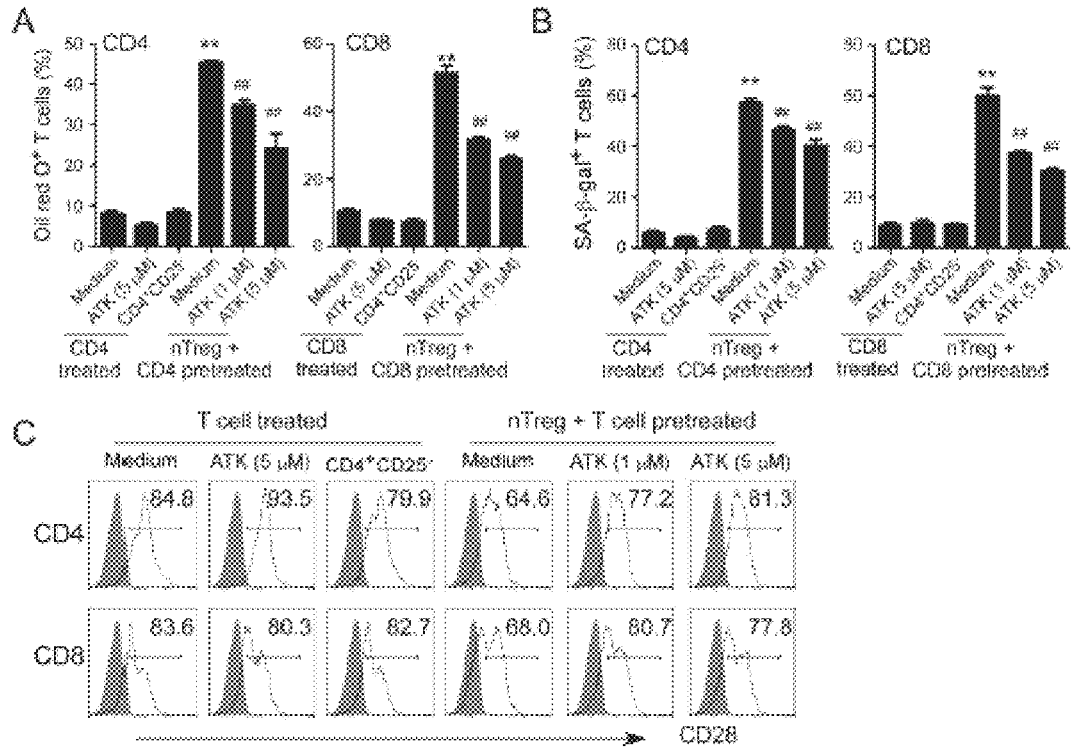
Figure 12:
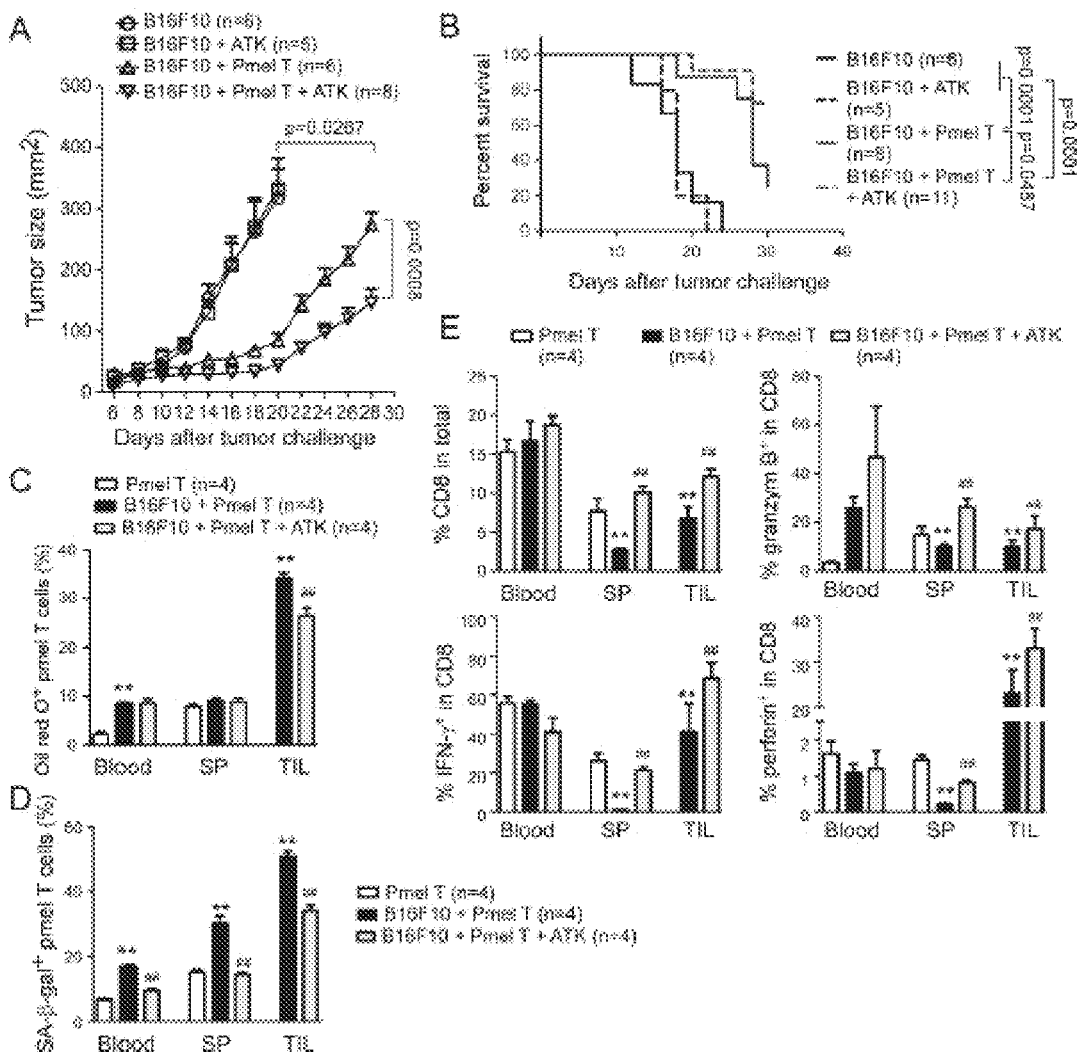

FIGS. 11A-C. cPLA2α inhibitor ATK can prevent T cell senescence induced by Treg cells in vitro. Naïve CD4+ and CD8+ T cells were pretreated with cPLA2α inhibitor ATK for 24 hours and then co-cultured with nTreg cells at a ratio of 4:1 in anti-CD3 coated (2 µg/ml) plates for 3 days. The treated naïve CD4+ and CD8+ T cells were then purified. Oil-red O (in FIG. 11A) and SA-β-gal (in FIG. 11B) expression in treated T cells were determined. In addition, CD27 and CD28 expression was determined with the flow cytometry analyses (in FIG. 11C). Data are means±SD from three independent experiments with similar results p<0.01, compared with the medium group without inhibitor treatment. FIGS. 12A-E**. cPLA2α inhibitor ATK enhances anti-tumor immunity and tumor immunotherapy in vivo.

FIGS. 12A-E. cPLA2α inhibitor ATK enhances anti-tumor immunity and tumor immunotherapy in vivo. Mouse B1610 tumor cells (2×10⁵/mouse) were subcutaneously injected into C57BL/6 mice. The activated Pmel-1 T cells (2×10⁶) were adoptively transferred into B16F10-bearing mice at day 6 post tumor inoculation. Pmel-1 T cells combined with ATK were pretreated with ATK (0.5 µM) for 2 hours and then were injected into B16F10-bearing mice. ATK (10 mg·kg-1/mouse) was injected intraperitoneally into the mice at day 1, 4, 7, and 10 after T cell transfer. Tumor volumes were measured and presented as mean±SD (n=5-8 mice per group) (in FIG. 12A). The percentages of mouse survival in each group were determined by the Kaplan-Meier survival analysis (in FIG. 12B). Blood, spleens, and tumors were harvested at day 28 post tumor injection. The transferred Pmel-1 T cells in different organs and tumors were isolated for Oil-red O staining (in FIG. 12C) and SA-β-gal staining (in FIG. 12D), respectively. The percentages of CD8+ T cells, IFN-Y+CD8+, Granzyme B+CD8+, and perforin+CD8+ (in FIG. 12E) were determined by the flow cytometry analyses. Data shown are mean±SD from 4 mice each group. **p<0.01, compared with Pmel-1 T cells alone group, ##p<0.01, compared with Pmel-1 T cells with ATK treatment.

FIGS. 13A-G, related to FIGS. 1A-J-Senescent T cells have an active cytokine secretion profile induced by tumor cells and Treg cells. (FIG. 13A) nTreg treatment significantly increased SA-β-gal+ T-cell populations in responder naïve CD8+ T cells. Naïve CD8+ T cells were incubated alone or co-cultured with nTreg cells or control effector CD4+CD25-T cells at a ratio of 4:1 in the presence of plate-bound anti-CD3 (2 μg/ml) for 3 days. SA-β-gal+ T-cells in treated naïve CD8+ T cells were determined and identified with dark blue granules by the arrows. Scale bar: 20 μm. Data shown in the right panel are means±SD from three independent experiments. p<0.01, compared with the medium only and control T cell treatment groups. (FIG. 13B) Tumor cell treatment increased SA-β-gal+ T-cell populations in the co-cultured naïve CD8+ T cells. Anti-CD3-activated naïve CD8+ T cells were co-cultured with MCF-7 or M586 cells at a ratio of 1:1 for 1 day. The treated CD8+ T cells were then separated and performed SA-β-gal staining after culture for additional 3 days. The SA-β-gal+ T-cells were identified with dark blue granules as indicated by the arrows. Scale bar: 20 μm. Data shown in the right panel are means±SD from three independent experiments. p<0.01 compared with the medium only group. (FIG. 13C) Down-regulation of CD27 and CD28 molecules in naïve CD4+ T cells treated with nTreg cells. Cell treatment and procedure were the same as in FIG. 13A. CD27 and CD28 expression in treated naïve CD4+ T cells were analyzed by the flow cytometry. (FIG. 13D) Senescent CD8+ T cells treated with MCF-7 tumor cells for 4 hours produced high levels of multiple inflammatory cytokines. Cell treatment and ratio were identical to the experiments in FIG. 13B. mRNA expression levels of each cytokine were determined by the Real-time qPCR. The expression level was normalized to GAPDH expression and adjusted to the levels in naïve CD8+ T cells. Data shown are means±SD from 3 representative naïve CD8+ T cells. *p<0.05 and p<0.01, compared with the medium only group. (FIG. 13E) Senescent CD8+ T cells induced by Treg and tumor cells had strong suppressive activity on the proliferation of responding T cells. Cell treatment and procedure were the same as in FIG. 13A and FIG. 13B. Proliferation of co-cultured naïve CD4+ T cells stimulated by anti-CD3 antibody was determined by the [³H]-thymidine incorporation assay. Data shown are means±SD from representative of three independent experiments with similar results. p<0.01, compared with the medium only group. (FIGS. 13F-G) Increased senescent T cell populations were induced in both CD4+ and CD8+ T cells from different organs and tumor tissues in melanoma B16F0-bearing (in FIG. 13F) and breast cancer E0771-bearing (in FIG. 13G) mice. Tumor injections and experimental procedures were same as described in FIGS. 1A-J. Blood, LNs, SPs and tumor tissues were harvested and CD4+ and CD8+ T cells were purified for SA-β-gal staining. The SA-β-gal+ T cells were identified with dark blue granules as indicated by the arrows. Scale bar: 20 μm.

FIGS. 14A-G, related to FIGS. 2A-I-Senescent T cells induced by tumor cells did not significantly change the glucose metabolism. (FIG. 14A) Alterations of genes involved in TCA cycle were identified and ranked in senescent CD8+ T cells after co-culture with nTreg cells for different time points. Gene alterations were normalized to log 2 expression level. Cell treatment was same as described in FIG. 2A. Transcriptome analyses of nTreg-treated CD8+

T cells were performed using the Illumina whole-genome Human HT-12 BeadChips. (FIGS. 14B-C) Gene expression levels of glucose transporters (Glut1 and Glut3) and the key enzymes in glycolysis (HK2, GPI, PFK1, TPI, ENO1, PKM2 and LDHα) in senescent CD4+ (in FIG. 14B) and CD8+ (in FIG. 14C) T cells induced by MCF-7 tumor cells. Anti-CD3-activated naïve CD4+ and CD8+ T cells were co-cultured with breast cancer MCF-7 cells at a ratio of 1:1 for 1 day. The treated CD4+ and CD8+ T cells were then separated and cultured for additional 3 days, and glucose metabolism related gene expression levels were evaluated by the real-time qPCR. Expression levels of each gene were normalized to B-actin expression level and adjusted to the levels in respective naïve CD4+ or CD8+ T cells (served as 1). Data shown are means±SD from different independent donors. Each dot represents one individual donor. *p<0.05 and **p<0.01, compared with the medium group. (FIGS. 14D-E) CD8+ T cells purified from blood and TILs had higher gene expression levels of key enzymes in glycolysis in melanoma B16F0-bearing (in FIG. 14D) and breast cancer E0771-bearing (in FIG. 14E) mice than those from blood T cells in wild type mice. Tumor injections and experimental procedures were same as described in FIGS. 1A-J. Blood and tumor tissues were harvested and CD8+ T cells were purified. mRNA expression levels of glucose metabolism related genes in purified CD8+ T cells were evaluated by the real-time qPCR. Data shown are means±SD from 7 mice in each group. *p<0.05 and **p<0.01, compared with the blood T cells in WT mice. (FIGS. 14F-G) Blockage of glucose metabolism decreased cytokine productions in senescent T cells. Induction of senescent CD8+ T cells by nTreg cells (in FIG. 14F) or MCF-7 tumor cells (in FIG. 14G) was identical to the description in FIGS. 1A-J. The senescent CD8+ T cells were purified and cultured in the presence of glycolysis inhibitors 3-BrPA (30 μM) or 2-DG (2 mM) for an additional 1 day. mRNA expression levels of each cytokine were determined by the Real-time qPCR, and then were normalized to GAPDH expression and adjusted to the levels in senescent CD8+ T cells without inhibitor treatment. Data are means±SD from 3 independent experiments with similar results. *p<0.05 and **p<0.01, compared with the respective medium only group.

FIGS. 15A-E, related to FIGS. 3A-G-Lipid metabolism is disorder in senescent T cells in vivo in tumor-bearing mice. (FIG. 15A) Alterations of genes involved in the indicated lipid metabolism were identified and ranked in senescent CD8+ T cells after co-culture with nTreg cells for different time points. Gene alterations were normalized to log 2 expression level. Cell treatment was same as described in FIG. 2A Transcriptome analyses of nTreg-treated CD8+ T cells were performed using the Illumina whole-genome Human HT-12 BeadChips. (FIGS. 15B-C) CD4+ and CD8+ T cells purified from blood and TILs had altered gene expression levels of key enzymes in lipid metabolism in melanoma B16F0-bearing (in FIG. 15B) and breast cancer E0771-bearing (in FIG. 15C) mice compared with those from blood T cells in wild type mice. Tumor injections and experimental procedures were same as described in FIGS. 1A-J. Blood and tumor tissues were harvested and CD4+ and CD8+ T cells were purified. mRNA expression levels of lipid metabolism related genes in purified T cells were evaluated by the real-time qPCR. Data shown are means±SD from 7 mice each group. *p<0.05 and **p<0.01, compared with the blood CD4+ or CD8+ T cells in WT mice. (FIGS. 15D-E) CD4+ and CD8+ T cells purified from lymph nodes and spleens had similar gene expression profiles of key enzymes in lipid metabolism in melanoma B16F0-bearing (in FIG. 15D) and breast cancer E0771-bearing (in FIG. 15E) mice compared with respective T cells from wild-type mice. Tumor injections and experimental procedures were same as described in FIGS. 1A-J. Lymph nodes and spleens were harvested and CD4+ and CD8+ T cells were purified. mRNA expression levels of lipid metabolism related genes in purified T cells were evaluated by the real-time qPCR. Data shown are means±SD from 7 mice each group.

Figure 16:
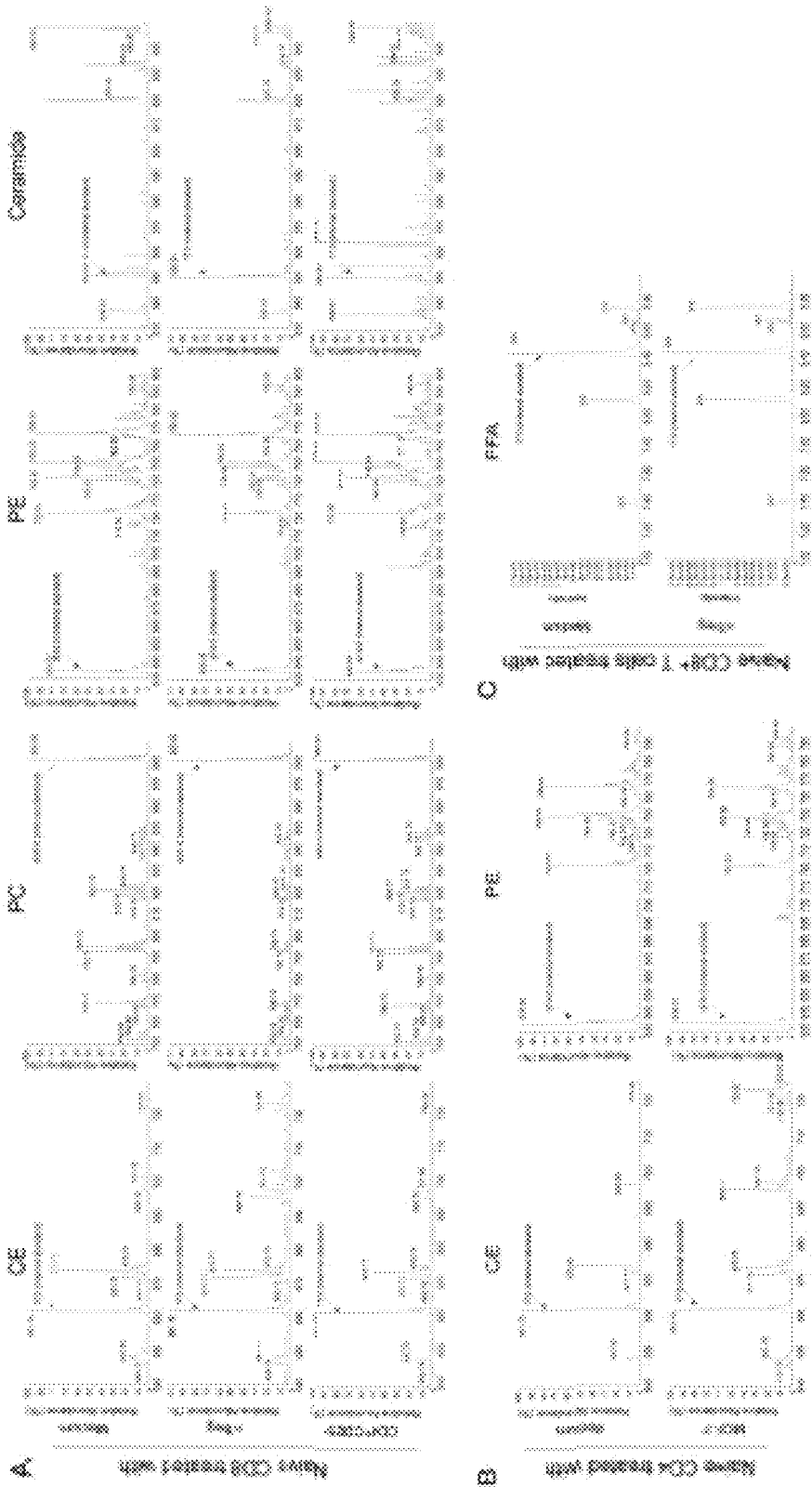

FIGS. 16A-C, related to FIGS. 4A-F-Lipidomic analysis of senescent T cells induced by Treg cells and tumor cells. (FIGS. 16A-B) Increased levels of multiple molecular species in CE and decreased multiple species in PC, PE and Ceramide in senescent T cells induced by nTreg cells (in FIG. 16A) and MCF-7 tumor cells (in FIG. 16B). T cell treatment and procedures are identical to the description in FIGS. 1A-J. Lipid extracts of T cells from different treatment groups were subjected to the ESI-MS/MS analysis. (FIG. 16C) FFA molecular species in naïve T cells and senescent T cells induced by nTreg were analyzed by the ESI-MS/MS analysis.

FIGS. 5A-K, related to FIGS. 5A-M-Accumulated LDs exist in senescent T cells. (FIG. 17A) Lipid metabolites themselves did not induce T cell senescence. Naïve CD4+ T cells were cultured in anti-CD3 coated (2 µg/ml) plate in the presence or absence of different dosages of the lipid components, including ceramide, PE, PS, aLPC, pLPC and LPC for 3 days. The treated naïve CD4+ T cells were then analyzed SA-β-gal expression. Data shown are means±SD from T cells derived from 3 independent experiments. (FIGS. 17B-C) LDs were accumulated in Treg-induced senescent T cells. Naïve CD4+ T cells were co-cultured with nTreg cells or control CD4+CD25-T cells at a ratio of 4:1 in the anti-CD3 (2 µg/ml) coated plates for 3 days. The treated T cells were purified and performed Bodipy 493/503 staining. Data shown in (FIG. 17B) and (FIG. 17C) are from the flow cytometry analysis and fluorescence images, respectively. Scale bar (in FIG. 17C): 20 µm. (FIG. 17D) LDs and cell cycle regulatory genes p21 and p53 were co-localized in Treg-induced senescent CD4+ T cells. Immunofluorescence double staining with antibodies against p21/p53 and with Bodipy 493/503 in the same slide from responder T cells treated with Treg or control CD4+CD25-effector T cells. Scale bar: 20 µm. (FIG. 17E) Lipid metabolites did not promote LD formation in T cells except ceramide and PS. Cell treatment and procedure were the same as in FIG. 17A. The treated naïve CD4+ T cells were then performed Oil-red O staining. p<0.01, compared with the medium only group. (FIGS. 17F-H) Kinetic gene expression levels of ACAT1 and ACAT2 in senescent T cells during senescence development. Naïve CD4+ or CD8+ T cells were co-cultured with nTreg cells (in FIG. 17F), or with MCF-7 breast cancer cells (in FIG. 17G and FIG. 17H) for different time points, respectively. The culture condition and ratios were same as described in FIGS. 1A-J. The co-cultured naïve CD4+ and CD8+ T cells were purified and mRNA expression levels of each gene were determined by the Real-time qPCR. The expression level was normalized to GAPDH expression and adjusted to the levels in naïve T cells. Data are means±SD from three independent experiments with similar results p<0.01, compared with the T cells in respective medium only group. (FIG. 17I) ACAT expression in T cells from melanoma B16F10-bearing and breast cancer E0771-bearing mice. Tumor injections and experimental procedures were described as in FIGS. 1A-J. Blood and tumor tissues were harvested and CD4+ and CD8+ T cells were purified. mRNA expression levels of ACAT1 and ACAT2 genes in purified T cells were evaluated by the real-time qPCR. Data shown are means±SD from 7 mice in each group. *p<0.05, compared with the blood T cells in WT mice. (FIGS. 17J-K) ACAT inhibitor avasimible did not promote T-cell senescence (in FIG. 17J) and LD formation (in FIG. 17K). Naïve CD4+ and CD8+ T cells were cultured with or without ACAT inhibitor avasimible in the anti-CD3 coated (2 µg/ml) plates for 3 days. The treated naïve CD4+ and CD8+ T cells were then performed SA-β-gal staining (in FIG. 17J) and Oil-red O staining (in FIG. 17K), respectively.

FIGS. 6A-D, related to FIGS. 6A-I-Increased expression of cPLA2α in senescent T cells. (FIGS. 18A-B) Increased both gene expression and protein levels of cPLA2α in T cells during the senescence induction. Naïve CD8+ and CD4+ T cells were co-cultured with nTreg cells or control CD4+CD25-T cells at a ratio of 4:1 in the presence of plate-bound anti-CD3 (2 µg/ml) for 3 days. The co-cultured naïve CD4+ and CD8+ T cells were purified and mRNA expression levels of cPLA2α gene were determined by the Real-time qPCR (in FIG. 18A). The expression level was normalized to GAPDH expression and adjusted to the levels in naïve T cells cultured in medium. In addition, protein expression levels of cPLA2α in treated T cells were analyzed by the flow cytometry analysis (in FIG. 18B). Data shown in (FIG. 18A) are means±SD from three independent experiments with similar results. *p<0.05 and **p<0.01, compared with the T cells in respective medium only group. (FIGS. 18C-D) cPLA2α inhibitor MAFP did not promote T-cell senescence (in FIG. 18C) and LD formation (in FIG. 18D). Naïve CD4+ and CD8+ T cells were cultured with or without cPLA2α inhibitor MAFP in the anti-CD3 coated (2 µg/ml) plates for 3 days. The treated CD4+ and CD8+ T cells were then performed SA-β-gal staining (in FIG. 18C) and Oil-red O staining (in FIG. 18D), respectively.

FIGS. 19A-F, related to FIGS. 7A-J-ATM-associated DNA damage response, and MAPK and STAT signaling are involved in T cell senescence mediated by Treg cells. (FIG. 19A) nTreg cell treatment increased phosphorylated activation of ATM-associated DNA damage responses in responder CD4+ T cells. Naïve CD4+ T cells were incubated alone or co-cultured with nTreg cells or CD4+CD25-T cells at a ratio of 4:1 in the presence of plate-bound anti-CD3 (2 µg/ml) for 5 days. p-H2AX, p-Chk2, p-53BP1 and p-ATM expression in treated naïve CD4+ T cells were analyzed by the flow cytometry. (FIG. 19B) Increased phosphorylated activation of P38, ERK, STAT1 and STAT3 signaling in senescent T cells induced by Treg cells. Cell treatment and culture condition were the same as in FIG. 19A. p-P38, p-ERK, p-STAT1 and p-STAT3 expression levels in treated naïve CD4+ T cells were analyzed by the flow cytometry. (FIG. 19C) Inhibition of ATM-associated DNA damage prevented phosphorylation of MAPKs and STAT1/STAT3 in Treg-induced senescent T cells. Naïve CD4+ T cells were pretreated with ATM inhibitor KU55933 (10 µM) for 24 hours and then co-cultured with nTreg cells at a ratio of 4:1 in anti-CD3-coated (2 µg/ml) plate for 3 days. Phosphorylation of p38, ERK, STAT1 and STAT3 in treated CD4+ T cells were analyzed by the flow cytometry. (FIG. 19D) Treatment with cPLA2α inhibitor MAFP could not block the activation of MAPK and STAT1/STAT3 signaling in senescent T cells mediated by Treg cells. Naïve CD4+ T cells were pretreated with cPLA2α inhibitor MAFP (5 µM) for 24 hours and then co-cultured with Treg cells at a ratio of 4:1 in anti-CD3 coated (2 µg/ml) plate for 3 days. Phosphorylation of p38, ERK, STAT1 and STAT3 in treated CD4+ T cells were analyzed by the flow cytometry. (FIGS. 19E-F) Treatments with the utilized concentrations of inhibitors for ATM, MAPK and STAT1/STAT3 signaling did not promote T cell senescence (in FIG. 19E) and LD formation (in FIG. 19F) in T cells. Naïve CD4+ and CD8+ T cells were cultured in the anti-CD3 coated (2 µg/ml) plates for 3 days in the presence or absence of the indicated inhibitors. The treated naïve CD8+ T cells were then purified and SA-β-gal+ and Oil red O+ T cell populations were determined. Data shown are means±SD from three independent experiments with similar results.

FIGS. 20A-E, related to FIGS. 7A-J-Blockages of MAPK and STAT1 signaling by specific inhibitors significantly prevent the Treg-induced up-regulation of CE and down-regulation of PC in senescent T cells. Naïve CD8+ T cells were pretreated with different inhibitors, including SB203580, U0126, MTA, and S3I-201 for 24 hours and then co-cultured with nTreg cells at a ratio of 4:1 in anti-CD3 coated (2 µg/ml) plates for 3 days. The treated naïve CD8+ T cells were then purified and the abundance of PC and CE species were evaluated by the ESI-MS/MS. Data shown are means±SD from 2 representative naïve CD8+ T cells. $*p<0.05$ and $**p<0.01$, compared with the medium only group.

FIGS. 21A-C, related to FIGS. 8A-K-Inhibition of cPLA2α with MAFP reprograms T cell lipid metabolism and enhances anti-tumor immunity. (FIG. 21A) MAFP treatment did not directly affect B16F10 tumor growth in C57BL/6 mice. Mouse B1610 tumor cells (2× 105) were subcutaneously injected into C57BL/6 mice. MAFP (7.5 mg kg−1/mouse) was injected intraperitoneally into the mice at day 7, 10, 13, or 16 days after tumor challenge. Tumor volumes were measured and presented as means±SD (n=6 mice per group). (FIGS. 21B-C) Inhibition of cPLA2α prevented up-regulated inflammation cytokines and altered lipid-associated enzymes in senescent Pmel-1 T cells from blood and TILs. Cell treatment and adoptive transfer procedure were identical to the FIG. 8A. The transferred Peml-1 T cells were isolated and recovered from blood and tumor for subsequent real-time qPCR. Expression levels of each gene were normalized to β-actin expression level and adjusted to the levels in T cells of the group without MAFP treatment (served as 1). Data shown are means±SD from 6 mice per group. $*p<0.05$ and $**p<0.01$, compared with the group of T cells without MAFP treatment.

Figure 22:
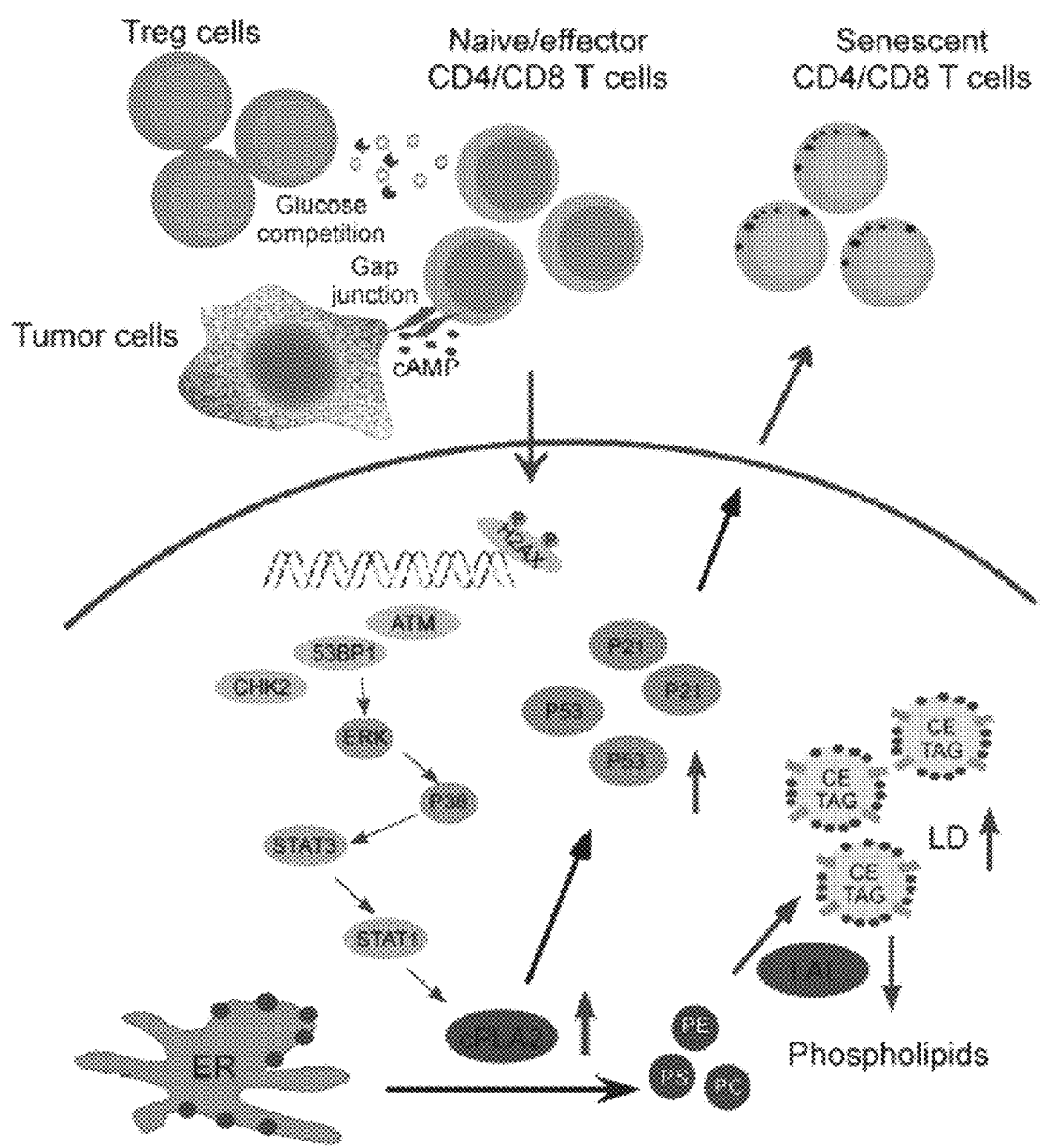

FIG. 22, related to FIGS. 1A-8K-Diagram of the molecular processes responsible for senescence induction in responder T cells mediated by human Treg and tumor cells. Human Treg cells or tumor cells initiate the ATM-associated DNA damge response through glucose competition or tumor-derived endogenous cyclic adenosine monophosphate (cAMP), respectively. DNA damage signaling then cooperates with MAPKs and STAT1/3 signaling to promote cPLA2α expression and activity, resulting in the lipid metabolism disorder (LD accumulation and altered phospholipids) and cell senescence in responder T cells.

DETAILED DESCRIPTION

T cell functional state is a key determinant for effective anti-tumor immunity and immunotherapy. Cellular metabolism controls T cell differentiation, survival and effector functions. Here, the inventors report that development of T cell senescence driven by both malignant tumor cells and regulatory T (Treg) cells is a general feature in cancers. Senescent T cells have active glucose metabolism but exhibit unbalanced lipid metabolism, resulting in changes of expression of lipid metabolic enzymes and lipid species, and accumulation of lipid droplets (LDs). The inventors determined that elevated group IVA phospholipase $A_2$ (cPLA2α)

activity is responsible for the altered lipid metabolism and senescence induction in T cells mediated by Treg and tumor cells, and involves MAPK and STAT signaling. Moreover, they show that inhibition of cPLA2α can reprogram T cell lipid metabolism and prevent T cell senescence, resulting in enhanced anti-tumor immunity and immunotherapy efficacy in vivo in adoptive transfer T cell therapy tumor models. These studies identify novel mechanistic links between T cell senescence and regulation of lipid metabolism in the tumor microenvironment and provide a new target for tumor immunotherapy. These and other aspects of the disclosure are set out in detail below.

I. GROUP IVA PHOSPHOLIPASE $A_2$ (cPLA2α) AND INHIBITORS THEREOF

A. cPLA2α

Group IVA Phospholipase A2 (cPLA2α), also known as cytosolic phospholipase A2, is an enzyme that in humans is encoded by the PLA2G4A gene. The enzyme catalyzes the hydrolysis of membrane phospholipids to release arachidonic acid which is subsequently metabolized into eicosanoids. Eicosanoids, including prostaglandins and leukotrienes, are lipid-based cellular hormones that regulate hemodynamics, inflammatory responses, and other intracellular pathways. The hydrolysis reaction also produces lysophospholipids that are converted into platelet-activating factor. The enzyme is activated by increased intracellular $Ca^{2+}$-levels and phosphorylation, resulting in its translocation from the cytosol and nucleus to perinuclear membrane vesicles.

cPLA2α has been shown to interact with HTATIP. Mutations in this gene have been associated with multifocal stenosing ulceration of the small intestine. Human RNA sequences for cPLA2α include NM 00131193 and NM 024420. Human protein sequences for cPLA2α include NP 001298122 and NP 077734. All four of these sequences are hereby incorporated by reference.

B. Pharmacologic Inhibitors

Methoxy arachidonyl fluorophosphonate, commonly referred as MAFP, is an irreversible active site-directed enzyme inhibitor that inhibits nearly all serine hydrolases and serine proteases, including cPLA2α. It inhibits phospholipase $A_2$ and fatty acid amide hydrolase with special potency, displaying IC50 values in the low-nanomolar range. In addition, it binds to the $CB_1$ receptor in rat brain membrane preparations ($IC_{50}$=20 nM) but does not appear to agonize or antagonize the receptor. See Gubern et al., *J. Biol. Chem.* 283 (41): 27369-82 (2008).

Other inhibitors include AACOCF3 (ATK) (Chuang et al., *J. Neuroinflammation* 12:199, 2015), Pyrrophenone (Malada-Edelstein et al., *J. Neuroinflammation* 14 (1): 33, 2017), PLA-695 (Thotala et al., *PLOS One* 8 (7): e69688, 2013), and CDIBA (Linkous et al., *J. Nat'l Cancer Inst.* 102 (18): 1398-412, 2010).

C. Oligonucleotide Inhibitors

Oligonucleotide inhibitors are generally those that hybridize through sequence identity to target nucleic acids—either genomic DNA or mRNA. The oligonucleotide or oligonucleotide analog may therefore comprise DNA nucleobases, RNA nucleobases or a mixture of DNA and RNA nucleobases. The oligonucleotide or oligonucleotide analog may single- or double-stranded RNA molecule, such as a siRNA or an shRNA. The length of the oligonucleotide may be 10-50 bases, and more specifically 13-30 bases, such as 13, 14, 15, 16, 17, 18, 19, 20, 21, 22, 23, 24, 25, 26, 27, 28, 29, or 30 nucleobases. The siRNA may have strands of identical lengths, or different lengths. The siRNA may comprise one strand of 14-19 nucleotides in length and a second strand of 19-22 nucleotides in length. The siRNA may comprise at least one modified nucleotide, such as 2'-O-methyl-ribonucleotides, 2'-fluoro-ribonucleotides, 5'-vinylphosphonate, phosphorothioate linkage, or lipid conjugation. The siRNA may have every ribonucleotide modified, such as with 2'-O-methyl- and 2'-fluoro-ribonucleotides. The oligonucleotide or oligonucleotide analog may be a single-stranded DNA or RNA, such as an antisense molecule or a single-stranded RNA-like antisense molecule.

Commercially available equipment routinely used for the support-media-based synthesis of oligomeric compounds and related compounds is sold by several vendors including, for example, Biolytic (Fremont, CA), Bioautomation (Irving, TX), General Electric, as well as others. Suitable solid phase techniques, including automated synthesis techniques, are described in Scozzari and Capaldi, "Oligonucleotide Manufacturing and Analytic Processes for 2'-O-(2-methoxy-ethyl-Modified Oligonucleotides" in Crooke, S. T. (ed.) Antisense Drug Technology: Principles, Strategies, and Applications, Second Edition (2007).

1. RNA Oligonucleotides

The oligonucleotide agents of the present disclosure bind to target sequences in the cPLA2α gene or mRNA. The oligonucleotide or oligonucleotide analog may, in particular, be RNA and include one or more modified and/or non-natural nucleobases. The oligonucleotide or oligonucleotide analog may contain DNA as well as RNA nucleobases, such as terminal thymidine residues. The RNA may be double-stranded or single-stranded.

While ds-RNAs have been employed for some time, ss-RNAs are a new approach to gene silencing in which single-stranded RNA is chemically modified to enable it to be stable in vivo while retaining the ability to engage the RNAi machinery (Lima et al., 2012). The inventors have previously shown that anti-repeat ss-siRNAs can be active towards inhibiting expression of repeat containing genes in cell culture and the central nervous system of HD model mice. ss-siRNAs are attractive candidates for testing because, in contrast to duplex RNA, they are single-stranded and may possess better biodistribution and activity in vivo. Thus, the inventors contemplate the application of ss-siRNAs as CAG/CUG repeat targeting agents.

Another modification of oligonucleotides involved their conjugation to lipids, which are commonly used for modifying oligonucleotides. From a therapeutic point of view, lipid-oligonucleotide conjugates (LOCs) have emerged as an alternative to cationic particles in order to reduce toxicity and improve biodistribution. Oligonucleotide entry into cells normally takes place through receptor-mediated endocytosis by binding with high affinity to cell surface receptors. However, this uptake efficiency could change when modified oligonucleotides are internalized into the cell, but the use of biocleavable lipids can help mitigate any such effects if observed. Many synthetic strategies have been reported in recent years for obtaining oligonucleotides covalently linked to a variety of lipophilic moieties. The conjugation of these units can occur at either the nucleoside or the nucleotide level, giving rise to the corresponding amphiphilic-based compounds. Other strategies have incorporated lipid moieties through a phosphodiester bond in order to obtain LOC conjugates with better pharmacokinetic behaviors and improved cellular uptake. In general, the oligonucleotide ends (3'- and 5'-termini) are the most accessible conjugation sites for lipophilic units.

The use of lipid-containing formulations and lipid-based conjugates may increase uptake in the eye after administration of eye drops. Lipid conjugates or other types of conjugates may improve binding to particular cell types within the eye. Embodiments include such formulations and conjugates.

In the case of conjugates, a chemical moiety may be included on one end, on both ends, or on one or more central positions within an ASO or siRNA. In another embodiment, a chemical moiety can be conjugated to a complementary oligonucleotide that binds to the ASO rather than to the ASO itself (Nishina et al., 2015). If the oligonucleotide is a double-stranded RNA, the conjugate may be placed on either strand. In a preferred embodiment the conjugate is placed on the sense strand of double-stranded RNA.

Said chemical moiety may serve to improve cellular uptake or pharmacokinetic parameters or may improve uptake by a particular cell type (Winkler, 2013). For example, this disclosure includes conjugates that show improved uptake in corneal endothelial cells. This in turn allows delivery to the cornea by administration of topical eyedrops, intracameral injection, or by intravitreal injection.

In one embodiment of the disclosure, the conjugated moiety is a lipid or other hydrophobic group. In other embodiments, the moiety comprises a peptide, carbohydrate or nucleic acid. Many moieties suitable for use in oligonucleotide conjugates are well known in the art. In some embodiments, the conjugated moiety may improve pharmacokinetics and uptake by increasing hydrophobicity. In other embodiments, the conjugated moiety may improve pharmacokinetics and uptake by interacting with specific proteins.

Conjugating a lipid group on one end of an oligonucleotide can lead to the assembly of micellar structures. In some cases, these structures can be sufficient to trigger enhanced or optimal uptake. In other cases, the use of compounds containing multiple conjugate groups may be preferred, as this approach can be used to display groups in a way that increases binding to cells or proteins of interest, pharmacokinetic properties, and/or potency.

In some cases, the conjugated moiety can be attached to the oligonucleotide through a linkage designed to cleave inside cells, such as a reducible linkage, a nuclease-sensitive linkage, or a protease-sensitive linkage. In other embodiments, the conjugated moiety can be attached to the non-active strand of a duplex (such as the sense strand of a siRNA or a complementary RNA strand). In still other embodiments, the conjugate may be permanently attached to the active strand.

2. RNAi

RNA interference (also referred to as "RNA-mediated interference" or RNAi) is a mechanism by which gene expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity. Activation of these mechanisms targets mature, dsRNA-complementary mRNA for destruction. RNAi offers major experimental advantages for study of gene function. These advantages include a very high specificity, ease of movement across cell membranes, and prolonged down-regulation of the targeted gene. It is generally accepted that RNAi acts post-transcriptionally, targeting RNA transcripts for degradation. It appears that both nuclear and cytoplasmic RNA can be targeted.

siRNAs must be designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 20 to 23 nucleotides in length are most effective. This length reflects the lengths of digestion products resulting from the processing of much longer RNAs as described above. siRNA and double-stranded RNA have been described in U.S. Pat. Nos. 6,506,559 and 6,573,099, as well as in U.S. Patent Applications 2003/0051263, 2003/0055020, 2004/0265839, 2002/0168707, 2003/0159161, and 2004/0064842, all of which are herein incorporated by reference in their entirety.

Several further modifications to siRNA sequences have been suggested in order to alter their stability or improve their effectiveness. It has been suggested that synthetic complementary 21-mer RNAs having di-nucleotide overhangs (i.e., 19 complementary nucleotides+3' non-complementary dimers) may provide the greatest level of suppression. These protocols may use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang. More recently, it has been suggested that it may be preferable for the overhangs to use 2'-OMe-uridine (2'-OMe-U). It may also be preferable to use a single 3' overhang in the antisense strand and have no overhang in the sense strand.

Short hairpin RNA (shRNA) is a sequence of RNA that makes a tight hairpin turn that can be used to silence gene expression. shRNA is transcribed by RNA polymerase III. shRNA production in a mammalian cell can sometimes cause the cell to mount an interferon response as the cell seeks to defend itself from what it perceives as viral attack. Researchers have examined the importance of stem and loop length, sequence specificity, and presence of overhangs in determining shRNA activity. The authors found some interesting results. For example, they showed that the length of the stem and loop of functional shRNAs could vary. Stem lengths could range anywhere from 25 to 29 nt and loop size could range between 4 to 23 nt without affecting silencing activity. Presence of G-U mismatches between the 2 strands of the shRNA stem did not lead to a decrease in potency. Complementarity between the portion of the stem that binds to the target mRNA (antisense strand) and the mRNA, on the other hand, was shown to be critical. Single base mismatches between the antisense strand of the stem and the mRNA abolished silencing. It has been reported that presence of 2 nt 3'-overhangs is critical for siRNA activity. Presence of overhangs on shRNAs, however, did not seem to be important. Some of the functional shRNAs that were either chemically synthesized or in vitro transcribed, for example, did not have predicted 3' overhangs.

dsRNA can be synthesized using well-described methods. Briefly, sense and antisense RNA are synthesized from DNA templates using T7 polymerase (MEGAscript, Ambion). After the synthesis is complete, the DNA template is digested with DNaseI and RNA purified by phenol/chloroform extraction and isopropanol precipitation. RNA size, purity and integrity are assayed on denaturing agarose gels. Sense and antisense RNA are diluted in potassium citrate buffer and annealed at 80° C. for 3 min to form dsRNA. As with the construction of DNA template libraries, automated procedures may be used to aid this time intensive procedure. The sum of the individual dsRNA species is designated as a "dsRNA library."

The making of siRNAs has been mainly through direct chemical synthesis; through processing of longer, double-stranded RNAs through exposure to *Drosophila* embryo lysates; or through an in vitro system derived from S2 cells. Use of cell lysates or in vitro processing may further involve the subsequent isolation of the short, 21-23 nucleotide siRNAs from the lysate, etc., making the process somewhat cumbersome and expensive. Chemical synthesis proceeds by making two single-stranded RNA-oligomers followed by the annealing of the two single-stranded oligomers into a double-stranded RNA.

WO 99/32619 and WO 01/68836 suggest that RNA for use in siRNA may be chemically or enzymatically synthesized. Both of these texts are incorporated herein in their entirety by reference. The enzymatic synthesis contemplated in these references is by a cellular RNA polymerase or a bacteriophage RNA polymerase (e.g., T3, T7, SP6) via the use and production of an expression construct as is known in the art. For example, see U.S. Pat. No. 5,795,715. The contemplated constructs provide templates that produce RNAs that contain nucleotide sequences identical to a portion of the target gene. The length of identical sequences provided by these references is at least 25 bases and may be as many as 400 or more bases in length. An important aspect of this reference is that the authors contemplate digesting longer dsRNAs to 21-25mer lengths with the endogenous nuclease complex that converts long dsRNAs to siRNAs in vivo. They do not describe or present data for synthesizing and using in vitro transcribed 21-25mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Preferably, single-stranded RNA is enzymatically synthesized from the PCR products of a DNA template, preferably a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates are preferably attached to a solid surface. After transcription with RNA polymerase, the resulting dsRNA fragments may be used for detecting and/or assaying nucleic acid target sequences.

Several groups have developed expression vectors that continually express siRNAs in stably transfected mammalian cells. Some of these plasmids are engineered to express shRNAs lacking poly (A) tails. Transcription of shRNAs is initiated at a polymerase III (pol III) promoter and is believed to be terminated at position 2 of a 4-5-thymine transcription termination site. shRNAs are thought to fold into a stem-loop structure with 3' UU-overhangs. Subsequently, the ends of these shRNAs are processed, converting the shRNAs into ~21 nt siRNA-like molecules. The siRNA-like molecules can, in turn, bring about gene-specific silencing in the transfected mammalian cells.

More generally, most any oligo- or polynucleotide may be made by any technique known to one of ordinary skill in the art, such as chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described in U.S. Pat. No. 5,705,629, each incorporated herein by reference. In the methods of the present disclosure, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria.

3. Antisense

In some embodiments, the nucleic acid comprises one or more antisense oligonucleotide (ASO) segments which inhibit(s) expression of a gene or gene product. Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G: C) and adenine paired with either thymine (A: T) or uracil (A: U). Inclusion of less common bases such as inosine, 5-methylcytosine, 6-methyladenine, hypoxanthine and others in hybridizing sequences does not interfere with pairing.

ASOs will not require the RNAi machinery and are a different strategy for silencing gene expression. The inventors contemplate ASOs substituted with locked nucleic acids (LNAs). LNA nucleotides are constrained by a bond between the 2' and 4' positions of the ribose ring. This constraint "locks" the nucleotide into a position that is ideal for base-pairing and the introduction of a handful of LNA nucleotides into an ASO can tailor the affinity of an ASO for optimal success in many applications. Other modifications may be used to tailor ASO affinity for desired applications, including 2'-O-methoxyethyl RNA and tricycloDNA. A person of skill in the art will understand additional modifications that can be used to tailor ASO binding affinity and nucleobase stability. Thus, the inventors also contemplate the application of ASOs as CUG repeat containing targeting agents.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs may include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

4. CRISPR-Cas9

CRISPRs (clustered regularly interspaced short palindromic repeats) are DNA loci containing short repetitions of base sequences. Each repetition is followed by short segments of "spacer DNA" from previous exposures to a virus. CRISPRs are found in approximately 40% of sequenced eubacteria genomes and 90% of sequenced archaea. CRISPRs are often associated with Cas genes that code for proteins related to CRISPRs. The CRISPR/Cas system is a prokaryotic immune system that confers resistance to foreign genetic elements such as plasmids and phages and provides a form of acquired immunity. CRISPR spacers recognize and silence these exogenous genetic elements like RNAi in eukaryotic organisms.

CRISPR was first shown to work as a genome engineering/editing tool in human cell culture by 2012. It has since been used in a wide range of organisms including baker's yeast (S. cerevisiae), zebra fish, nematodes (C. elegans), plants, mice, and several other organisms. Additionally CRISPR has been modified to make programmable transcription factors that allow scientists to target and activate or silence specific genes. Libraries of tens of thousands of guide RNAs are now available.

The first evidence that CRISPR can reverse disease symptoms in living animals was demonstrated in March 2014, when MIT researchers cured mice of a rare liver disorder. Since 2012, the CRISPR/Cas system has been used for gene editing (silencing, enhancing or changing specific genes) that even works in eukaryotes like mice and primates. By inserting a plasmid containing cas genes and specifically designed CRISPRs, an organism's genome can be cut at any desired location.

CRISPR repeats range in size from 24 to 48 base pairs. They usually show some dyad symmetry, implying the formation of a secondary structure such as a hairpin, but are not truly palindromic. Repeats are separated by spacers of similar length. Some CRISPR spacer sequences exactly match sequences from plasmids and phages, although some spacers match the prokaryote's genome (self-targeting spacers). New spacers can be added rapidly in response to phage infection.

CRISPR-associated (cas) genes are often associated with CRISPR repeat-spacer arrays. As of 2013, more than forty different Cas protein families had been described. Of these protein families, Cas1 appears to be ubiquitous among different CRISPR/Cas systems. Particular combinations of cas genes and repeat structures have been used to define 8 CRISPR subtypes (E coli, Ypest, Nmeni, Dvulg, Tneap, Hmari, Apern, and Mtube), some of which are associated with an additional gene module encoding repeat-associated mysterious proteins (RAMPs). More than one CRISPR subtype may occur in a single genome. The sporadic distribution of the CRISPR/Cas subtypes suggests that the system is subject to horizontal gene transfer during microbial evolution.

Exogenous DNA is apparently processed by proteins encoded by Cas genes into small elements (~30 base pairs in length), which are then somehow inserted into the CRISPR locus near the leader sequence. RNAs from the CRISPR loci are constitutively expressed and are processed by Cas proteins to small RNAs composed of individual, exogenously-derived sequence elements with a flanking repeat sequence. The RNAs guide other Cas proteins to silence exogenous genetic elements at the RNA or DNA level. Evidence suggests functional diversity among CRISPR subtypes. The Cse (Cas subtype E coli) proteins (called CasA-E in E. coli) form a functional complex, Cascade, that processes CRISPR RNA transcripts into spacer-repeat units that Cascade retains. In other prokaryotes, Cas6 processes the CRISPR transcripts. Interestingly, CRISPR-based phage inactivation in E. coli requires Cascade and Cas3, but not Cas1 and Cas2. The Cmr (Cas RAMP module) proteins found in Pyrococcus furiosus and other prokaryotes form a functional complex with small CRISPR RNAs that recognizes and cleaves complementary target RNAs. RNA-guided CRISPR enzymes are classified as type V restriction enzymes.

Cas9 is a nuclease, an enzyme specialized for cutting DNA, with two active cutting sites, one for each strand of the double helix. The team demonstrated that they could disable one or both sites while preserving Cas9's ability to home located its target DNA. Researchers have combined tracrRNA and spacer RNA into a "single-guide RNA" molecule that, mixed with Cas9, could find and cut the correct DNA targets. Others have proposed that such synthetic guide RNAs might be able to be used for gene editing.

Cas9 proteins are highly enriched in pathogenic and commensal bacteria. CRISPR/Cas-mediated gene regulation may contribute to the regulation of endogenous bacterial genes, particularly during bacterial interaction with eukaryotic hosts. For example, Cas protein Cas9 of *Francisella novicida* uses a unique, small, CRISPR/Cas-associated RNA (scaRNA) to repress an endogenous transcript encoding a bacterial lipoprotein that is critical for *F. novicida* to dampen host response and promote virulence. Wang et al. (2013) showed that coinjection of Cas9 mRNA and sgRNAs into the germline (zygotes) generated nice with mutations. Delivery of Cas9 DNA sequences also is contemplated.

See also U.S. Patent Publication 2014/0068797, which is incorporated by reference in its entirety.

Clustered Regularly Interspaced Short Palindromic Repeats from *Prevotella* and *Francisella* 1 or CRISPR/Cpf1 is a DNA-editing technology analogous to the CRISPR/Cas9 system. Cpf1 is an RNA-guided endonuclease of a class II CRISPR/Cas system. This acquired immune mechanism is found in *Prevotella* and *Francisella* bacteria. It prevents genetic damage from viruses. Cpf1 genes are associated with the CRISPR locus, coding for an endonuclease that use a guide RNA to find and cleave viral DNA. Cpf1 is a smaller and simpler endonuclease than Cas9, overcoming some of the CRISPR/Cas9 system limitations. CRISPR/Cpf1 could have multiple applications, including treatment of genetic illnesses and degenerative conditions.

CRISPR/Cpf1 was found by searching a published database of bacterial genetic sequences for promising bits of DNA. Its identification through bioinformatics as a CRISPR system protein, its naming, and a hidden Markov model (HMM) for its detection were provided in 2012 in a release of the TIGRFAMs database of protein families. Cpf1 appears in many bacterial species. The ultimate Cpf1 endonuclease that was developed into a tool for genome editing was taken from one of the first 16 species known to harbor it. Two candidate enzymes from Acidaminococcus and Lachnospiraceae display efficient genome-editing activity in human cells.

A smaller version of Cas9 from the bacterium *Staphylococcus aureus* is a potential alternative to Cpf1

The systems CRISPR/Cas are separated into three classes. Class 1 uses several Cas proteins together with the CRISPR RNAs (crRNA) to build a functional endonuclease. Class 2 CRISPR systems use a single Cas protein with a crRNA. Cpf1 has been recently identified as a Class II, Type V CRISPR/Cas systems containing a 1,300 amino acid protein.

The Cpf1 locus contains a mixed alpha/beta domain, a RuvC-I followed by a helical region, a RuvC-II and a zinc finger-like domain. The Cpf1 protein has a RuvC-like endonuclease domain that is similar to the RuvC domain of Cas9. Furthermore, Cpf1 does not have a HNH endonuclease domain, and the N-terminal of Cpf1 does not have the alpha-helical recognition lobe of Cas9.

Cpf1 CRISPR-Cas domain architecture shows that Cpf1 is functionally unique, being classified as Class 2, type V CRISPR system. The Cpf1 loci encode Cas1, Cas2 and Cas4 proteins more similar to types I and III than from type II systems. Database searches suggest the abundance of Cpf1-family proteins in many bacterial species.

Functional Cpf1 doesn't need the tracrRNA, therefore, only crRNA is required. This benefits genome editing because Cpf1 is not only smaller than Cas9, but also it has a smaller sgRNA molecule (proximately half as many nucleotides as Cas9).

The Cpf1-crRNA complex cleaves target DNA or RNA by identification of a protospacer adjacent motif 5'-YTN-3' (where "Y" is a pyrimidine and "N" is any nucleobase) or 5'-TTN-3', in contrast to the G-rich PAM targeted by Cas9.

After identification of PAM, Cpf1 introduces a sticky-end-like DNA double-stranded break of 4 or 5 nucleotides overhang.

The CRISPR/Cpf1 system consist of a Cpf1 enzyme and a guide RNA that finds and positions the complex at the correct spot on the double helix to cleave target DNA. CRISPR/Cpf1 systems activity has three stages:

Adaptation, during which Cas1 and Cas2 proteins facilitate the adaptation of small fragments of DNA into the CRISPR array;

Formation of crRNAs: processing of pre-cr-RNAs producing of mature crRNAs to guide the Cas protein; and Interference, in which the Cpf1 is bound to a crRNA to form a binary complex to identify and cleave a target DNA sequence.

As an RNA guided protein, Cas9 requires a short RNA to direct the recognition of DNA targets. Though Cas9 preferentially interrogates DNA sequences containing a PAM sequence NGG it can bind here without a protospacer target. However, the Cas9-sgRNA complex requires a close match to the sgRNA to create a double strand break. CRISPR sequences in bacteria are expressed in multiple RNAs and then processed to create guide strands for RNA. Because Eukaryotic systems lack some of the proteins required to process CRISPR RNAs the synthetic construct sgRNA was created to combine the essential pieces of RNA for Cas9 targeting into a single RNA expressed with the RNA polymerase type III promoter U6. Synthetic sgRNAs are slightly over 100 bp at the minimum length and contain a portion which is targets the 20 protospacer nucleotides immediately preceding the PAM sequence NGG; sgRNAs do not contain a PAM sequence.

5. Modified Nucleotides

In certain embodiments, oligonucleotides of the disclosure comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In particular embodiments, nucleic acids may be modified with a 5'-vinylphosphonate to increase the stability of the nucleic acid and improve tissue accumulation. In certain embodiments, substituted sugars comprise more than one non-bridging sugar substituent, for example, T-F-5'-methyl sugar moieties (see, e.g., PCT International Application WO 2008/101157, for additional 5',2'-bis substituted sugar moieties and nucleosides).

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2'; and 4'-CH$_2$—C(=CH$_2$)-2' and analogs thereof (see, PCT International Application WO 2008/154401, published on Dec. 8, 2008).

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, a-L-methyleneoxy (4'-CH$_2$—O-2') bicyclic nucleosides have been incorporated into antisense oligonucleotides that showed antisense activity.

In certain embodiments, substituted sugar moieties comprise one or more non-bridging sugar substituent and one or more bridging sugar substituent (e.g., 5'-substituted and 4'-2' bridged sugars; PCT International Application WO 2007/134181, published on Nov. 22, 2007, wherein LNA is substituted with, for example, a 5'-methyl or a 5'-vinyl group). For example, in certain embodiments, the nucleosides may contain two bridging substitutents, forming a tricyclic structure as found in tricycloDNA (Steffens and Leurmann, 1997). In other embodiments, a constrained structure may also include the phosphorus atom of the internucleotide linkage.

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfur atom and a substitution at the 2'-position (see, e.g., published U.S. Patent Publication No. 20050130923, published on Jun. 16, 2005) and/or the 5' position. By way of additional example, carbocyclic bicyclic nucleosides having a 4'-2' bridge have been described (see, e.g., Freier et al., Nucleic Acids Research, 1997, 25 (22), 4429-4443 and Albaek et al., J. Org. Chem., 2006, 71, 7731-7740).

Combinations of modifications are also provided without limitation, such as 2'-F-5'-methyl substituted nucleosides (see PCT International Application WO2008/101157 Published on Aug. 21, 2008 for other disclosed 5',2'-bis substituted nucleosides) and replacement of the ribosyl ring oxygen atom with S and further substitution at the 2'-position (see U.S. Patent Publication US20050130923, published on Jun. 16, 2005) or alternatively 5'-substitution of a bicyclic nucleic acid (see PCT International Application WO2007/ 134181, published on Nov. 22, 2007 wherein a 4'-$CH_2$—O— 2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., J. Am. Chem. Soc. 2007, 129 (26), 8362-8379).

In certain embodiments, nucleosides of the present disclosure comprise one or more unmodified nucleobases. In other embodiments, nucleosides of the present disclosure comprise one or more modified nucleobases. In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl $CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b] [1,4]benzoxazin-2 (3H)-one), phenothiazine cytidine (1H-pyrimido[5,4-b][1,4]benzothiazin-2 (3H)-one), G-clamps such as a substituted phenoxazine cytidine (e.g., 9-(2-aminoethoxy)-H-pyrimido[5,4-13][1,4]benzoxazin-2 (3H)-one), carbazole cytidine (2H-pyrimido[4,5-b]indol-2-one), pyridoindole cytidine (H-pyrido[3',2': 4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, Kroschwitz, J. I., Ed., John Wiley & Sons, 1990, 858-859; those disclosed by Englisch et al., Angewandte Chemie, International Edition, 1991, 30, 613; and those disclosed by Sanghvi, Y. S., Chapter 15, Antisense Research and Applications, Crooke, S. T. and Lebleu, B., Eds., CRC Press, 1993, 273-288.

Representative U.S. Patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, each of which is herein incorporated by reference in its entirety.

In certain embodiments, the present disclosure provides oligonucleotides comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P═O), phosphotriesters, methylphosphonates, methylenephosphonates, vinylphosphonates, phosphonoacetates, thiophosphonoacetates, phosphoramidates, and phosphorothioates (P═S). Representative non-phosphorus containing internucleoside linking groups include, but are not limited to, amide, triazole, methylenemethylimino (—$CH_2$—$N(CH_3)$—O—$CH_2$—), thiodiester (—O—C(O)—S—), thionocarbamate (—O—C(O)(NH)— S—); siloxane (—O—$Si(H)_2$—O—); and N,N'-dimethylhydrazine (—$CH_2$—$N(CH_3)$—$N(CH_3)$—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids, etc. Included in the antisense compounds provided herein are all such possible isomers, as well as their racemic and optically pure forms.

Additional modifications may also be made at other positions on the oligonucleotide, particularly the 3' position of the sugar on the 3' terminal nucleotide and the 5' position of 5' terminal nucleotide. For example, one additional modification of the ligand conjugated oligonucleotides of the present disclosure involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553), cholic acid (Manoharan et al., Bioorg. Med. Chem. Lett., 1994, 4, 1053), a thioether, e.g., hexyl-5-tritylthiol (Manoharan et al., Ann. N.Y. Acad. Sci., 1992, 660, 306; Manoharan et al., Bioorg. Med. Chem. Let., 1993, 3, 2765), a thiocholesterol (Oberhauser et al., Nucl. Acids Res., 1992, 20, 533), an aliphatic chain, e.g., dodecandiol or undecyl residues (Saison-Behmoaras et al., EMBO J., 1991, 10, 111; Kabanov et al., FEBS Lett., 1990, 259, 327; Svinarchuk et al., Biochimie, 1993, 75, 49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), a polyamine or a polyethylene glycol chain (Manoharan et al., Nucleosides & Nucleotides, 1995, 14, 969), or adamantane acetic acid (Manoharan et al., Tetrahedron Lett., 1995, 36, 3651), a palmityl moiety (Mishra et al., Biochim. Biophys. Acta, 1995, 1264, 229), or an octadecylamine or hexylaminocarbonyl-oxycholesterol moiety (Crooke et al., J. Pharmacol. Exp. Ther., 1996, 277, 923).

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241; 5,391,723; 5,416,203; 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned, and each of which is herein incorporated by reference.

II. HYPERPROLIFERATIVE DISEASES

While hyperproliferative diseases can be associated with any disease which causes a cell to begin to reproduce uncontrollably, the prototypical example is cancer. One of the key elements of cancer is that the cell's normal apoptotic cycle is interrupted and thus agents that interrupt the growth of the cells are important as therapeutic agents for treating these diseases. In this disclosure, a cPLA2α inhibitor may be used to treat a variety of types of cancers. In various aspects, it is anticipated that the cPLA2α inhibitor of the present disclosure may be used to treat virtually any malignancy.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

III. THERAPIES AND DIAGNOSTICS

A. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals. One will generally desire to employ appropriate salts, buffers, and lipids to render delivery of the oligonucleotides to allow for uptake by target cells. Such methods an compositions are well known in the art, for example, as disclosed in U.S. Pat. Nos. 6,747,014 and 6,753,423, incorporated by reference herein. Compositions of the present disclosure comprise an effective amount of the oligonucleotide to cells, dissolved or dispersed in a pharmaceutically acceptable carrier or medium.

The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents, liposomes, cationic lipid formulations, microbubble nanoparticles, and the like. Except insofar as any conventional media or agent is incompatible with the vectors or cells of the present disclosure, its use in therapeutic compositions is contemplated. Supplementary active ingredients also can be incorporated into the compositions.

The active compositions of the present disclosure may include classic pharmaceutical preparations. Administration of these compositions according to the present disclosure will be via any common route so long as the target tissue is available via that route. Ocular administration includes topical eye drops, intracameral injection, or intravitreal injection to target the cornea including corneal endothelial cell layer. Alternatively, administration may be oral, nasal, buccal, or topical. Alternatively, administration may be by intradermal, subcutaneous, intramuscular, intraperitoneal or intravenous injection, or introduction into the CNS, such as into spinal fluid. Such compositions would normally be administered as pharmaceutically acceptable compositions, described supra.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, lipids, nanoparticles, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the oligonucleotides of the present disclosure may be incorporated with excipients. The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Of particular interest to the present disclosure is the use of lipid delivery vehicles. Lipid vehicles encompass micelles, microemulsions, macroemulsions, liposomes, and similar carriers. The term micelle refers to colloidal aggregates of amphipathic (surfactant) molecules that are formed at a well-defined concentration known as the critical micelle concentration. Micelles are oriented with the nonpolar portions at the interior and the polar portions at the exterior surface, exposed to water. The typical number of aggregated molecules in a micelle (aggregation number) is 50 to 100. Microemulsions are essentially swollen micelles, although not all micellar solutions can be swollen to form microemulsions. Microemulsions are thermodynamically stable, are formed spontaneously, and contain particles that are extremely small. Droplet diameters in microemulsions typically range from 10-100 nm. In contrast, the term macroemulsions refers to droplets with diameters greater than 100 nm. Liposomes are closed lipid vesicles comprising lipid bilayers that encircle aqueous interiors. Liposomes typically have diameters of 25 nm to 1 μm.

Liposomes can be constructed by well-known techniques. Lipids are typically dissolved in chloroform and spread in a thin film over the surface of a tube or flask by rotary evaporation. If liposomes comprised of a mixture of lipids are desired, the individual components are mixed in the original chloroform solution. After the organic solvent has been eliminated, a phase consisting of water optionally containing buffer and/or electrolyte is added and the vessel agitated to suspend the lipid. Optionally, the suspension is then subjected to ultrasound, either in an ultrasonic bath or with a probe sonicator, until the particles are reduced in size and the suspension is of the desired clarity. For transfection, the aqueous phase is typically distilled water and the suspension is sonicated until nearly clear, which requires several minutes depending upon conditions, kind, and quality of the sonicator. Commonly, lipid concentrations are 1 mg/ml of aqueous phase but could be higher or lower by about a factor of ten.

Lipids, from which the solvents have been removed, can be emulsified by the use of a homogenizer, lyophilized, and melted to obtain multilamellar liposomes. Alternatively, unilamellar liposomes can be produced by the reverse phase evaporation method. Unilamellar vesicles can also be prepared by sonication or extrusion. Sonication is generally performed with a bath-type sonifier, such as a Branson tip sonifier at a controlled temperature as determined by the melting point of the lipid. Extrusion may be carried out by biomembrane extruders, such as the Lipex Biomembrane Extruder (Northern Lipids Inc, Vancouver, British Columbia, Canada). Defined pore size in the extrusion filters may generate unilamellar liposomal vesicles of specific sizes. The liposomes can also be formed by extrusion through an asymmetric ceramic filter, such as a Ceraflow Microfilter (commercially available from the Norton Company, Worcester, Mass.).

Liposomes can be extruded through a small-pore polycarbonate membrane or an asymmetric ceramic membrane to yield a well-defined size distribution. Typically, a suspension is cycled through the membrane one or more times until the desired liposome size distribution is achieved. The liposomes may be extruded through successively smaller-pore membranes, to achieve a gradual reduction in liposome size. For use in the present disclosure, liposomes have a size of about 0.05 microns to about 0.5 microns or having a size of about 0.05 to about 0.2 microns.

B. Methods of Treatment

In particular, the compositions that may be used in treating cancer in a subject (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells or killing bacterial cells). Toxicity and therapeutic efficacy of the compositions utilized in methods of the disclosure can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the infection or cancer and other drugs being administered concurrently. A composition as described herein is typically administered at a dosage that inhibits the growth or proliferation of a bacterial cell, inhibits the growth of a biofilm, or induces death of cancerous cells (e.g., induces apoptosis of a cancer cell), as assayed by identifying a reduction in hematological parameters (Complete blood count (CBC)), or cancer cell growth or proliferation.

The therapeutic methods of the disclosure (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

In one embodiment, the disclosure provides a method of monitoring treatment progress. The method includes the step of determining a level of changes in hematological parameters and/or cancer stem cell (CSC) analysis with cell surface proteins as diagnostic markers (which can include, for example, but are not limited to CD34, CD38, CD90, and CD117) or diagnostic measurement (e.g., screen, assay) in a subject suffering from or susceptible to a disorder or symptoms thereof associated with cancer (e.g., leukemia) in which the subject has been administered a therapeutic amount of a composition as described herein. The level of marker determined in the method can be compared to known levels of marker either in healthy normal controls or in other afflicted patients to establish the subject's disease status. In preferred embodiments, a second level of marker in the subject is determined at a time point later than the determination of the first level, and the two levels are compared to monitor the course of disease or the efficacy of the therapy. In certain preferred embodiments, a pre-treatment level of marker in the subject is determined prior to beginning treatment according to the methods described herein; this pre-treatment level of marker can then be compared to the level of marker in the subject after the treatment commences, to determine the efficacy of the treatment.

C. Combination Therapies

It is envisioned that cPLA2α inhibitors described herein may be used in combination therapies with an additional anti-cancer agent, or a compound which mitigates one or more of the side effects of the disease or the therapy experienced by the patient. The following is a general discussion of therapies that may be used in conjunction with the therapies of the present disclosure.

To treat cancers using the methods and compositions of the present disclosure, one would generally contact a tumor cell or subject with a composition of the present disclosure and at least one other therapy. These therapies would be provided in a combined amount effective to achieve a reduction in one or more disease parameter(s). This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent. Alternatively, the compositions of the present disclosure may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations. It also is conceivable that more than one administration of either the compound or the other therapy will be desired.

Various combinations may be employed, where a cPLA2α inhibitor is "A," and the other therapy is "B," as exemplified below:

| A/B/A | B/A/B | B/B/A | A/A/B | B/A/A | A/B/B | B/B/B/A | B/B/A/B |
| A/A/B/A | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

The following are examples of standard anti-cancer therapies that could be used in combination with the compositions and methods of the present application.

1. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin $\gamma_1^I$ and calicheamicin $\omega_1^I$; dynemicin, including dynemicin A uncialamycin and derivatives thereof; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above.

2. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly.

Radiation therapy used according to the present disclosure may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors induce a broad range of damage on DNA, on the precursors of DNA, on the replication and repair of DNA, and on the assembly and maintenance of chromosomes. Dosage ranges for X-rays range from daily doses of 12.9 to 51.6 mC/kg for prolonged periods of time (3 to 4 wk), to single doses of 0.516 to 1.55 C/kg. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to normal cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Normal surrounding cells and nearby structures receive a lower dose of radiation, so the possibility of side effects is reduced. A device called a multi-leaf collimator has been developed and may be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

3. Immunotherapy

In the context of cancer treatment, immunotherapeutics, generally, rely on the use of immune effector cells and molecules to target and destroy cancer cells. Trastuzumab (Herceptin™) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells. The combination of therapeutic modalities, i.e., direct cytotoxic activity and inhibition or reduction of ErbB2 would provide therapeutic benefit in the treatment of ErbB2 overexpressing cancers.

In one aspect of immunotherapy, the tumor cell must bear some marker that is amenable to targeting, i.e., is not present on the majority of other cells. Many tumor markers exist and any of these may be suitable for targeting in the context of the present disclosure. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to combine anticancer effects with immune stimulatory effects. Immune stimulating molecules also exist including: cytokines such as IL-2, IL-4, IL-12, GM-CSF, γ-IFN, chemokines such as MIP-1, MCP-1, IL-8 and growth factors such as FLT3 ligand. Combining immune stimulating molecules, either as proteins or using gene delivery in combination with a tumor suppressor has been shown to enhance anti-tumor effects (Ju et al., 2000). Moreover, antibodies against any of these compounds may be used to target the anti-cancer agents discussed herein.

Examples of immunotherapies currently under investigation or in use are immune adjuvants e.g., *Mycobacterium bovis, Plasmodium falciparum*, dinitrochlorobenzene and aromatic compounds (U.S. Pat. Nos. 5,801,005 and 5,739, 169), cytokine therapy, e.g., interferons α, β, and γ; IL-1, GM-CSF and TNF, gene therapy, e.g., TNF, IL-1, IL-2, p53 (U.S. Pat. Nos. 5,830,880 and 5,846,945) and monoclonal antibodies, e.g., anti-ganglioside GM2, anti-HER-2, anti-p185 (U.S. Pat. No. 5,824,311). It is contemplated that one or more anti-cancer therapies may be employed with the gene silencing therapies described herein.

In active immunotherapy, an antigenic peptide, polypeptide or protein, or an autologous or allogenic tumor cell composition or "vaccine" is administered, generally with a distinct bacterial adjuvant (Ravindranath and Morton, 1991; Morton et al., 1992; Mitchell et al., 1990; Mitchell et al., 1993).

In adoptive immunotherapy, the patient's circulating lymphocytes, or tumor-infiltrated lymphocytes, are isolated in vitro, activated by lymphokines such as IL-2 or transduced with genes for tumor necrosis, and readministered.

Checkpoint inhibitors are an emerging class of immunotherapeutic. Checkpoint inhibitor therapy is a form of cancer immunotherapy currently under research. The therapy targets immune checkpoints, key regulators of the immune system that stimulate or inhibit its actions, which tumors can use to protect themselves from attacks by the immune system. Checkpoint therapy can block inhibitory checkpoints, restoring immune system function. The first anticancer drug targeting an immune checkpoint was ipilimumab, a CTLA4 blocker approved in the United States in 2011.

Currently approved checkpoint inhibitors target the molecules CTLA4, PD-1, and PD-L1. PD-1 is the transmembrane programmed cell death 1 protein (also called PDCD1 and CD279), which interacts with PD-L1 (PD-1 ligand 1, or CD274). PD-L1 on the cell surface binds to PD1 on an immune cell surface, which inhibits immune cell activity. Among PD-L1 functions is a key regulatory role on T cell activities. It appears that (cancer-mediated) upregulation of PD-L1 on the cell surface may inhibit T cells that might otherwise attack. Antibodies that bind to either PD-1 or PD-L1 and therefore block the interaction may allow the T-cells to attack the tumor.

The first checkpoint antibody approved by the FDA was ipilimumab, approved in 2011 for treatment of melanoma. It blocks the immune checkpoint molecule CTLA-4. Clinical trials have also shown some benefits of anti-CTLA-4 therapy on lung cancer or pancreatic cancer, specifically in combination with other drugs.

However, patients treated with check-point blockade (specifically CTLA-4 blocking antibodies), or a combination of check-point blocking antibodies, are at high risk of suffering from immune-related adverse events such as dermatologic, gastrointestinal, endocrine, or hepatic autoimmune reactions. These are most likely due to the breadth of the induced T-cell activation when anti-CTLA-4 antibodies are administered by injection in the blood stream.

Using a mouse model of bladder cancer, researchers have found that a local injection of a low dose anti-CTLA-4 in the tumor area had the same tumor inhibiting capacity as when the antibody was delivered in the blood. At the same time the levels of circulating antibodies were lower, suggesting that local administration of the anti-CTLA-4 therapy might result in fewer adverse events.

Initial clinical trial results with IgG4 PD1 antibody Nivolumab (under the brand name Opdivo and developed by Bristol-Myers Squibb) were published in 2010. It was approved in 2014. Nivolumab is approved to treat melanoma, lung cancer, kidney cancer, bladder cancer, head and neck cancer, and Hodgkin's lymphoma.

Pembrolizumab (brand name Keytruda) is another PD1 inhibitor that was approved by the FDA in 2014 and was the second checkpoint inhibitor approved in the United States. Keytruda is approved to treat melanoma and lung cancer and is produced by Merck.

Spartalizumab (PDR001) is a PD-1 inhibitor currently being developed by Novartis to treat both solid tumors and lymphomas. In May 2016, PD-L1 inhibitor atezolizumab was approved for treating bladder cancer. Other modes of enhancing adoptive immunotherapy include targeting so-called intrinsic checkpoint blockades, e.g., CISH.

Immunological adverse effects may be caused by check-point inhibitors. Altering checkpoint inhibition can have diverse effects on most organ systems of the body. The precise mechanism is unknown but differs in some respects based on the molecule targeted.

4. Surgery

Approximately 60% of persons with cancer will undergo surgery of some type, which includes preventative, diagnostic or staging, curative, and palliative surgery. Curative surgery is a cancer treatment that may be used in conjunction with other therapies, such as the treatment of the present disclosure, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present disclosure may be used in conjunction with removal of superficial cancers, precancers, or incidental amounts of normal tissue.

Upon excision of part or all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

In some particular embodiments, after removal of the tumor, an adjuvant treatment with a compound of the present disclosure is believed to be particularly efficacious in reducing the reoccurance of the tumor. Additionally, the compounds of the present disclosure can also be used in a neoadjuvant setting.

5. Other Agents

It is contemplated that other agents may be used with the present disclosure. These additional agents include immunomodulatory agents, agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Immunomodulatory agents include tumor necrosis factor; interferon alpha, beta, and gamma; IL-2 and other cytokines; F42K and other cytokine analogs; or MIP-1, MIP-1$\beta$, MCP-1, RANTES, and other chemokines. It is further contemplated that the upregulation of cell surface receptors or their ligands such as Fas/Fas ligand, DR4 or DR5/TRAIL (Apo-2 ligand) would potentiate the apoptotic inducing abilities of the present disclosure by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents may be used in combination with the present disclosure to improve the anti-hyperproliferative efficacy of the treatments. Inhibitors of cell adhesion are contemplated to improve the efficacy of the present disclosure. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present disclosure to improve the treatment efficacy.

There have been many advances in the therapy of cancer following the introduction of cytotoxic chemotherapeutic drugs. However, one of the consequences of chemotherapy is the development/acquisition of drug-resistant phenotypes and the development of multiple drug resistance. The development of drug resistance remains a major obstacle in the treatment of such tumors and therefore, there is an obvious need for alternative approaches such as gene therapy.

Another form of therapy for use in conjunction with chemotherapy, radiation therapy or biological therapy includes hyperthermia, which is a procedure in which a patient's tissue is exposed to high temperatures (up to 106° F.). External or internal heating devices may be involved in the application of local, regional, or whole-body hyperthermia. Local hyperthermia involves the application of heat to a small area, such as a tumor. Heat may be generated externally with high-frequency waves targeting a tumor from a device outside the body. Internal heat may involve a sterile probe, including thin, heated wires or hollow tubes filled with warm water, implanted microwave antennae, or radiofrequency electrodes.

A patient's organ or a limb is heated for regional therapy, which is accomplished using devices that produce high energy, such as magnets. Alternatively, some of the patient's blood may be removed and heated before being perfused into an area that will be internally heated. Whole-body heating may also be implemented in cases where cancer has spread throughout the body. Warm-water blankets, hot wax, inductive coils, and thermal chambers may be used for this purpose.

The skilled artisan is directed to "Remington's Pharmaceutical Sciences" 15th Edition, Chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It also should be pointed out that any of the foregoing therapies may prove useful by themselves in treating cancer.

D. Protein Detection Methods

In one aspect, the disclosure provides method for detection and quantitation of S1P, S1P receptors and S1P synthetic enzymes. A variety of different methodologies are available for the detection. In general, one can detect and quantitate proteins using antibodies that bind specifically or preferentially to this molecule, or one can employ HPLC and/or mass spectrometric methods for these purposes.

1. Mass Spectrometry

By exploiting the intrinsic properties of mass and charge, mass spectrometry (MS) can resolved and confidently identified a wide variety of complex compounds, including proteins. Traditional quantitative MS has used electrospray ionization (ESI) followed by tandem MS (MS/MS) while newer quantitative methods are being developed using matrix assisted laser desorption/ionization (MALDI) followed by time of flight (TOF) MS. In accordance with the present disclosure, one can generate mass spectrometry profiles that are useful for analyzing protein expression of S1P receptors and S1P synthetic enzymes.

2. Immunodetection

In further embodiments, there are immunodetection methods for identifying and/or quantifying S1P, S1P receptors and S1P synthetic enzymes. Some immunodetection methods include enzyme linked immunosorbent assay (ELISA), radioimmunoassay (RIA), immunoradiometric assay, fluoroimmunoassay, chemiluminescent assay, bioluminescent assay, fluorescent activated cell sorting (FACS) and Western blot to mention a few. The steps of various useful immunodetection methods have been described in the scientific literature. In general, the immunobinding methods include obtaining a sample and contacting the sample with a first antibody in accordance with embodiments discussed herein, as the case may be, under conditions effective to allow the formation of immunocomplexes. It is also possible to perform in vivo assays.

Contacting the chosen biological sample with an antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to foci-related proteins. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Non-limiting examples of reporter molecules include enzymes, radiolabels, haptens, fluorescent labels, phosphorescent molecules, chemiluminescent molecules, chromophores, photoaffinity molecules, colored particles or ligands, such as biotin. The labels used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies may be produced according to well-known methods in the art.

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

ELISAs. Immunoassays are, in their most simple and direct sense, binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the foci is added to the wells. After binding and washing to remove non-specifically bound immune complexes, the bound antigen may be detected. Detection may be achieved by the addition of another anti-foci antibody that is linked to a detectable label. This type of ELISA is a simple "sandwich ELISA." Detection may also be achieved by the addition of a second anti-foci antibody, followed by the addition of a third antibody that has binding affinity for the second antibody, with the third antibody being linked to a detectable label.

In another exemplary ELISA, the samples suspected of containing the foci are immobilized onto the well surface and then contacted with anti-foci antibody. After binding and washing to remove non-specifically bound immune complexes, the bound anti-foci antibodies are detected. Where the initial anti-foci antibodies are linked to a detectable label, the immune complexes may be detected directly. Again, the immune complexes may be detected using a second antibody that has binding affinity for the first anti-foci antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C. or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

Western Blot. The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

IV. KITS

Any of the compositions described herein may be comprised in a kit. In a non-limiting example, an oligonucleotide of pharmacologic PGC1a inhibitor is included in a kit. The kit may further include a sterile buffer to facilitate dilution. The oligonucleotide or PGC1a may be formulated for delivery to a subject, such as for systemic administration or administration to a tumor microenvironment.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present disclosure also will typically include a means for containing the oligonucleotide or PGC1a inhibitor and any other reagent containers in close confinement for commercial sale. Such containers may include injection or blow-molded plastic containers into which the desired vials are retained. Instructions may include variations that can be implemented.

When the components of the kit are provided in one and/or more liquid solutions, the liquid solution is an aqueous solution, with a sterile aqueous solution being particularly preferred. However, the active agent may be provided as dried powder(s). When reagents and/or components are provided as a dry powder, the powder can be reconstituted by the addition of a suitable solvent. It is envisioned that the solvent may also be provided in another container means. Such kits may also include components that preserve or maintain the active agent that protect against its degradation.

V. EXAMPLES

The following examples are included to demonstrate certain non-limiting aspects of the disclosure. It should be appreciated by those of skill in the art that the techniques disclosed in the examples which follow represent techniques discovered by the inventor to function well in the practice of the disclosure. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Human samples and cell lines. Tumor samples of melanoma and breast cancers were obtained from hospitalized patients in the Department of Surgery at St. Louis University from 2004 to 2017 who have given informed consents for enrollment in a prospective tumor procurement protocol approved by the Saint Louis University Institutional Review Board (IRB #15283). Buffy coats from healthy donors were obtained from the Gulf Coast Regional Blood Center at Houston. Peripheral blood mononuclear cells (PBMCs) were purified from buffy coats using Ficoll-Paque. Human naïve CD4+ and CD8+ T cells were purified by EasySep enrichment kits (StemCell Technologies). Naturally occurring human CD4 CD25$^{hi}$ Treg cells (nTreg) were purified from CD4+ T cells by FACS sorting after staining with anti-CD25-PE (BD Biosciences), or isolated from PBMCs by negative selection with the human CD4$^+$ CD127$^{low}$CD49d$^-$ Treg cell enrichment kit (StemCell Technologies). Melanoma and breast cancer cell lines were purchased from the American Type Culture Collection (ATCC, Manassas, VA). Melanoma 586mel and paired TIL586 were obtained from the Surgery Branch, National Cancer Institute (NCI).

Senescence associated β-galactosidase staining. Senescence associated β-galactosidase (SA-β-gal) activity in senescent T cells was detected as the inventors previously described 23,32,33. Naive CD4+ or CD8+ T cells were labeled with CFSE (4.5 μM), and co-cultured with Treg cells at a ratio of 4:1 in anti-CD3-coated 24-well plates for 3 days. Co-cultured naïve T cells were then separated from co-cultures using FACS sorting gated on CFSE positive populations, and then stained with SA-β-Gal staining reagent. For tumor-induced T cell senescence, anti-CD3 activated naïve CD4+ T cells or CD8+ T cells were co-cultured with or without tumor cells at ratio of 1:1 for 1 day and then separated and cultured for additional 3 days. For some experiments, naïve T cells were pretreated with the following inhibitors and then co-cultured with Treg cells. SA-β-gal expression in the co-cultured naïve T cells was determined. These inhibitors include: ACAT inhibitor Avasimable (5 μM and 10 μM), lipase inhibitor orlistat (10 μM), and cPLA2α inhibitor MAFP (1 μM and 5 μM) (Cayman Chemical); ATM inhibitor KU55933 (10 μM, Tocris Bioscience); stat1 inhibitor MTA (5 μM), stat3 inhibitor S3I-201 (10 μM) (Sigma-Aldrich); MAPK inhibitors including U0126 (10 μM) and SB203580 (10 μM) (Calbiochemistry).

Flow cytometry analysis. The expression markers on T cells were determined by flow cytometry analysis after surface staining or intracellular staining with anti-human specific antibodies conjugated with PE or Alexa Flour488. The human antibodies included: anti-CD27, anti-CD28, anti-phospho-ERK (Thr202/Tyr204), anti-phospho-p38 (Thr180/Tyr182), anti-phospho-STAT1 (Tyr701), anti-phospho-STAT3 (Tyr705 or Ser727), anti-phospho-ATM, anti-phospho-H2AX, anti-phospho-CHK2, anti-phospho-53BP1, and anti-cPLA2α, which were purchased from BD Biosciences, Biolegend, or Cell Signaling Technology. For Bodipy 493/503 staining (Thermo Fisher Scientific), T cells were incubated with Bodipy 493/503 (1 μg/ml) at room temperature for 15 minutes. All stained cells were analyzed on a LSR II cytometer (BD Bioscience) and data analyzed with FlowJo software (Tree Star).

Western-blotting analysis. CFSE-labeled naïve CD4+ or CD8+ T cells were co-cultured with Treg or control T cells at a ratio of 4:1 in the anti-CD3 antibody-precoated plates (2 μg/ml) for 3 days. In some experiments, T cells were pretreated with the cPLA2α inhibitor MAFP (5 M) for 24 hours, and then co-cultured with Treg cells. Treated T cells were then sorted by FACS gating on CFSE positive T cells. Whole cell lysates of the purified CD4+ T cells were prepared for western blot analyses. Western blots were developed with the Chemiluminescent Substrate (KPL, Maryland). The rabbit polyclonal antibodies used in the western blot analyses are as following: anti-cPLA2α, anti-P53, anti-P21, and anti-GAPDH. All antibodies were purchased from the Cell Signaling Technology.

Reverse-transcription quantitative PCR analysis. Total RNA was extracted from T cells using Trizol reagent (Invitrogen), and cDNA was transcribed using a SuperScript II RT kit (Invitrogen), both according to manufacturers' instructions. Expression levels of each gene were determined by reverse-transcription PCR using specific primers, and mRNA levels in each sample were normalized to the relative quantity of the housekeeping GAPDH or β-actin gene expression. All experiments were performed in triplicate. The specific primers used for T cells are listed in Supplemental Table S1.

Functional proliferation assay. Proliferation assays were performed using a [$^3$H]-thymidine incorporation assay, as the inventors previously described (Liu et al., 2018; Ye et al., 2014; 2012; Peng et al., 2005; 2007). Naïve CD4+ T cells ($1\times10^5$/well) purified from healthy donors were co-cultured with Treg-treated T cells at a ratio of 10:1 in 200 μl of T cell assay medium containing 2% human AB. After 56 hours of culture, [3H]-thymidine was added at a final concentration of 1 μCi/well, followed by an additional 16 hours of culture. The incorporation of [$^3$H]-thymidine was measured with a liquid scintillation counter.

Lipidomics analysis. Lipids from T cells were extracted by the method of Bligh and Dyer in the presence of internal standards including eicosanoic acid, 1-0-heptadecanoyl-LPC, dieicosanoyl-PC, ditetradecanoyl-PE, ditetradecanoyl-PS, N-heptadecanoyl-Cer, and cholesteryl heptadecanoate (Bligh and Dyer, 1959). Extracted lipids were resuspended in methanol/chloroform (2:1, by vol.) and analyzed by ESI-MS in the direct infusion mode at a flow rate of 3 μl/min using a Thermo Electron TSQ Quantum Ultra® instrument. Samples were analyzed in both the positive and negative ion mode using a shotgun lipidomics approach (Han and Gross, 2005). For LPC, neutral loss (NL) scanning of 59.1 was monitored in the positive ion mode for sodiated molecular ions. NL scanning of 368.5 was performed for sodiated CE molecular species in the positive ion mode (Bowden et al., 2011). PE was derivatized to fMOC-PE species and monitored in negative ion mode using NL scanning of 222.2. Neutral loss scanning for Cer (NL 256.2), PC (NL50) and PS (NL 87) was performed in the negative ion mode (Han and Gross, 2005). Fatty acids were converted to pentafluorobenzyl esters and quantified using negative ion chemical ionization detection and gas chromatography (Quehenberger et al., 2010). Spectra were averaged over 3-5 min and processed utilizing Xcalibur® software (Thermo Electron). Individual molecular species were quantified by comparing the ion intensity of individual molecular species to that of the appropriate internal standards following corrections for type I and type II 13C isotope effects (Han and Gross, 2005). Additional corrections were made from response curves for CE molecular species (Bowden et al., 2011). Each sample was normalized to cell number, and values are expressed per million cells.

Lipid supplement assay. Lysophosphatidylcholine (LPC, 16:0 LPC, 16:0 aLPC, and 16:0 pLPC), Phosphatidylethanolamine (PE, 16:0 lyso PE) and Phosphatidylserine (PS, 16:0 lyso PS) were purchased from the Avanti Polar Lipids, INC. C2-Ceramide was purchased from Sigma. All the lipids were dissolved in chloroform, evaporated under a gentle stream of nitrogen and then immediately dissolved in an ethanol vehicle (0.1%). Naïve CD4+ T cells were first treated with or without the lipids (5 μM or 10 μM) for 1 hour and then co-cultured with Treg cells at a ratio of 4:1 in anti-CD3-coated (2 μg/ml) plates for 3 days. The treated naïve CD4+ T cells were then performed SA-β-gal and Oil red O staining.

Oil-Red O staining. The treated T cells were washed in PBS (pH 7.2), fixed with 4% formaldehyde for 30 minutes, and treated with 60% isopropanol for 2-5 minutes. Cells were further stained with freshly prepared Oil-Red O staining solution (Sigma-Aldrich) in isopropanol (60%) for 5 minutes, followed by quick rinse with isopropanol (60%). The stained cells were then washed with H2O thoroughly and lipid droplets in T cells were evaluated using a light microscope. Indirect immunofluorescence staining Naïve CD4+ T cells were co-cultured with Treg cells or control T cells in the presence of plate-bound anti-CD3 antibody (2 μg/ml) for 3 days. The co-cultured T cells were incubated with primary rabbit anti-human antibodies, including rabbit anti-phospho-ERK (Thr202/Tyr204), anti-phospho-p38 (Thr180/Tyr182), anti-phospho-stat1 (Tyr701), anti-phospho-stat3 (Tyr705), anti-P21, anti-P53, and anti-cPLA2α antibodies. The treated CD4+ T cells were then incubated with BODIPY 493/503 and the Alexa Fluor 594-conjugated anti-rabbit secondary antibody (Cell Signaling Technology), and were further counterstained with 40, 6-diamidino-2-phenylindole (DAPI; Invitrogen).

Transcriptome analyses of senescent T cells. Anti-CD3-activated naïve CD8+ T cells were co-cultured with medium only or CD4$^+$CD25$^{hi}$FoxP3$^+$ Treg cells at a 5:1 ratio for different time points, including early (4-8 h), middle (24-48 h) and late (72 h). Total RNA was purified from the Treg-treated and untreated naïve CD8+ T cells using RNeasy Kit (Qiagen). Transcriptome analyses of senescent CD8+ T cells induced by human Treg cells were performed using the Illumina whole-genome HumanHT-12 BeadChips, as the inventors previously described (Liu et al., 2018; Ye et al., 2012). Gene Ontology (GO) terms associated with each gene were used to characterize the functionally-related genes and identify processes associated with networks of differentially expressed genes. The normalized log 2 expression level of each gene was calculated.

In vivo studies. C57BL/6 mice, NOD-scid IL2Rγ$^{null}$ (NSG) mice, and Pmel-1 TCR/Thy1.1 transgenic mice on a C57BL/6 background (6 to 8-wk-old female) were purchased from The Jackson Laboratory and maintained in the institutional animal facility. All animal studies have been approved by the Institutional Animal Care Committee at Saint Louis University (Protocol No. 2411).

Analyses of T cells in the tumor microenvironment: Mouse E0771 (2×10$^5$/mouse) breast tumor cells and melanoma cell line B16F0 (2×10$^5$/mouse) in 100 μl of buffered saline were subcutaneously injected into the mammary fat pad and back of C57BL/6 mice, respectively. Five to ten mice were included in each group. Tumor volumes were measured every 3 days. When the tumor volumes reached the expected size (diameter 10-15 mm), the tumor-bearing mice were sacrificed. Blood, lymph nodes (LN), spleens (SP) and tumor tissues were harvested and CD4+ and CD8+ T cells were purified for subsequent SA-β-gal staining, Oil-red O staining and metabolic gene profile analyses. In addition, CD4+ and CD8+ T cells from different organs of normal littermates were harvested and used as negative controls Mouse T cell adoptive transfer therapy models: Splenocytes from Pmel-1 TCR/Thy1.1 transgenic mice were prepared and activated in the presence of plate-coated anti-mouse CD3 (2 μg/ml) and anti-mouse CD28 (1 μg/ml) antibodies for 6-9 days. For the B16 melanoma models, The activated Pmel-1 T cells (2×10$^6$) were adoptively transferred into B16F10-bearing mice at day 6 (early stage treatment) or day 11 (late stage treatment) post tumor inoculation (2×10$^5$/ mouse). For the E0771 breast cancer model, E0771 tumor cells were transduced with retroviral vector encoding tumor antigen gp100 and mIL-4R genes as previously described (Peng et al., 2010). E0771/gp-100 tumor cells were obtained after FACS sorting based on mIL-4R expression. E0771/ gp100 (2×10$^5$/mouse) cells were subcutaneously injected into the mammary fat pad of NSG mice. On day 6 after E0771/gp-100 tumor cell injection, the activated Pmel-1 T cells (2×10$^6$/mouse) were adoptively transferred into E0771-bearing mice. In both B16F10 and E0771 models, the tumor-bearing mice were radiated with a nonmyeloablative dose (500 cGy) to induce lymphopenia 1 day before T cell adoptive transfer. In a parallel experiment, MAFP (7.5 mg kg-1/mouse) was injected intraperitoneally into the mice at 1 day after T cell transfer and then injected every 3 days for a total of 4 times. In addition, recombinant human IL-2 (1× 10$^5$ I.U. twice daily) was also intraperitoneally administered for a total of 3 days after T cell transfer. Five- to ten mice were included in each group. Tumor size was measured with calipers every 3 days and tumor volume was calculated on the basis of two-dimension measurements. Blood, spleens, and tumors were harvested at the end of each experiment. The transferred CD8+ T cells from different organs and tumor tissues were isolated by antibody-coated microbeads (StemCell Technologies) for subsequent SA-β-gal staining, Oil-red O staining and gene expression profile analyses.

Human T cell adoptive transfer experiments: Human 586mel tumor cells (5×10$^6$/mouse) in 100 μl of buffered saline were subcutaneously injected into NSG mice. Tumor-specific CD8+ TIL586 cells (5×10$^6$/mouse) were i.v. injected on day 5 into the tumor-bearing mice. In a parallel experiment, MAFP (7.5 mg kg-1/mouse) was injected intraperitoneally into the mice at 1 day after adoptive transfer of CD8+ TIL586 cells and followed the identical treatment procedures and doses to the above Pmel-1 T cell experiments. Five to ten mice were included in each group. Tumor size was measured and the transferred human TIL586 CD8+ T cells were recovered for subsequent phenotypic and functional analyses in vitro, as described above.

Statistical analysis. Statistical analysis was performed with GraphPad Prism5 software. Unless indicated otherwise, data are expressed as mean±standard deviation (SD). For multiple group comparison in vivo studies, the one-way analysis of variance (ANOVA) was used, followed by the Dunnett's test for comparing experimental groups against a single control. For single comparison between two groups, paired Student's/test was used. Nonparametric t-test was chosen if the sample size was too small and not fit Gaussian distribution.

Example 2—Results

Development of T cell senescence is a general feature in the tumor microenvironment. It has become clear that tumor-reactive T cells are suppressed and dysfunctional in the tumor suppressive microenvironment that is a major obstacle for successful tumor immunotherapy. The inventors discovered that human Treg cells can induce both responder CD4+ and CD8+ T cells to become senescent (FIG. 1A and FIG. 13A) (Liu et al., 2018; Ye et al., 2012; 2013). In addition to Treg cells, the inventors demonstrated that different types of human cancer cells, including breast cancer MCF-7 and melanoma M586 cells, can induce senescence in co-cultured T cells (FIG. 1B and FIG. 13B) Ye et al., 2014; Ye and Peng, 2015). Senescent T cells induced by human Treg cells and tumor cells change their phenotypes and functions. The expression of co-stimulatory molecules CD27 and CD28 were significantly down-regulated (FIG. 13C), but high amounts of proinflammatory and suppressive cytokines IL-1B, IL-6, IL-8, TNF and IFN-γ were produced (FIGS. 13C-D and FIG. 13D) (Liu et al., 2018; Ye et al., 2012; 2013). In addition, senescent T cells possessed strong suppressive activity and potently inhibited the proliferation of other responding CD4+ T cells (FIG. 13E) (Liu et al., 2018; Ye et al., 2012; 2013).

Figure 13:
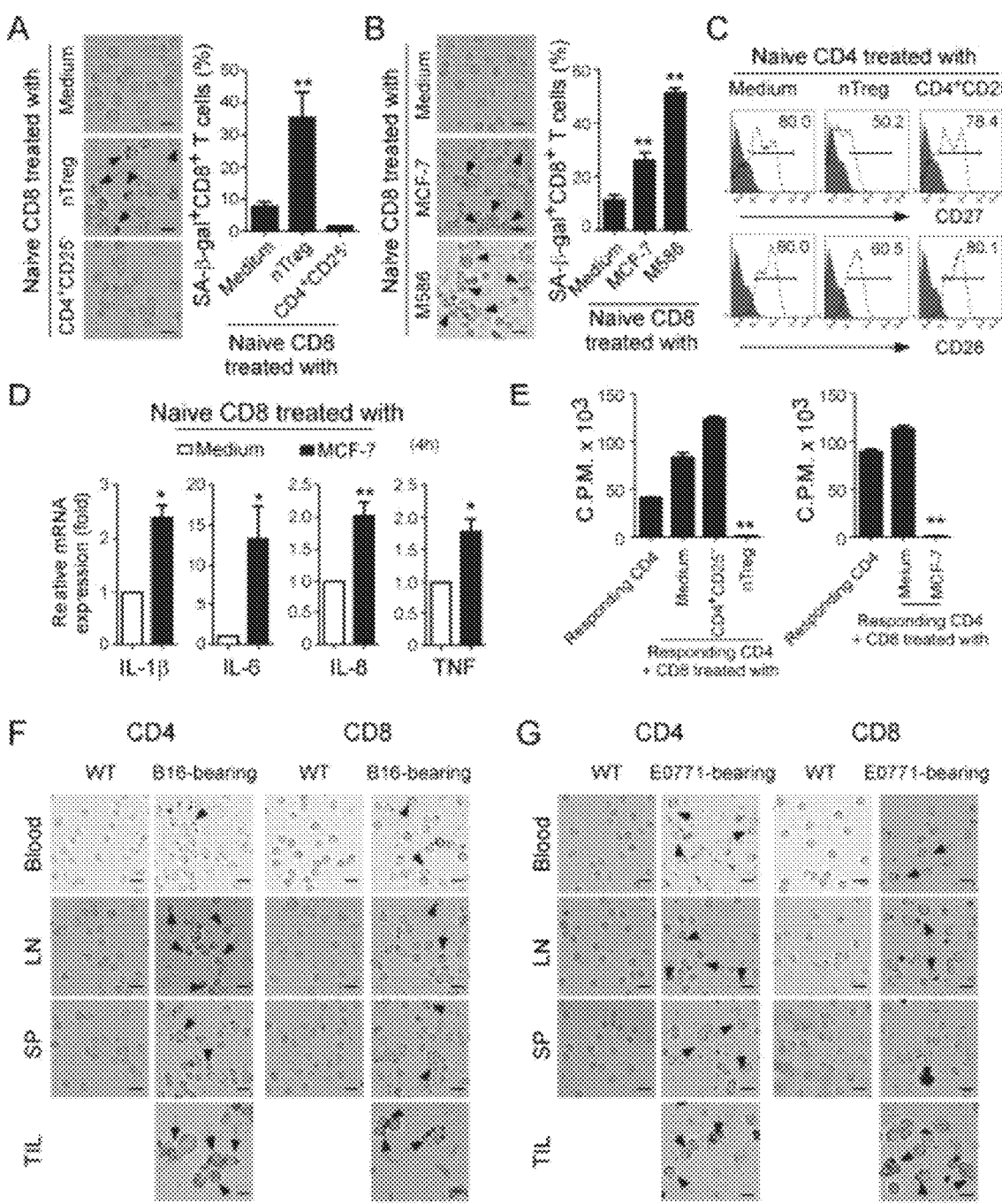

To further determine the generality of the development of senescent T cells as a potential form of tumor-mediated immune evasion, the inventors investigated the existence of senescent T-cell populations in the tumor suppressive microenvironment. The inventors first utilized murine mammary cancer cell line E0771 and melanoma cell line B16F0 to establish breast cancer and melanoma cancer models, respectively. T cells from different organs and tumor sites in the tumor-bearing mice were then recovered and analyzed after tumor diameters reached 10-15 mm. The inventors observed markedly elevated SA-β-gal-positive CD4+ and CD8+ T cells existing in blood, lymph nodes, spleens, and tumors derived from B16F0-bearing mice rather than in control wild-type mice, suggesting development of senescence in these T cells (FIG. 1E and FIG. 13F). Notably, the percentages of senescent T cell populations in TILs reached 60% (FIG. 1E). Furthermore, increased mRNA expression levels of pro-inflammatory cytokines IL-1β, IL-6, TNF and IFN-γ were induced in both CD4+ and CD8+ T cells recovered from blood and tumor tissues in B16F0-bearing mice but not in control mice (FIG. 1F). The inventors observed the similar results in the E0771 mouse models that promoted senescent T cell populations and enhanced inflammatory cytokine secretion in T cells were induced from different organs and tumor tissues (FIGS. 1G, 1H and FIG. 13G). The inventors then generated TILs from fresh tumor tissues obtained from breast cancer and melanoma patients. Elevated senescent T cell populations were observed among the TILs from both breast cancer and melanoma tumor tissues (FIG. 1I) (Ye et al., 2014). In addition, these TILs had increased pro-inflammatory cytokine secretion profiles (FIG. 1J). These results collectively indicate that induction of T cell senescence is an important strategy utilized by malignant tumors to mediate T cell dysfunction and evade immune surveillance.

Figure 14:
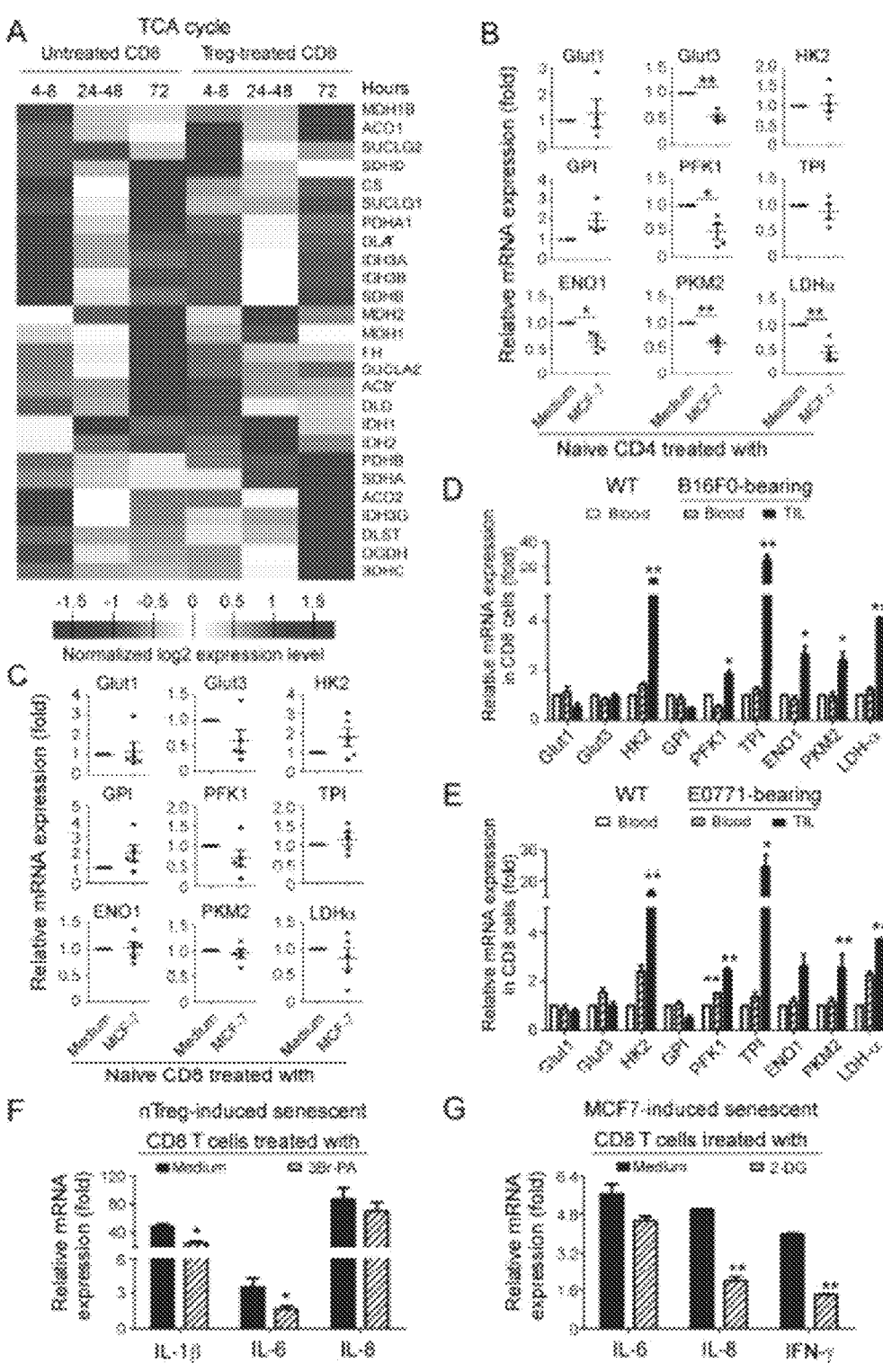

Senescent T cells have active glucose metabolism. To dissect the mechanism responsible for generation of senescent T cells mediated by human Treg cells, the inventors have shown that senescent T cells induced by Treg cells have increased phosphorylation of AMP-activated protein kinase (AMPK), an important nutrient and energy sensor (Liu et al., 2018). Therefore, the inventors reasoned that development of senescent T cells might involve metabolic regulation induced by Treg cells and tumor cells. Glucose metabolism is the main metabolic pathway required for effector T cell functions upon activation (Macintyre et al., 2014; McIver et al., 2013). The inventors first conducted transcriptome analyses of senescent T cells induced by human nTreg cells at different times during the senescence development using Illumina whole-genome Human HT-12 BeadChips. The inventors' transcriptome analyses demonstrated that Treg cell treatment significantly increased the gene expression levels of enzymes involved in glycolysis, and also slightly increased expression levels of enzymes involved in tricarboxylic acid cycle (TCA) pathways in responder T cells in the middle (24-48 hours) and late (72 hours) stages of senescence development (FIG. 2A and FIG. 14A). These results suggest that senescent T cells have heightened glucose metabolism.

To validate the information from the transcriptome analyses of senescent T cells, the inventors then characterized the key metabolic genes involving glucose metabolism in senescent T cells induced by human Treg cells and tumor cells using real-time quantitative PCR analyses[41]. Those molecules include glucose transporters Glut1 and Glut3, as well as glycolysis-related enzymes hexokinase 2 (HK2), glucose-6-phosphate isomerase (GPI), phosphofructokinase 1 (PFK1), triosephosphate isomerase 1 (TPI1), enolase 1 (ENO1), pyruvate kinase muscle 2 (PKM2) and lactate dehydrogenase A (LDHα). The inventors found that mRNA expression levels of the glucose metabolic genes were varied in senescent CD4+ T cells induced by both nTreg cells and MCF-7 tumor cells, compared with CD4+ T cells cultured in medium or with CD4+CD25-control cells (FIG. 2B and FIG. 14B). However, majority of these metabolic genes were increased or with no change in senescent CD8+ T cells induced by both nTreg cells and MCF-7 cells, except down-regulation of ENO1 and LDHα in senescent CD8+ T cells induced by nTreg cells (FIG. 2C and FIG. 14C).

To further investigate the glucose metabolic profiles of T cells in vivo in tumor-bearing hosts, the inventors determined those glucose metabolic gene expressions in T cells in melanoma and breast cancer tumor-bearing mice. The inventors found that mRNA expression levels of majority of those molecules were significantly increased in both CD4+ and CD8+ T cells in TILs obtained from B16 and E0771tumor-bearing mice (FIGS. 2D & 2E and FIGS. 14D-E). In addition, the inventors purified TILs from fresh tumor tissues of melanoma cancer patients and determined those glucose metabolic molecule levels. The inventors observed similar results as shown in the mouse tumor models that majority of those molecules were not suppressed in TILs from melanoma patients (FIG. 2F). These results collectively suggest that senescent T cells are not exhausted and still possess active glucose metabolism to maintain their biological and functional demands.

To further dissect the role of glucose metabolism in T cell senescence, the inventors found that addition of high concentration of glucose (25 mM) dramatically prevented the responder T cell senescence mediated by nTreg cells (FIG. 2G). Importantly, addition of high concentration of glucose also significantly prevented induction of senescence in both CD4+ and CD8+ T cells mediated by breast cancer cells (FIG. 2H). These results indicate the importance of glucose competition between responder T cells and Treg/tumor cells for the development of T cell senescence. The inventors next explored the critical role of glucose metabolism in the already established senescent T cell functions. These results showed that high concentration of glucose (25 mM) cannot reverse cell senescence in the already developed senescent T cells induced by both Treg cells and tumor cells (FIG. 2I). However, blockade of glycolysis in senescent T cells using the pharmaceutical inhibitors of 2-DG or 3-BrPA significantly decreased the secretion of pro-inflammatory cytokines and inhibited their suppressive activity on proliferation of effector T cells mediated by senescent T cells (FIGS. 14F-G and data not shown) (Liu et al., 2018). These results indicate that senescent T cells have active glucose metabolism that is required for executing their biological functions.

Figure 15:
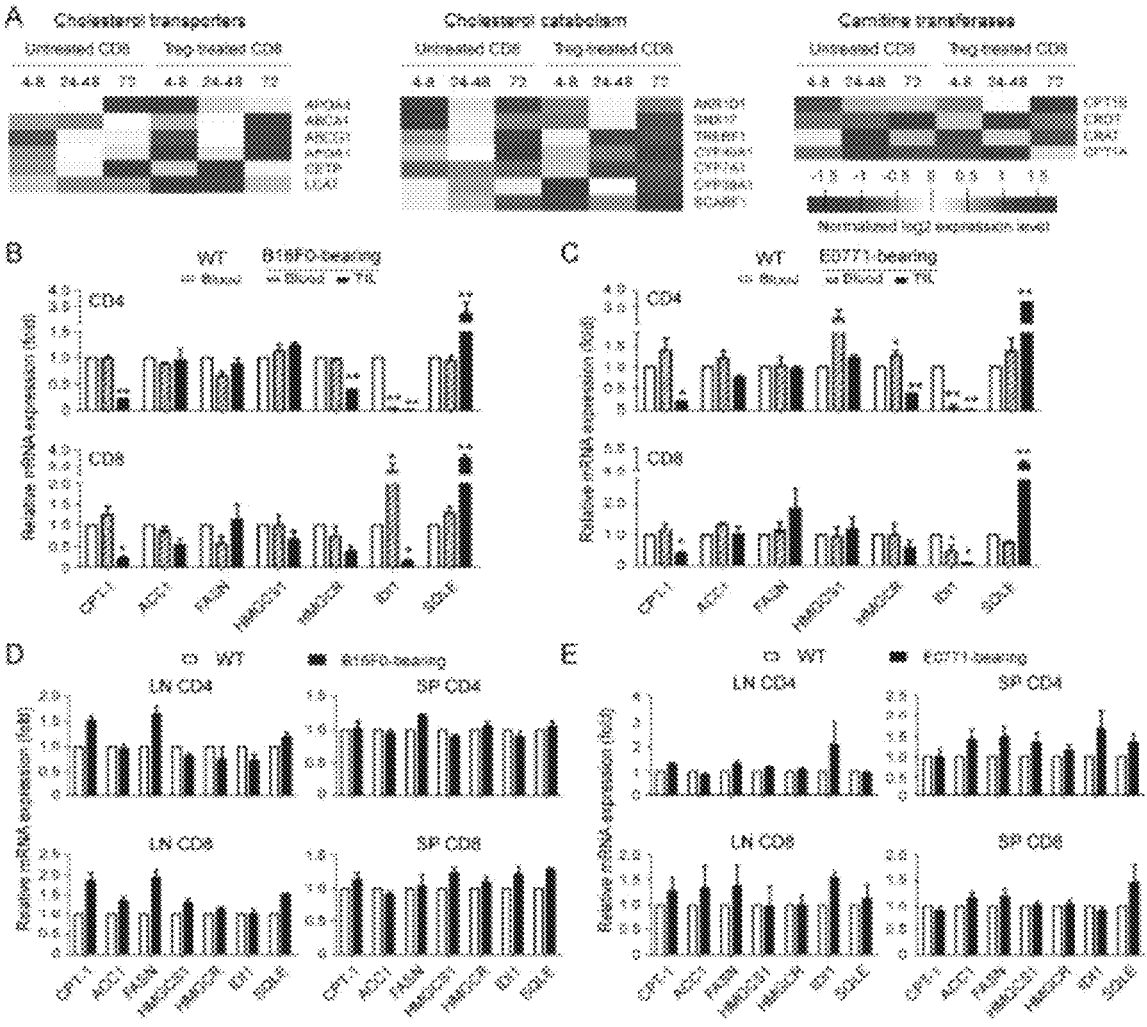

Senescent T cells have unbalanced lipid metabolism. It has been shown that lipid metabolism is critical for certain T cell development and functions, including Treg, Th17 cells and memory CD8+ T cells (Michalek et al., 2011; Shi et al., 2011; Pearce et al., 2009; Buck et al., 2016; Berod et al., 2014). Furthermore, fatty acid metabolism is linked to cellular senescence (Ford et al., 2010). Therefore, the inventors determined whether lipid metabolic regulation is involved in the development of senescent T cells induced by Treg cells and tumor cells. The inventors performed transcriptome analyses of senescent T cells induced by human nTreg cells at different times and further identified the altered genes involved in lipid metabolism in senescent T cells. The inventors found that Treg treatment significantly promoted the expression levels of genes involved in cho-lesterol biosynthesis and transport, and fatty acid biosyn-thesis in responder T cells during the early and middle stages of senescence development, but those genes were decreased in senescent T cells at the late stage of T cell senescence (72 hours). Furthermore, the genes involved in regulation of triacylglycerol (TAG) metabolism were up-regulated in senescent T cells. In addition, the genes involved in the catabolism of cholesterol, fatty acid and TAG were dramati-cally down-regulated in senescent T cells (FIG. 3A and FIG. 15A). These results suggest that lipid metabolism might be critical for T cell senescence.

The inventors then determined expression levels of the key enzymes related to both cholesterol synthesis, and fatty acid oxidation and synthesis in senescent CD4+ and CD8+ T cells induced by human nTreg cells and MCF-7 breast cancer cells, including 3-hydroxy-3-methyl-glutaryl-CoA reductase (HMGCR), 3-hydroxy-3-methylglutaryl-CoA synthase 1 (HMGCS1), squalene monooxygenase (SQLE), isopentenyl-diphosphate delta isomerase 1 (IDI1), carnitine palmitoyltransferase I (CPT-1), fatty acid synthase (FASN) and acetyl-CoA carboxylases 1 (ACC1) (Li et al., 2019). These studies clearly demonstrated significantly down-regu-lated gene expression levels of the most key enzymes related to cholesterol and fatty acid metabolism in the already senescent CD4+ and CD8+ T cells induced by human nTreg cells and MCF-7 cells (FIGS. 3B-3E). Actually, consistent with the transcriptome analysis results, these enzyme expressions were dynamically changed with an increase in the early time and then a decrease in the late time during the senescence development in T cells induced by nTreg cells (FIG. 3F). The inventors further determined whether these lipid-associated enzymes were also suppressed in T cells in tumor-bearing mice in B16 melanoma and E0771 breast cancer tumor models. The inventors observed significantly down-regulated expression of CPT1, HMGCR and IDI1 and increased expression of SQLE in the TILs from both B16 and E0771 tumor-bearing mice (FIGS. 15B-C). However, the mRNA levels of those lipid enzymes were not obviously altered in CD4+ and CD8+ T cells recovered from blood, spleens and lymph nodes in B16 and E0771 tumor-bearing mice compared with those in T cells from wild-type mice (FIGS. 15B-E). In addition, the inventors found dramatically down-regulated expression of CPT1, HMGCR, IDI1 and SQLE, and up-regulation of FASN in the TILs from mela-noma patients (FIG. 3G). These results demonstrate dynamic changes and unbalanced lipid metabolism in senes-cent cells induced by both Treg cells and tumor cells in the tumor suppressive microenvironment.

Figure 17:
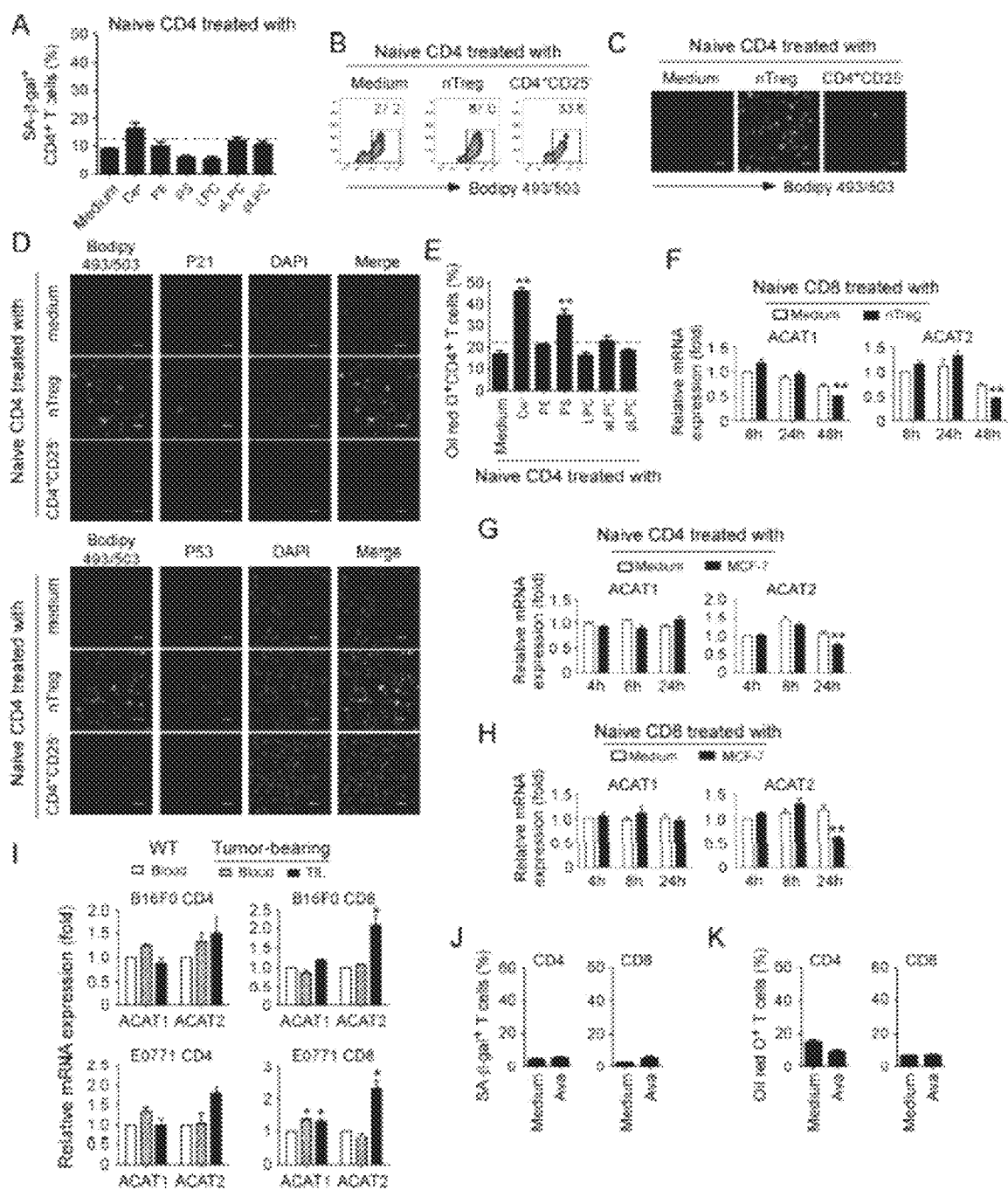

In addition to the changes of lipid metabolism enzymes, the inventors further identified what lipid species are changed in senescent T cells induced by Treg cells and tumor cells and whether the altered lipid components are causatively related to T cell senescence and impaired func-tions. The inventors performed a mass spectrometry-based lipidomics screen to identify the changes of lipid species and metabolites during the T cell senescence mediated by nTreg cells and MCF-7 breast cancer cells. The inventors are particularly interested in the following 2 lipid subclasses, glycerophospholipids (GP) and sphingolipids (SP) (FIG. 4A and FIG. 16) (Han and Gross, 2005; Bowden et al., 2011). All these lipids are acting as structural components of cell membranes. nTreg-induced senescent T cells showed higher levels of total and majority of sub-fractions of free fatty acids (FFA) and cholesteryl ester (CE), but lower levels of ceramide (Cer), sphingomyelins (SM), phosphatidylcholine (PC), and phosphatidylethanolamine (PE) than those in control T cells (FIGS. 4B, 4C and 4E, and data not shown). Senescent T cells induced by nTreg cells did not show changes of lysophosphatidylcholine (LPC) compared with control T cells (Data not shown). Furthermore, senescent T cells induced by MCF-7 breast cancer cells also showed significantly increased total and sub-fractions of CE, and decreased ceramide and PE compared with control T cells (FIGS. 4D and 4E). MCF-7-mediated senescent T cells did not develop markedly altered levels of PC, PS, SM and LPC (FIG. 4E). The inventors then determined whether the reduced lipid species are critical for T cell senescence and impaired functions induced by Treg cells and cancer cells. The inventors observed that addition of different concentra-tions of Cer, PE, PS, LPC, aLPC and pLPC, markedly prevented senescence induction in T cells co-cultured with nTreg cells (FIG. 4F), while these lipids themselves did not affect T cell senescence except Cer (FIG. 17A). Collectively, these data strongly indicate that unbalanced lipid metabo-lism plays a crucial role in regulation of senescence devel-opment in T cells mediated by human Treg cells and tumor cells in the tumor microenvironment.

Accumulated lipid droplets involve the development of T cell senescence. In addition to the effects of the loss of lipid species, the inventors next explored the role of the increased lipid species in senescent T cell development mediated by Treg cells and tumor cells. These studies have shown that CE is dramatically increased in senescent T cells (FIGS. 4C and 4D). More recent work has demonstrated that T cells with increased cholesterol esterification have impaired pro-liferation and anti-tumor effector function (Yang et al., 2016). These studies further showed significantly increased fatty acid biosynthesis and TAG metabolism in senescent T cells (FIGS. 3A-G and FIGS. 4A-F). These are key com-ponents for LDs, which are lipid-rich cytoplasmic organelles that directly regulate inflammation and cancer (Yang et al., 2016; Fujimoto and Parton, 2011; Guijas et al., 2014) (FIG. 5A). Therefore, the inventors determined whether increased LD formation was induced during the molecular processes of T cell senescence mediated by both Treg cells and tumor cells using the Oil red O staining. As expected, the inventors observed that Oil red O+ T cell populations were signifi-cantly increased in naïve CD4+ and CD8+ T cells after co-culture with nTreg cells, as well as with MCF-7 and M586 tumor cells (FIGS. 5B and 5C). The inventors also utilized the lipophilic fluorescent dye Bodipy 493/503 to evaluate the amount of lipids in senescent T cells (Span-genburg et al., 2011). Consistent with the Oil red O staining results, Treg-induced senescent T cells displayed more fluo-rescence intensity than that of naïve CD4+ T cells cultured in medium only or with CD4+CD25-effector T cells (FIG. 17C). In order to identify the relationship between the accumulated LDs and cell senescence in T cells, the inven-tors isolated $Bodipy^{high}$, $Bodipy^{medium}$ and $Bodipy^{low}$ popu-lations in senescent T cells induced by nTreg cells with FACS sorting and found that almost all the SA-β-gal+ T cells were in the $Bodipy^{high}$ populations, indicating that LD formation occurs in T cells during senescent T cell devel-opment (FIG. 5D). In addition, LD formation was co-localized with increased cell cycle regulatory molecules p21 and p53 in nTreg-induced senescent T cells (FIG. 17D). The inventors also determined whether the reduced lipid species have a relationship with the accumulated LDs in senescent T cells. These lipid species themselves except Cer and PS, did not promote LD formation in T cells (FIG. 17E). However, supplement of these lipids can significantly prevent LD formation in T cells induced by Treg cells, as indicated by decreased Oil red O+ T cell populations in senescent T cells (FIG. 5E). These results suggest the interactions and cross-talks among lipid species and LDs are critical for the development of T cell senescence.

The inventors next dissected the molecular mechanism(s) responsible for the increased CE and LDs during T cell senescence induced by Treg and tumor cells. CE synthesis is controlled by the cholesterol acyltranserases 1 and 2 (ACAT1 and ACAT2) (FIG. 5A) 49-51. The inventors therefore determined whether senescent T cells induced by Treg cells and tumor cells have increased expressions of ACAT1 and/or ACAT2. Surprisingly, gene expression levels of ACAT1 and ACAT2 were significantly down-regulated rather than increased in senescent CD4+ and CD8+ T cells induced by nTreg cells and MCF-7 cancer cells (FIGS. 5F and 5G). The inventors further determined the kinetic changes of these two genes during T cell senescence. ACAT1 and ACAT2 mRNA levels were not significantly changed at the early time points but then decreased at the late time point (at 48 hours) in both Treg and tumor-induced senescent T cells (FIGS. 17F-H). However, the inventors observed increased ACAT1 expression in CD8+ T cells from blood and TILs in E0771-bearing mice and ACAT2 in CD8+ TILs from both B16-bearing and E0771-bearing mice (FIG. 17I). To identify the importance of increased CE for T cell senescence, the inventors utilized the loss-of-function assay with the ACAT inhibitor avasimible and determined whether blockage of CE synthesis can prevent cell senescence and LD formation in T cells after co-culture with human nTreg cells. The inventors unexpectedly found that avasimible treatment did not significantly down-regulate total and sub-fractions of CE in senescent T cells (FIG. 5H). However, treatment with avasimible dramatically reduced senescent T cell and Oil red O+ T cell populations in naïve CD4+ and CD8+ T cells induced by Treg cells (FIGS. 5I-5J). The inventors ruled out the possibility that avasimible treatment does not induce cell senescence and LD formation in naïve T cells (FIGS. 17J-K). In addition to ACAT, the lysosomal acid lipase (LAL) encoded by LIPA is another important enzyme involved in down-regulation of CE and LD formation (FIG. 5A) 49-51. The inventors therefore determined LIPA expression in senescent T cells and found that LIPA was significantly down-regulated in senescent T cells during the senescence development mediated by Treg cells (FIG. 5K). Furthermore, inhibition of LIPA with the specific inhibitor orlistat dramatically increased cell senescence and promoted LD formation in naïve T cells, suggesting LIPA might also be involved in the induction of T cell senescence and increases of CE and LDs (FIGS. 5L-M). Collectively, these results indicate that accumulation of LDs in T cells induced by Treg and tumor cells is a critical process for the development of T cell senescence.

Figure 18:
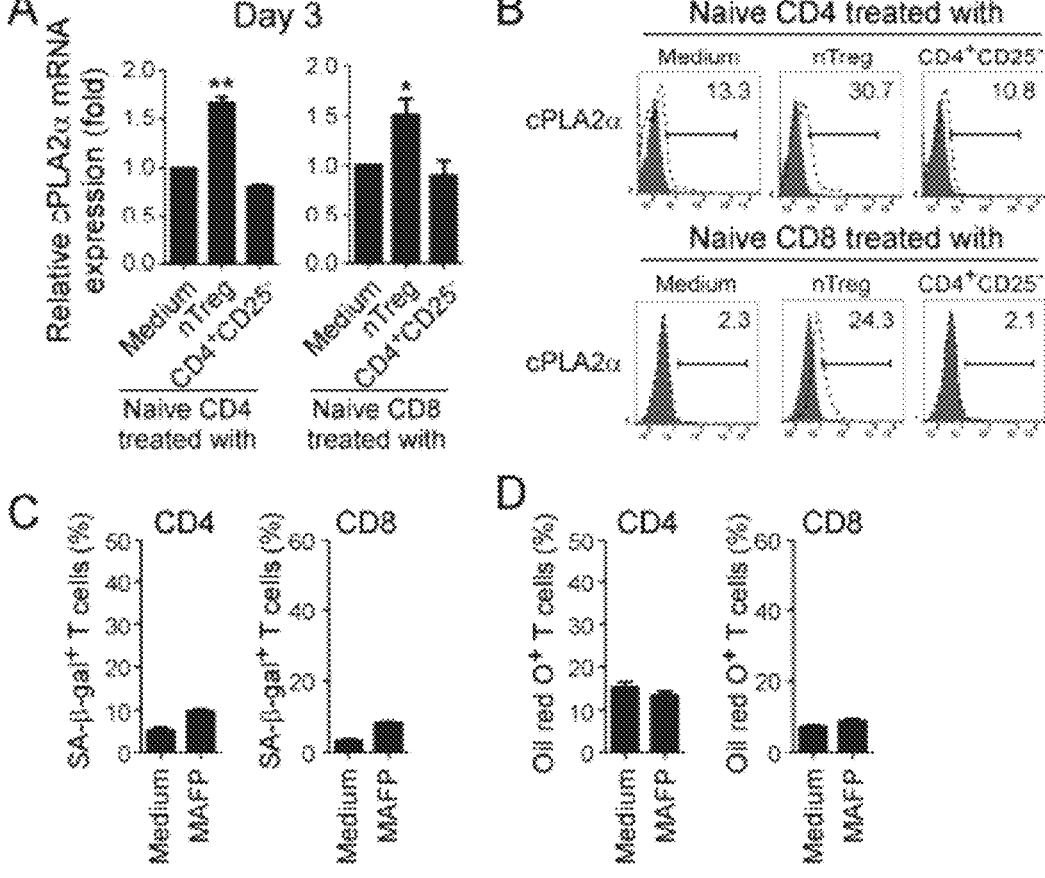

Elevated cPLA2α is responsible for the LD accumulation and senescence induction in T cells. Recent studies demonstrated that cPLA2α is critical for regulation of phospholipid metabolism and LD formation (Gubern et al., 2008; 2009; Guijas et al., 2012). The inventors therefore hypothesized that cPLA2α might be involved in the LD formation in T cells, resulting in T cell senescence and dysfunction during the cross-talks with Treg cells and tumor cells (FIG. 5A). The inventors first determined the kinetic alterations of cPLA2α mRNA levels in senescent T cells during the senescence induction mediated by Treg and tumor cells. The inventors observed obvious increases in cPLA2α levels in T cells during the progression to senescence and in already developed senescent T cells, mediated by both Treg cells and MCF-7 breast tumor cells (FIGS. 6A-B and FIG. 18A). Consistent with gene expression results, cPLA2α protein levels were also markedly elevated in senescent T cells induced by Treg cells using the western blot and flow cytometry analyses (FIG. 6C and FIG. 18B). In addition, the inventors evaluated the cPLA2α expression in T cells in vivo in the tumor microenvironment. The inventors purified T cells from blood and tumor tissues of the B16 and E0771-tumor bearing mice. The inventors observed that the cPLA2α mRNA expression levels in the tumor-infiltrating CD4+ and CD8+ T cells from both melanoma and breast tumor-bearing mice were higher than that of T cells purified from blood in control wild-type mice (FIGS. 6D-E). These results demonstrate that cPLA2α is elevated in senescent T cells in the tumor microenvironment.

To explore the causative role of the increased cPLA2α in the promotion of LD formation in senescent T cells, the inventors thus investigated the relationship of cPLA2α expression and LD formation in the senescent T cells induced by Treg cells using the immunofluorescence in situ analyses. The inventors observed significantly increased expression of cPLA2α in responder T cells treated with Treg cells, but not with control T cells (FIG. 6F). Furthermore, the cPLA2α expression was paralleled with the accumulated LDs in Treg-induced senescent T cells (FIG. 6F). The inventors determined whether blocking cPLA2α in T cells with cPLA2α specific pharmaceutical inhibitor MAFP can prevent LD formation in senescent T cells mediated by Treg cells (Gubern et al., 2008). Pretreatment of naïve CD4+ and CD8+ T cells with MAFP markedly decreased LD formation in responder T cells co-cultured with Treg cells (FIG. 6G). However, MAFP itself does not induce cell senescence and LD formation in naïve T cells (FIGS. 18C-D). The inventors then determined whether cPLA2α also regulates the altered lipid species in senescent T cells induced by Treg cells using a mass spectrometry-based lipidomics analysis as shown in FIGS. 4B and 4C. Pretreatment with MAFP dramatically reversed the down-regulation of phospholipids (SM, LPC and PC) and up-regulation of CE in senescent T cells induced by Treg cells (FIG. 6H). These results suggest a causative relationship between the increased cPLA2α and lipid metabolism during T cell senescence mediated by human Treg cells and tumor cells.

The inventors next determined whether the elevated cPLA2α is responsible for senescence induction in responder T cells induced by Treg cells. The inventors' previous studies have shown that senescent T cells induced by Treg cells and tumor cells have increased expression of cell cycle regulatory molecules p16, p21 and p53, and production of inflammatory cytokines and down-regulation of co-stimulatory molecules CD27 and CD28 [23,24,32,33]. The inventors found that blockade of cPLA2α with inhibitor MAFP significantly down-regulated cPLA2α expression in responder T cells induced by Treg cells (FIG. 6I). Furthermore, MAFP treatment not only inhibited the Treg-induced increases of p21 and p53 expression but also significantly prevented responder T cells from becoming senescent T cells mediated by Treg cells (FIGS. 6I and 6J). In addition, cPLA2α inhibition recovered the effector functions of senescent T cells induced by Treg cells, resulting in restoration of the lost co-stimulatory molecules CD27 and CD28, as well as suppression of inflammatory cytokine secretion in responder T cells (FIGS. 6K-L). Collectively, these studies suggested that cPLA2α is a key molecule that controls both lipid metabolism and cell fate in responder T cells mediated by Treg and tumor cells in the tumor suppressive microenvironment.

Figure 19:
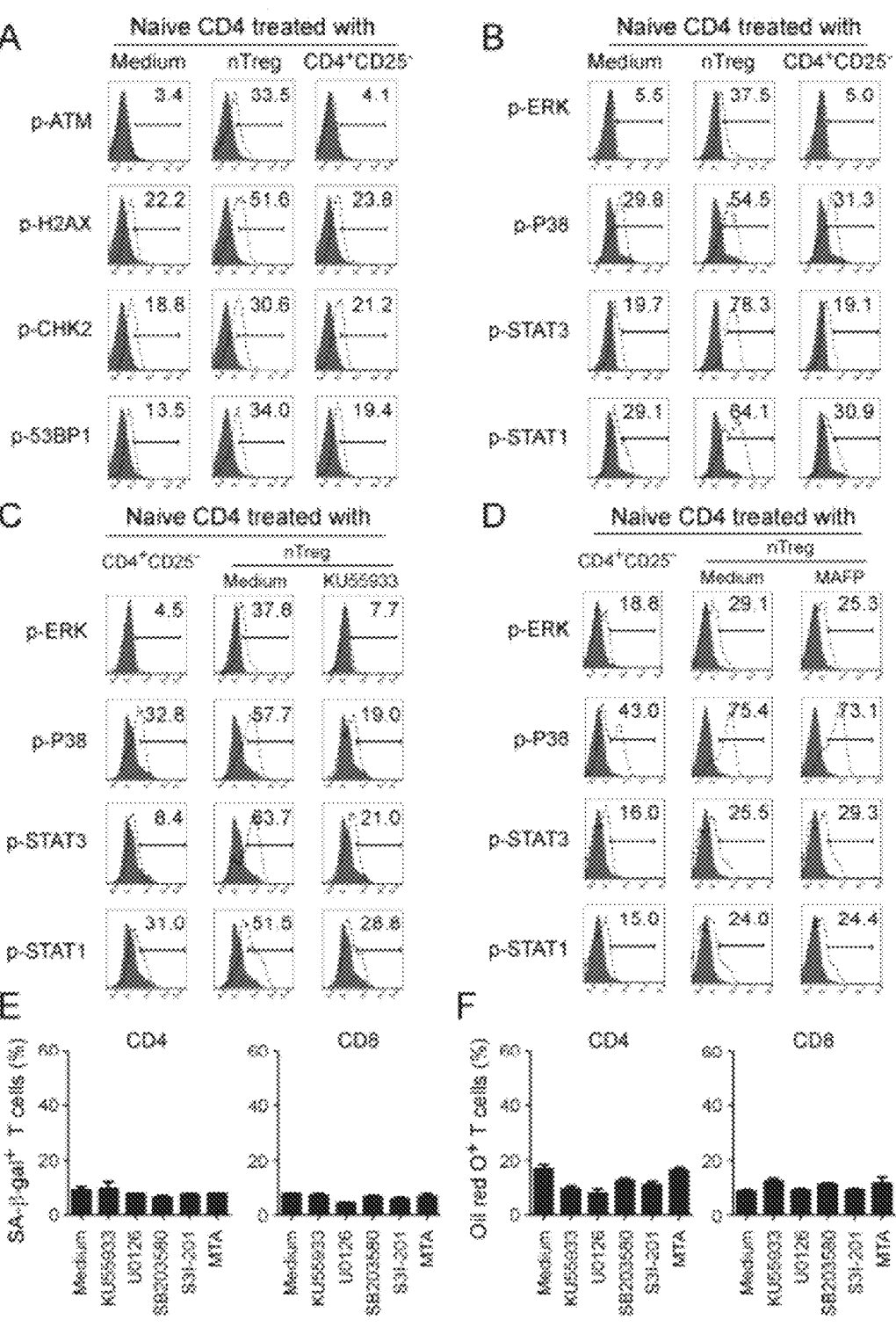

MAPK and STAT signaling coordinately control lipid metabolism and cPLA2α activity in responder T cells during T cell senescence. The inventors' recent studies have shown that initiation of ATM-associated DNA damage is the cause for T cell senescence and dysfunction induced by both human Treg cells and tumor cells (Liu et al., 2018; Ye et al., 2014). nTreg treatment significantly induced activation and phosphorylation of DNA damage molecules in responder CD4+ T cells, including ATM, H2AX, 53BP1, and CHK2 (FIG. 19A). The inventors therefore determined whether ATM-associated DNA damage is also causatively related to altered lipid metabolism in senescent T cells using the loss-of-function strategy. Functional blockage of ATM activation with the ATM-specific inhibitor KU55933 markedly prevented Treg-induced up-regulation of CE and FFA in senescent T cells (FIG. 7A). Furthermore, KU55933 treatment also significantly decreased both mRNA and protein expression of cPLA2α in Treg-induced senescent T cells (FIGS. 7B-C). In addition, blockage of ATM-associated DNA damage dramatically inhibited the accumulation and formation of LDs and prevented senescence induction in responder CD4+ and CD8+ T cells induced by Treg cells (FIGS. 7D-E). These results further confirm the mechanistic relationships among the DNA damage initiation, altered lipid metabolism and cell senescence in T cells during their cross-talk with Treg cells.

Figure 20:
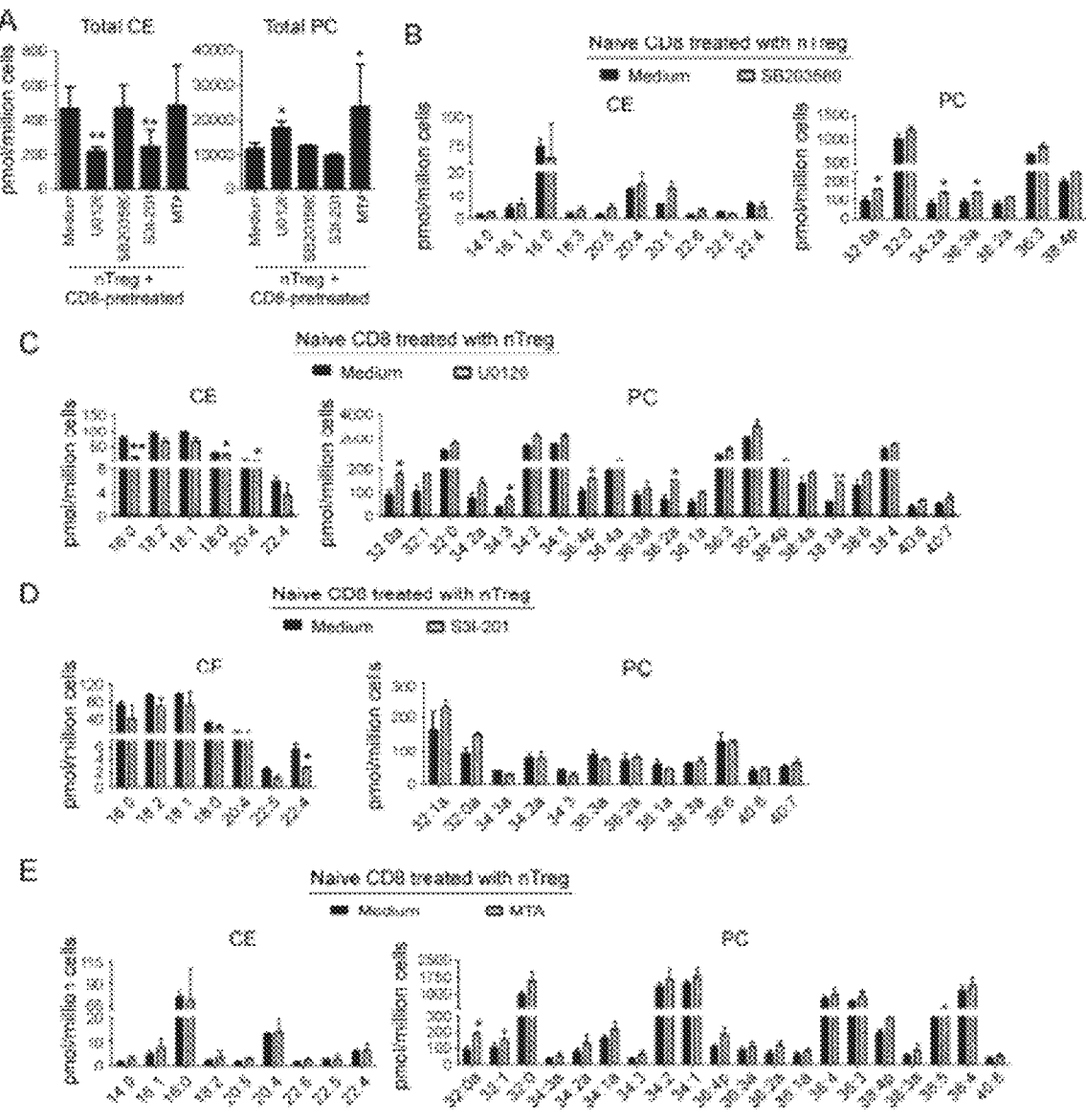

The inventors showed that both MAPK and STAT1/3 signaling pathways are involved in the regulation of Treg-induced T cell senescence (FIGS. 19B-C) (Liu et al., 2018; Ye et al., 2012). The inventors thus investigated how these two signaling pathways interact to control lipid metabolism in responder T cells treated by Treg cells, resulting in T cell senescence. The inventors first performed the immunofluorescence analysis to visualize the interaction and incorporation between MAPK signaling (phosphorated-p38 and -ERK) and STAT signaling (phosphorated-STAT1 and -STAT3), versus LD accumulation in Treg-induced senescent T cells. Consistent with the above results, the inventors found significantly increased phosphorylated activation of p38, ERK and STAT1 and STAT3 in responder T cells treated with Treg cells but not with control T cells (FIGS. 7F-G). Furthermore, senescent T cells also displayed a significant accumulation of LDs (Bodipy 493/503+) compared with the control T cells. In addition, the phosphorylated-p38, -ERK, -STAT1 and -STAT3 molecules were co-localized with LDs in Treg-induced senescent T cells, suggesting that these two signaling might be involved in regulation of LD formation during T cell senescence (FIGS. 7F-G). To further identify the causative role of these two signaling pathways in regulating altered phospholipids and LD formation in senescence T cells, the inventors functionally blocked the activities of MAPKs and STAT1/3 signaling in T cells, and then explored alterations of T cell lipid metabolism and senescence during the senescence development induced by Treg cells. As shown in FIGS. 20A-E, blockage of P38 and ERK signaling with respective inhibitors SB203580 and U0126, as well as STAT1/STAT3 signaling with respective inhibitors MTA and S3I-201 significantly prevented the Treg-induced up-regulation of CE and down-regulation of PC in senescent T cells. Furthermore, blockage of MAPK and STAT1/3 signaling with these inhibitors also dramatically suppressed the enhanced cPLA2α expression in Treg-induced senescent T cells (FIG. 7H). However, blockage of cPLA2α activity with MAFP did not inhibit the phosphorylation of MAPK ERK and P38, and STAT1/3 STAT3 in Treg-treated naïve CD4+ T cells, further suggesting that MAPK and STAT signaling directly control cPLA2 expression in T cells during T cell senescence (FIG. 20D). In addition, blockage of MAPK and STAT signaling significantly decreased Oil red O+ T cell populations (LD formation) and prevented senescence induction in responder T cells induced by Treg cells (FIGS. 7I-J). In contrast, these inhibitors themselves did not promote cell senescence and LD formation in naïve T cells (FIGS. 19E-F). These studies clearly indicate the causative relationships among ATM-associated DNA damage initiation, MAPK and STAT signaling activation, lipid metabolism regulation during the T cell senescence progression induced by human Treg cells.

Reversal of tumor-specific effector T cell senescence by inhibiting cPLA2α activation and LD formation enhances anti-tumor immunity in vivo in adoptive transfer therapy models. The inventors' studies suggest that preventing the generation of senescence and controlling the fate and function of tumor-specific T cells is critical for anti-tumor immunity (Liu et al., 2018; Ye et al., 2014; 2012; 2013; Ye and Peng, 2015). The current in vitro studies have indicated that accumulation of LDs induced by increased cPLA2α is a checkpoint for control of T cell senescence and function mediated by both tumor cells and Treg cells. Therefore, the inventors explored whether the inventors can manipulate cPLA2α activation and LD formation in effector T cells as a novel strategy for tumor immunotherapy. The inventors first utilized the well-established B16 melanoma and Pmel (gp100-specific) TCR Tg mouse models to test their hypothesis (Abad et al., 2008). Pre-activated gp100-specific CD8+ T cells were adoptively transferred into B16F10-bearing mice through i.v. injection at day 6 after tumor cell inoculation. MAFP (7.5 mg kg-1/mouse) was injected intraperitoneally into the mice every 3 days for a total of 4 injections following the adoptive transfer of the T cells. Tumor growth was evaluated. Furthermore, the adoptively transferred gp 100-specific CD8+ T cells were purified and recovered from different groups and organs at the end of experiments, and further analyzed for the effects of the MAFP treatment on LD formation and senescence induction.

Figure 21:
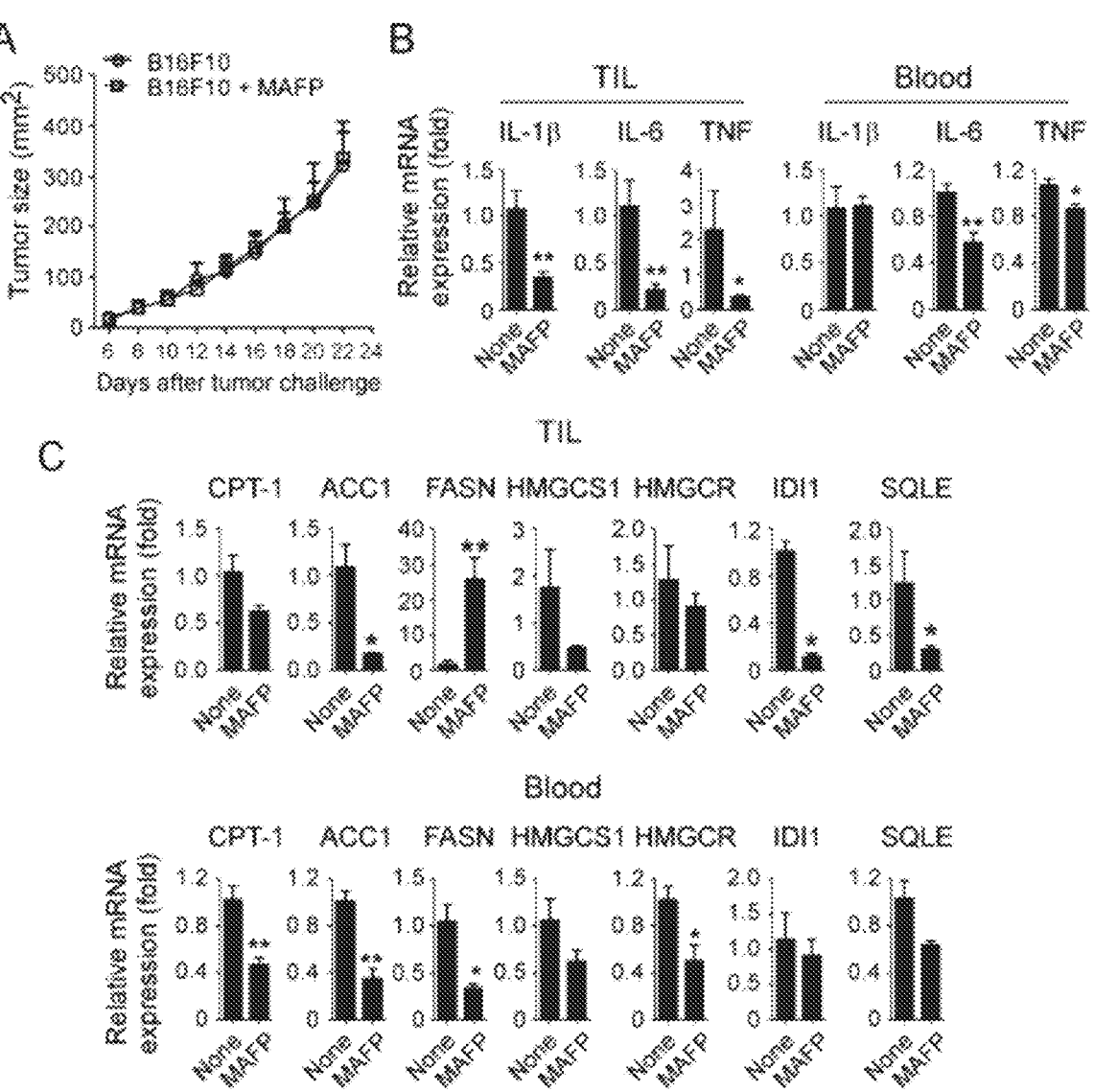

B16F10 tumor cells grew very fast in mice. When tumor-specific Pmel-1 T cells were adoptively transferred into mice, tumor growth was inhibited. Importantly, MAFP treatment dramatically promoted the inhibition of tumor growth mediated by gp100-specific CD8+ T cells (FIG. 8A). However, MAFP treatment alone did not have significant effects on tumor growth (FIG. 21). These results clearly suggest that MAFP treatment enhances the anti-tumor ability mediated by tumor-specific effector T cells rather than directly suppressing tumor growth. The inventors confirmed the molecular changes of recovered tumor-specific T cells in vivo from different organs and tumors after MAFP treatment. Consistent with the results shown in in vitro studies, the inventors observed that administration of MAFP strongly inhibited gene expression of cPLA2α in recovered gp100-specific CD8+ T cells in vivo (FIG. 8B). Furthermore, MAFP treatment markedly down-regulated gene expression levels of inflammatory cytokines and enzymes related to lipid metabolism in recovered T cells (FIGS. 21B-C). In addition, MAFP treatment also dramatically decreased LD formation and prevented cell senescence in purified gp100-specific CD8+ T cells from blood, lymph nodes, spleens, as well as in tumor tissues from B16F10-bearing mice (FIGS. 8C-D).

The inventors then extended the studies in B16 melanoma to the E0771 breast cancer model. E0771 tumor cells were transduced with retroviral vector encoding tumor antigen gp100 and then combined with Pmel-1 T cells for the adoptive cell transfer therapy. As expected, the inventors obtained very similar results as shown in the B16 melanoma model. The adoptively transferred tumor-specific Pmel-1 T cells suppressed E0771/gp-100 tumor growth. Furthermore, MAFP administration significantly enhanced anti-tumor capacity mediated by Pmel-1 T cells against the E0771/gp-100 tumor (FIG. 8E). In addition, MAFP treatment significantly decreased the SA-β-gal+ and Oil-red O+ T cell populations in the recovered gp-100 CD8+ T cells from blood, spleen and TILs in E0771-bearing mice, confirming the decreases of LD formation and cell senescence in tumor-specific T cells (FIGS. 8F-G). These results indicate that inhibition of cPLA2 in tumor-specific T cells can reprogram lipid metabolism, reverse T cell senescence and dysfunction in the tumor microenvironment and enhance anti-tumor immune responses.

The inventors further investigated the potential translation of this novel concept that inhibition of cPLA2α for reprogramming lipid metabolism in tumor-specific T cells could be an effective strategy for tumor immunotherapy. The inventors first determined whether this strategy also can enhance T cell-mediated anti-tumor immunity in the late stage of cancer development. The inventors adoptively transferred Pmel-1 Tg T cells after B16 tumor grew to a larger size (over 8×8 mm), and then administered MAFP using the identical procedures as above. The inventors found that inhibition of cPLA2α activity with MAFP also can promote the therapeutic efficacy of adoptively transferred T cells in the late stage B16 melanoma mice (FIG. 8H). In addition to the mouse tumor models, the inventors further investigated whether reprogramming of effector T cell lipid metabolism via cPLA2α inhibition can enhance anti-tumor immunity in the adoptive transfer human T cell immunotherapy melanoma model in humanized NSG mice (Ye et al., 2014; Peng et al., 2005; 2007). Human 586mel tumor cells were subcutaneously injected into humanized NSG mice on day 0. Tumor-specific CD8+ TIL586 T cells (which recognize and kill autologous 586mel tumor cells) were adoptively transferred through i.v. injection on day 5, followed by intraperitoneal injection of MAFP. Consistent with the inventors' previous studies, they found that 586 melanoma cells grew progressively in NSG mice. Adoptive transfer of tumor-specific CD8+ TIL586 T cells significantly inhibited tumor growth. Importantly, MAFP treatment strongly promoted the inhibition of tumor growth mediated by tumor-specific TIL586 T cells, suggesting that MAFP treatment enhances anti-tumor ability mediated by TIL586 cells (FIG. 8I). In addition, MAFP injection markedly decreased LD formation and prevented cell senescence in tumor-specific TIL586 T cells (FIGS. 8J-K). Collectively, these in vivo studies strongly suggest that reprogramming of lipid metabolism in tumor-specific T cells via cPLA2α inhibition can prevent T-cell senescence and enhance subsequent anti-tumor immune responses, which is a novel and effective strategy for tumor immunotherapy.

Example 3—Discussion

Tumor-specific T cells are suppressed and dysfunctional in the tumor suppressive microenvironment, which is a major obstacle for successful tumor immunotherapy 4. Tumor microenvironment can reprogram T cell metabolism, directing T cell survival, proliferation and functional states (Thommen & Schumacher, 2018; Huang et al., 2018; Zhang and Romero, 2018; Kouidhi et al., 2017; Lyssiotis and Kimmelman; 2017). The inventors' current and previous studies have clearly demonstrated that T cell senescence induced by both malignant tumor cells and Treg cells is a general feature in different types of cancers (Liu et al., 2018; Ye et al., 2014; 2012; 2013; Ye and Peng, 2015). In this study, the inventors further demonstrate that tumor and Treg cells rewrite lipid metabolism in T cells resulting in T cell senescence and dysfunctional immunity in the tumor microenvironment. Molecularly, MAPK and STAT1/STAT3 signaling pathways cooperate to promote cPLA2α expression in responder T cells, resulting in alterations of lipid metabolism, LD accumulation and senescence development. Importantly, using T cell adoptive transfer immunotherapy models, the inventors further establish the novel concept that reprogramming lipid metabolism in T cells within the tumor microenvironment is a potential and novel immunotherapeutic strategy for cancer treatment.

Malignant tumors can utilize various strategies to metabolically modify T cell functionality for anti-tumor immunity and immunotherapy, including direct competition for glucose consumption, through the metabolite regulation, inhibition of Glut1 and glycolysis through checkpoint molecules, and decrease of mitochondrial biogenesis and function, (Thommen and Schumacher, 2018; Chang et al., 2015; Huang et al., 2018; Zhang and Romero, 2018; Kouidhi et al., 2017; Sukumar et al., 2015; Beckermann et al., 2017; Zhao et al., 2016; Patsoukis et al., 2015; Bengsch et al., 2016; Scharping et al., 2016; Lyssiotis and Kimmelman, 2017; Xia et al., 2017; Sitkovsky et al., 2008). However, the metabolic profiles of TILs induced by cancer cells and Treg cells have not been fully characterized. Understanding these interactive effects is critical for the development of effective immunotherapeutic strategies against cancer. In the current study, the inventors characterized the key metabolic genes involving glucose metabolism in TILs form cancer patients and tumor-bearing mice of melanoma and breast cancer, as well as responder T cells cultured with cancer cells and Treg cells, using transcriptome and real-time quantitative PCR analyses. The inventors' studies clearly suggest that TILs from both human cancer patients and tumor-bearing mice possess very active glucose metabolism to maintain their biological and functional demands. In contrast to glucose metabolism, the TILs and co-cultured T cells with tumor and/or Treg cells exhibit altered lipid metabolism. More recent studies have demonstrated that T cells with increased cholesterol esterification have impaired proliferation and anti-tumor effector function (Yang et al., 2016). However, little is known about the causative relationships between lipid metabolism and T cell dysfunction in the tumor suppressive microenvironment. The current studies collectively indicate that tumor cells and Treg cells can rewrite T cell lipid metabolism, cell fate and function through different molecular levels. First, both tumor cells and Treg cells induce dynamic expression levels of the key enzymes important for cholesterol synthesis, and fatty acid oxidation and synthesis, in senescent CD4+ and CD8+ T cells. Eventually, all the lipid-related enzymes are inhibited in the TILs or in the T cells induced by both tumor and Treg cells. Second, both tumor and Treg cells alter the lipid species/components in responder T cells or/and TILs, showing increases of CE and FFA, but losses of key phospholipids. Importantly, all these altered lipid species are critical for the development of T cell senescence and dysfunction mediated by tumor cells and Treg cells. The inventors' studies further demonstrate that the altered lipid species/components promote development of LDs in responder T cells or TILs. In addition, the inventors identified that accumulation of LDs in T cells induced by Treg and tumor cells is strongly associated with the development of T cell senescence and impaired functions. Collectively, these studies identify causative links between T cell lipid metabolism reprogramming and the molecular processes important for T cell fate and function in the tumor microenvironment.

LDs are lipid-rich cytoplasmic organelles and also important for the regulation of inflammation and cancer (Yang et al., 2016; Fujimoto and Parton, 2011; Guijas et al., 2014). Recent studies have shown that LDs accumulate in tumor-derived DCs, which results in DC tolerogenic functions (Ramakrishan et al., 2014; Herber et al., 2010). However, little information is known about whether LDs regulate T cell function in anti-tumor immunity. TAG and CE are the key components for the neutral lipid cores of LDs (Fujimoto and Parton, 2011; Penno et al., 2013). In this study, the inventors identified accumulation of LDs in both TILs from human cancer patients and tumor-bearing mice in melanoma and breast cancer, as well as in senescent T cells induced by tumor and Treg cells. The inventors further identified the molecular mechanism responsible for the increase of LDs in senescent T cells in the tumor microenvironment. These studies suggest that ACAT is not involved in the increased LDs in the senescence T cells. However, the down-regulated LAL and increased cPLA2α appear to be key molecular processes that control both LD formation and cell fate in responder T cells mediated by Treg and tumor cells. The current studies did not investigate the effects of TAG changes in TILs and in senescent T cells mediated by tumor cells and Treg cells. In addition, the inventors have not determined how loss of phospholipids is involved in the development of T cell senescence. Future studies will need to further dissect the causative cross-talks among these regulations in lipid metabolism and T cell functions in anti-tumor immunity.

The current study has addressed another key question of how the tumor microenvironment molecularly promotes the development of T cell senescence via metabolic reprogramming. Increasing evidence suggests that immunosenescence is another important state of T cell dysfunction in the tumor microenvironment, which is distinct from exhaustion and anergy (Liu et al., 20018; Ye et al., 2014; 2012; 2013; Ye and Peng, 2015). Accumulated senescent CD8+ T cells have been found in TILs from various types of cancer patients (Gruber et al., 2008; Urbaniak-Kujda et al., 2009; Meloni et al., 2006). However, the molecular mechanisms and signaling pathways responsible for T cell senescence in the tumor microenvironment remain unclear. The causative relationships between tumor-mediated metabolic changes and senescent T cell development are unknown. The inventors' recent studies have demonstrated that tumor-derived metabolite cAMP produced by multiple types of tumor cells can directly induce T cell senescence (Ye et al., 2014; Ye and Peng, 2015). In addition, tumor-associated Treg cells can trigger cell senescence and DNA damage in responder T cells through competitive glucose consumption (Liu et al., 2018; Ye et al., 2012; 2013). In the current studies, the inventors show that senescent T cells induced by tumor cells and Treg cells exhibit very active glucose metabolism and inflammatory cytokine secretion. These results were further confirmed in the TILs from both human cancer patients and tumor-bearing mice in melanoma and breast cancer. In support of these results with T cells, studies from other types of senescent cells suggest that senescent cells have permanent cell cycle arrest but exhibit active metabolism with elevated glycolysis during senescence (James et al., 2015; Liao et al., 2014; Takebayashi et al., 2015). These studies clearly indicate that T cells within tumors are functional and metabolically active, not exhausted and/or anergic, and are important amplifiers for maintenance of the tumor suppressive microenvironment (Liu et al., 2018; Ye et al., 2014; 2012; 2013; Ye and Peng, 2015. These findings might also explain why the checkpoint blockage therapy using antibodies to target PD1/PDL1 or/and CTLA4 have had only limited success rates in cancer patients (Topalian et al., 2015; Sharma and Allison, 2015; Rosenberg and Restifo, 2015). In addition to glucose metabolism, lipid metabolism is important for cellular senescence (Ford, 2010; Wiley and Campisi, 2016; Lizardo et al., 2017). The current studies have identified lipid metabolism alterations in T cells induced by tumor cells and Treg cells, and strongly suggest these changes are the cause for T cell senescence and dysfunction in the tumor microenvironment. Studies from the inventors and others have shown that MAPK signaling pathway controls human T cell senescence and can also regulate cPLA2α activation (Liu et al., 2018; Gubern et al., 2008; Lanna et al., 2014; 2017; Perez-Chacon et al., 2009). In this study, the inventors further demonstrate that the activated MAPK p38/ERK and STAT signaling pathways, which are initiated by the ATM-associated DNA damage response, promote cPLA2α activation and function in T cells, resulting in LD formation/accumulation and cell senescence in responder T cells mediated by Treg and tumor cells. These studies not only define the unique molecular mechanisms and signaling pathways that control the differentiation of senescent T cells mediated by malignant tumors, but also identify a mechanism potentially responsible for failure of checkpoint blockade immunotherapy, as well as provide alterative therapeutic strategies for cancer patients.

These studies provide a novel proof-of-concept that reprogramming T cell lipid metabolism to prevent senescence in effector T cells induced by Treg cells and tumor cells may lead to effective therapeutic strategies for enhanced immunotherapy. Importantly, the inventors have identified that cPLA2α is a key target involved in regulations of lipid metabolism, cell senescence and functions in T cells important for tumor immunotherapy. The inventors' in vivo studies clearly demonstrate that reprogramming of T cell lipid metabolism via cPLA2α inhibition significantly prevents effector T cell senescence and dysfunction, resulting in enhanced anti-tumor immunity and immunotherapeutic efficacy of adoptively transferred T cells in melanoma and breast cancer models with both early and late stages. The inventors' hypothesis and concept are strongly supported by a recent study showing that modulation of CD8+ T cell cholesterol metabolism can enhance cancer immunotherapy Yang et al., 2016). The inventors' previous studies have demonstrated that activation of human Toll-like receptor 8 (TLR8) signaling in Treg cells and multiple types of tumor cells can prevent effector T cell senescence and reverse the suppressive activity mediated by both Treg and senescent T cells (Ye et al., 2014; 2012; 2013; Li et al., 2019; Peng et al., 2005; 2007). These strategies manipulating T cell metabolism and senescence, combined with the immune checkpoint therapies such as CTLA-4 or PD1 blockade therapy, may yield more promising results for improved cancer immunotherapy (Topalian et al., 2015; Sharma and Allison, 2015; Zou et al., 2016).

In summary, this current study provides evidence that development of cell senescence is an important dysfunctional state for T cells within the tumor suppressive microenvironment. Treg cells and tumor cells reprogram lipid metabolism in responder T cells and promote T cell senescence and dysfunction. Furthermore, elevated cPLA2α induced by tumor and Treg cells is mechanistically important for the altered lipid metabolism and senescence induction in T cells, molecularly controlled by MAPK and STAT signaling (FIG. 22). In addition, these studies provide proof-of-concept for therapeutic reprogramming of T cell lipid metabolism for the control of T cell function and enhanced anti-tumor immunity.

SUPPLEMENTAL TABLE 1

| Primers used for Real-time quantitative RT-PCR | |
| --- | --- |
| Genes | Primers |
| Hu-IL-1β Forward | ACAGATGAAGTGCTCCTTCCA |
| Hu-IL-1β Reverse | GTCGGAGATTCGTAGCTGGAT |
| Hu-IL-2 Forward | GTCACAAACAGTGCACCTAC |
| Hu-IL-2 Reverse | CCCTGGGTCTTAAGTGAAAG |
| Hu-IL-6 Forward | GTAGCCGCCCCACACAGA |
| Hu-IL-6 Reverse | CATGTCTCCTTTCTCAGGGCT |
| Hu-IL-8 Forward | ATAAAGACATACTCCAAACCTTTCCAC |
| Hu-IL-8 Reverse | AAGCTTTACAATAATTTCTGTGTTGGC |
| Hu-TNF Forward | GGAGAAGGGTGACCGACTCA |
| Hu-TNF Reverse | CTGCCCAGACTCGGCAA |
| Hu-IFN-γ Forward | AAGAGTGTGGAGACCATCA |
| Hu-IFN-γ Reverse | TGCTCTTCGACCTTGAAACA |
| Hu-Glut1 Forward | ATTGGCTCCGGTATCGTCAAC |
| Hu-Glut1 Reverse | GCTCAGATAGGACATCCAGGGTA |
| Hu-Glut3 Forward | GCTCTCTGGGATCAATGCTGTGT |
| Hu-Glut3 Reverse | CTTCCTGCCCTTTCCACCAGA |
| Hu-HK2 Forward | AACAGCCTGGACGAGAGCAT |
| Hu-HK2 Reverse | GCCAACAATGAGGCCAACTT |
| Hu-GPI Forward | GATGGTAGCTCTCTGCAGCC |
| Hu-GPI Reverse | GCCATGGCGGGACTCTTG |
| Hu-PFK Forward | GGCAGCCATGCATAAAGACG |
| Hu-PFK Reverse | AAGCTTCCCCAGCTGTTCTC |
| Hu-TPI Forward | AGGCATGTCTTTGGGGAGTC |
| Hu-TPI Reverse | AGTCCTTCACGTTATCTGCGA |
| Hu-ENO1 Forward | CGCCTTAGCTAGGCAGGAAG |
| Hu-ENO1 Reverse | GGTGAACTTCTAGCCACTGGG |
| Hu-PKM2 Forward | ACGAGAACATCCTGTGGCTG |
| Hu-PKM2 Reverse | AGGAAGTCGGCACCTTTCTG |
| Hu-LDHα Forward | AGCTGTTCCACTTAAGGCCC |
| Hu-LDHα Reverse | TGGAACCAAAAGGAATCGGGA |
| Hu-CPT1 Forward | ATCAATCGGACTCTGGAAACGG |
| Hu-CPT1 Reverse | TCAGGGAGTAGCGCATGGT |
| Hu-ACC1 Forward | TCACACCTGAAGACCTTAAAGCC |

SUPPLEMENTAL TABLE 1-continued

| Primers used for Real-time quantitative RT-PCR | |
| --- | --- |
| Genes | Primers |
| Hu-ACC1 Reverse | AGCCCACACTGCTTGTACTG |
| Hu-FASN Forward | ACAGCGGGGAATGGGTACT |
| Hu-FASN Reverse | GACTGGTACAACGAGCGGAT |
| Hu-HMGCR Forward | GTGAGATCTGGAGGATCCAAGG |
| Hu-HMGCR Reverse | GATGGGAGGCCACAAAGAGG |
| Hu-HMGCS1 Forward | GTTGGCGGCTATAAAGCTGGT |
| Hu-HMGCS1 Reverse | CCTTCGGGCACAAGCG |
| Hu-SQLE Forward | TGACAATTCTCATCTGAGGTCCA |
| Hu-SQLE Reverse | TCCCAAAAGAAGAACACCTCGT |
| Hu-IDI1 Forward | CGGAGGCTGATCAGTGTTCTA |
| Hu-IDI1 Reverse | TGTTGCTTGTCGAGGTGGTT |
| Hu-ACAT1 Forward | TACCAGAAGTAAAGCAGCATGG |
| Hu-ACAT1 Reverse | TCATTCAGTGTACTGGCATTGG |
| Hu-ACAT2 Forward | GCGGACCATCATAGGTTCCTT |
| Hu-ACAT2 Reverse | ACTGGCTTGTCTAACAGGATTCT |
| Hu-LIPA Forward | CCCACGTTTGCACTCATGTC |
| Hu-LIPA Reverse | CCCAGTCAAAGGCTTGAAACTT |
| Hu-cPLA2α Forward | AATACTGCACAATGCCCTTTACC |
| Hu-cPLA2α Reverse | GCTTCCAAATAAGTCGGGAGC |
| Hu-β-actin Forward | TGGCACCCAGCACAATGAA |
| Hu-β-actin Reverse | CTAAGTCATAGTCCGCCTAGAAGCA |
| Hu-GAPDH Forward | AGCCGCATCTTCTTTTGCGTCG |
| Hu-GAPDH Reverse | GACCAGGCGCCCAATACG |
| Mu-IL-1β Forward | GGGCCTCACAGGAAAGAATC |
| Mu-IL-1β Reverse | GGGGAACTCTGCAGACTCAA |
| Mu-IL-2 Forward | TCCAGAACATGCCGCAGAG |
| Mu-IL-2 Reverse | CCTGAGCAGGATGGAGAATTACA |
| Mu-IL-6 Forward | GTTCTCTGGGAAATCGTGGA |
| Mu-IL-6 Reverse | TGTACTCCAGGTAGCTATGG |
| Mu-TNF Forward | ACCCTCACACTCAGATCATC |
| Mu-TNF Reverse | GAGTAGACAAGGTACAACCC |
| Mu-IFN-γ Forward | ATGAACGCTACACACTGCATC |
| Mu-IFN-γ Reverse | CCATCCTTTTGCCAGTTCCTC |
| Mu-Glut1 Forward | CAGTTCGGCTATAACACTGGTG |
| Mu-Glut1 Reverse | GCCCCCGACAGAGAAGATG |
| Mu-Glut3 Forward | CTTTGGCAGACGCAACTCTAT |
| Mu-Glut3 Reverse | ACCAGAATCCCAACAACGATG |
| Mu-HK2 Forward | TGATCGCCTGCTTATTCACGG |

SUPPLEMENTAL TABLE 1-continued

| Genes | Primers |
|---|---|
| | Primers used for Real-time quantitative RT-PCR |
| Mu-HK2 Reverse | AACCGCCTAGAAATCTCCAGA |
| Mu-GPI Forward | TCCCCTGAGACTTCCCTCTTT |
| Mu-GPI Reverse | CGAGAAACCACTCCTTTGCTG |
| Mu-PFK Forward | TGTGGTCCGAGTTGGTATCTT |
| Mu-PFK Reverse | GCACTTCCAATCACTGTGCC |
| Mu-TPI Forward | CCAGGAAGTTCTTCGTTGGGG |
| Mu-TPI Reverse | CAAAGTCGATGTAAGCGGTGG |
| Mu-ENO1 Forward | AGAGTGGGAGGCGCTTAGT |
| Mu-ENO1 Reverse | ATGGCGAATTTCTGGCAGTAG |
| Mu-PKM2 Forward | GTGGCTCGGCTGAATTTCTCT |
| Mu-PKM2 Reverse | CACCGCAACAGGACGGTAG |
| Mu-LDH Forward | TGTCTCCAGCAAAGACTACTGT |
| Mu-LDH Reverse | GACTGTACTTGACAATGTTGGGA |
| Mu-HMGCR Forward | TCTTGTGGAATGCCTTGTGATT |
| Mu-HMGCR Reverse | GGGTTACGGGGTTTGGTTTAT |
| Mu-HMGCS1 Forward | AACTGGTGCAGAAATCTCTAGC |
| Mu-HMGCS1 Reverse | GGTTGAATAGCTCAGAACTAGCC |
| Mu-SQLE Forward | GCTGGGCCTTGGAGATACAG |
| Mu-SQLE Reverse | CAGTGGGTACGGAATTTGAACT |
| Mu-IDI Forward | CGAACCCTCCTCAAGAAGCC |
| Mu-IDI Reverse | CCTAGAACACAGAGATTCCGGC |
| Mu-CPT1 Forward | AGATCAATCGGACCCTAGACAC |
| Mu-CPT1 Reverse | CAGCGAGTAGCGCATAGTCA |
| Mu-ACC1 Forward | AATGAACGTGCAATCCGATTTG |
| Mu-ACC1 Reverse | ACTCCACATTTGCGTAATTGTTG |
| Mu-FASN Forward | GGCTCTATGGATTACCCAAGC |
| Mu-FASN Reverse | CCAGTGTTCGTTCCTCGGA |
| Mu-ACAT1 Forward | CAACACTGGGCGCAGGTTTA |
| Mu-ACAT1 Reverse | GCCCGTCTTTTACAATCAGGTCT |
| Mu-ACAT2 Forward | CCCAGGACAAGGTTGCAGTT |
| Mu-ACAT2 Reverse | CGTTCATTCCTGATGCGTTCG |
| Mu-cPLA2α Forward | CAGCACATTATAGTGGAACACCA |
| Mu-cPLA2α Reverse | AGTGTCCAGCATATCGCCAAA |
| Mu-β-actin Forward | GATCAAGATCATTGCTCCTCCTG |
| Mu-β-actin Reverse | AGGGTGTAAAACGCAGCTCA |
| Mu-GAPDH Forward | GGGTTCCTATAAATACGGACTGC |
| Mu-GAPDH Reverse | ATGAAGGGGTCGTTGATGGC |

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. REFERENCES

The following references, to the extent that they provide exemplary procedural or other details supplementary to those set forth herein, are specifically incorporated herein by reference.

Topalian, S. L., Drake, C. G. & Pardoll, D. M. Immune checkpoint blockade: a common denominator approach to cancer therapy. *Cancer Cell* 27, 450-461, doi: 10.1016/j.ccell.2015.03.001 (2015).

Sharma, P. & Allison, J. P. Immune checkpoint targeting in cancer therapy: toward combination strategies with curative potential. *Cell* 161, 205-214, doi: 10.1016/j.cell.2015.03.030 (2015).

Rosenberg, S. A. & Restifo, N. P. Adoptive cell transfer as personalized immunotherapy for human cancer. *Science* 348, 62-68, doi: 10.1126/science.aaa4967 (2015).

Thommen, D. S. & Schumacher, T. N. T Cell Dysfunction in Cancer. *Cancer Cell* 33, 547-562, doi: 10.1016/j.ccell.2018.03.012 (2018).

Zou, W., Wolchok, J. D. & Chen, L. PD-L1 (B7-H1) and PD-1 pathway blockade for cancer therapy: Mechanisms, response biomarkers, and combinations. *Science translational medicine* 8, 328rv324, doi: 10.1126/scitranslmed.aad7118 (2016).

Baitsch, L. et al. Exhaustion of tumor-specific CD8 (+) T cells in metastases from melanoma patients. *J Clin Invest* 121, 2350-2360, doi: 10.1172/JCI46102 (2011).

Fourcade, J. et al. Upregulation of Tim-3 and PD-1 expression is associated with tumor antigen-specific CD8+ T cell dysfunction in melanoma patients. *J Exp Med* 207, 2175-2186, doi: 10.1084/jem.20100637 (2010).

Macintyre, A. N. et al. The glucose transporter Glut1 is selectively essential for CD4 T cell activation and effector function. *Cell metabolism* 20, 61-72, doi: 10.1016/j.cmet.2014.05.004 (2014).

Pearce, E. L. Metabolism in T cell activation and differentiation. *Current opinion in immunology* 22, 314-320, doi: 10.1016/j.coi.2010.01.018 (2010).

Zeng, H. & Chi, H. Metabolic control of regulatory T cell development and function. *Trends in immunology* 36, 3-12, doi: 10.1016/j.it.2014.08.003 (2015).

MacIver, N. J., Michalek, R. D. & Rathmell, J. C. Metabolic regulation of T lymphocytes. *Annual review of immunology* 31, 259-283, doi: 10.1146/annurev-immunol-032712-095956 (2013).

Michalek, R. D. et al. Cutting edge: distinct glycolytic and lipid oxidative metabolic programs are essential for effector and regulatory CD4+ T cell subsets. *J Immunol* 186, 3299-3303, doi: 10.4049/jimmunol. 1003613 (2011).

Chang, C. H. et al. Posttranscriptional control of T cell effector function by aerobic glycolysis. *Cell* 153, 1239-1251, doi: 10.1016/j.cell.2013.05.016 (2013).

Chang, C. H. et al. Metabolic Competition in the Tumor Microenvironment Is a Driver of Cancer Progression. *Cell* 162, 1229-1241, doi: 10.1016/j.cell.2015.08.016 (2015).

Sinclair, L. V. et al. Control of amino-acid transport by antigen receptors coordinates the metabolic reprogramming essential for T cell differentiation. *Nat Immunol* 14, 500-508, doi: 10.1038/ni.2556 (2013).

Angela, M. et al. Fatty acid metabolic reprogramming via mTOR-mediated inductions of PPARgamma directs early activation of T cells. *Nature communications* 7, 13683, doi: 10.1038/ncomms13683 (2016).

Huang, L., Xu, H. & Peng, G. TLR-mediated metabolic reprogramming in the tumor microenvironment: potential novel strategies for cancer immunotherapy. *Cellular & molecular immunology* 15, 428-437, doi: 10.1038/cmi.2018.4 (2018).

Zhang, L. & Romero, P. Metabolic Control of CD8 (+) T Cell Fate Decisions and Antitumor Immunity. *Trends in molecular medicine* 24, 30-48, doi: 10.1016/j.molmed.2017.11.005 (2018).

Kouidhi, S., Elgaaied, A. B. & Chouaib, S. Impact of Metabolism on T-Cell Differentiation and Function and Cross Talk with Tumor Microenvironment. *Frontiers in immunology* 8, 270, doi: 10.3389/fimmu.2017.00270 (2017).

Sukumar, M., Roychoudhuri, R. & Restifo, N. P. Nutrient Competition: A New Axis of Tumor Immunosuppression. *Cell* 162, 1206-1208, doi: 10.1016/j.cell.2015.08.064 (2015).

Beckermann, K. E., Dudzinski, S. O. & Rathmell, J. C. Dysfunctional T cell metabolism in the tumor microenvironment. *Cytokine & growth factor reviews* 35, 7-14, doi: 10.1016/j.cytogfr.2017.04.003 (2017).

Zhao, E. et al. Cancer mediates effector T cell dysfunction by targeting microRNAs and EZH2 via glycolysis restriction. *Nat Immunol* 17, 95-103, doi: 10.1038/ni.3313 (2016).

Liu, X. et al. Regulatory T cells trigger effector T cell DNA damage and senescence caused by metabolic competition. *Nature communications* 9, 249, doi: 10.1038/s41467-017-02689-5 (2018).

Ye, J. et al. TLR8 signaling enhances tumor immunity by preventing tumor-induced T-cell senescence. *EMBO molecular medicine* 6, 1294-1311, doi: 10.15252/emmm.201403918 (2014).

Patsoukis, N. et al. PD-1 alters T-cell metabolic reprogramming by inhibiting glycolysis and promoting lipolysis and fatty acid oxidation. *Nature communications* 6, 6692, doi: 10.1038/ncomms7692 (2015).

Bengsch, B. et al. Bioenergetic Insufficiencies Due to Metabolic Alterations Regulated by the Inhibitory Receptor PD-1 Are an Early Driver of CD8 (+) T Cell Exhaustion. *Immunity* 45, 358-373, doi: 10.1016/j.immuni.2016.07.008 (2016).

Scharping, N. E. et al. The Tumor Microenvironment Represses T Cell Mitochondrial Biogenesis to Drive Intratumoral T Cell Metabolic Insufficiency and Dysfunction. *Immunity* 45, 701-703, doi: 10.1016/j.immuni.2016.08.009 (2016).

Atilla-Gokcumen, G. E. et al. Dividing Cells Regulate Their Lipid Composition and Localization. *Cell* 156, 428-439, doi: 10.1016/j.cell.2013.12.015 (2014).

Magtanong, L., Ko, P. J. & Dixon, S. J. Emerging roles for lipids in non-apoptotic cell death. *Cell death and differentiation* 23, 1099-1109, doi: 10.1038/cdd.2016.25 (2016).

Ramakrishnan, R. et al. Oxidized lipids block antigen cross-presentation by dendritic cells in cancer. *J Immunol* 192, 2920-2931, doi: 10.4049/jimmunol. 1302801 (2014).

Herber, D. L. et al. Lipid accumulation and dendritic cell dysfunction in cancer. *Nat Med* 16, 880-886, doi: 10.1038/nm.2172 (2010).

Ye, J. et al. Human regulatory T cells induce T-lymphocyte senescence. *Blood* 120, 2021-2031, doi: blood-2012-03-416040 [pii] 10.1182/blood-2012-03-416040 (2012).

Ye, J. et al. Tumor-derived gammadelta regulatory T cells suppress innate and adaptive immunity through the induction of immunosenescence. *Journal of immunology* 190, 2403-2414, doi: 10.4049/jimmunol. 1202369 (2013).

Ye, J. & Peng, G. Controlling T cell senescence in the tumor microenvironment for tumor immunotherapy. *Oncoimmunology* 4, e994398, doi: 10.4161/2162402X.2014.994398 (2015).

Meloni, F. et al. Foxp3 expressing CD4+CD25+ and CD8+CD28-T regulatory cells in the peripheral blood of patients with lung cancer and pleural mesothelioma. *Hum Immunol* 67, 1-12, doi: S0198-8859 (05) 00457-X [pii] 10.1016/j.humimm.2005.11.005 (2006).

Gruber, I. V. et al. Down-regulation of CD28, TCR-zeta (zeta) and up-regulation of FAS in peripheral cytotoxic T-cells of primary breast cancer patients. *Anticancer research* 28, 779-784 (2008).

Urbaniak-Kujda, D. et al. Increased percentage of CD8+CD28-suppressor lymphocytes in peripheral blood and skin infiltrates correlates with advanced disease in patients with cutaneous T-cell lymphomas. *Postepy higieny i medycyny doświadczalnej* 63, 355-359 (2009).

James, E. L. et al. Senescent human fibroblasts show increased glycolysis and redox homeostasis with extracellular metabolomes that overlap with those of irreparable DNA damage, aging, and disease. *Journal of proteome research* 14, 1854-1871, doi: 10.1021/pr501221g (2015).

Liao, E. C. et al. Radiation induces senescence and a bystander effect through metabolic alterations. *Cell death & disease* 5, e1255, doi: 10.1038/cddis.2014.220 (2014).

Takebayashi, S. et al. Retinoblastoma protein promotes oxidative phosphorylation through upregulation of glycolytic genes in oncogene-induced senescent cells. *Aging cell* 14, 689-697, doi: 10.1111/acel.12351 (2015).

Li, L. et al. TLR8-Mediated Metabolic Control of Human Treg Function: A Mechanistic Target for Cancer Immunotherapy. *Cell Metab* 29, 103-123 e105, doi: 10.1016/j.cmet.2018.09.020 (2019).

Shi, L. Z. et al. HIF 1 alpha-dependent glycolytic pathway orchestrates a metabolic checkpoint for the differentiation of TH17 and Treg cells. *The Journal of experimental medicine* 208, 1367-1376, doi: 10.1084/jem.20110278 (2011).

Pearce, E. L. et al. Enhancing CD8 T-cell memory by modulating fatty acid metabolism. *Nature* 460, 103-107, doi: 10.1038/nature08097 (2009).

Buck, M. D. et al. Mitochondrial Dynamics Controls T Cell Fate through Metabolic Programming. *Cell* 166, 63-76, doi: 10.1016/j.cell.2016.05.035 (2016).

Berod, L. et al. De novo fatty acid synthesis controls the fate between regulatory T and T helper 17 cells. *Nature medicine* 20, 1327-1333, doi: 10.1038/nm.3704 (2014).

Ford, J. H. Saturated fatty acid metabolism is key link between cell division, cancer, and senescence in cellular and whole organism aging. *Age (Dordr)* 32, 231-237, doi: 10.1007/s11357-009-9128-x (2010).

Han, X. & Gross, R. W. Shotgun lipidomics: electrospray ionization mass spectrometric analysis and quantitation of cellular lipidomes directly from crude extracts of biological samples. *Mass spectrometry reviews* 24, 367-412, doi: 10.1002/mas.20023 (2005).

Bowden, J. A. et al. Electrospray ionization tandem mass spectrometry of sodiated adducts of cholesteryl esters. *Lipids* 46, 1169-1179, doi: 10.1007/s11745-011-3609-2 (2011).

Yang, W. et al. Potentiating the antitumour response of CD8 (+) T cells by modulating cholesterol metabolism. *Nature* 531, 651-655, doi: 10.1038/nature17412 (2016).

Fujimoto, T. & Parton, R. G. Not just fat: the structure and function of the lipid droplet. *Cold Spring Harbor perspectives in biology* 3, doi: 10.1101/cshperspect.a004838 (2011).

Guijas, C., Rodriguez, J. P., Rubio, J. M., Balboa, M. A. & Balsinde, J. Phospholipase A$_2$ regulation of lipid droplet formation. *Biochimica et biophysica acta* 1841, 1661-1671, doi: 10.1016/j.bbalip.2014.10.004 (2014).

Spangenburg, E. E., Pratt, S. J. P., Wohlers, L. M. & Lovering, R. M. Use of BODIPY (493/503) to Visualize Intramuscular Lipid Droplets in Skeletal Muscle. *J Biomed Biotechnol, doi: Artn* 598358 10.1155/2011/598358 (2011).

Gubern, A. et al. Group IVA phospholipase A2 is necessary for the biogenesis of lipid droplets. *J Biol Chem* 283, 27369-27382, doi: 10.1074/jbc.M800696200 (2008).

Gubern, A. et al. Lipid droplet biogenesis induced by stress involves triacylglycerol synthesis that depends on group VIA phospholipase A2. *The Journal of biological chemistry* 284, 5697-5708, doi: 10.1074/jbc.M806173200 (2009).

Guijas, C. et al. Simultaneous activation of p38 and JNK by arachidonic acid stimulates the cytosolic phospholipase A$_2$-dependent synthesis of lipid droplets in human monocytes. *Journal of lipid research* 53, 2343-2354, doi: 10.1194/jlr.M028423 (2012).

Abad, J. D. et al. T-cell receptor gene therapy of established tumors in a murine melanoma model. *J Immunother* 31, 1-6, doi: 10.1097/CJI.0b013e31815c193f (2008).

Peng, G. et al. Toll-like receptor 8-mediated reversal of CD4+ regulatory T cell function. *Science* 309, 1380-1384, doi: 309/5739/1380 [pii] 10.1126/science. 1113401 (2005).

Peng, G. et al. Tumor-infiltrating gamma-delta T cells suppress T and dendritic cell function via mechanisms controlled by a unique toll-like receptor signaling pathway. *Immunity* 27, 334-348, doi: 10.1016/j.immuni.2007.05.020 (2007).

Lyssiotis, C. A. & Kimmelman, A. C. Metabolic Interactions in the Tumor Microenvironment. *Trends in cell biology* 27, 863-875, doi: 10.1016/j.tcb.2017.06.003 (2017).

Xia, H. et al. Suppression of FIP200 and autophagy by tumor-derived lactate promotes naive T cell apoptosis and affects tumor immunity. *Science immunology* 2, doi: 10.1126/sciimmunol.aan4631 (2017).

Sitkovsky, M. V., Kjaergaard, J., Lukashev, D. & Ohta, A. Hypoxia-adenosinergic immunosuppression: tumor protection by T regulatory cells and cancerous tissue hypoxia. *Clin Cancer Res* 14, 5947-5952, doi: 14/19/5947 [pii] 10.1158/1078-0432.CCR-08-0229 (2008).

Penno, A., Hackenbroich, G. & Thiele, C. Phospholipids and lipid droplets. *Biochimica et biophysica acta* 1831, 589-594, doi: 10.1016/j.bbalip.2012.12.001 (2013).

Wiley, C. D. & Campisi, J. From Ancient Pathways to Aging Cells-Connecting Metabolism and Cellular Senescence. *Cell Metab* 23, 1013-1021, doi: 10.1016/j.cmet.2016.05.010 (2016).

Lizardo, D. Y., Lin, Y. L., Gokcumen, O. & Atilla-Gokcumen, G. E. Regulation of lipids is central to replicative senescence. *Molecular bioSystems* 13, 498-509, doi: 10.1039/c6mb00842a (2017).

Lanna, A., Henson, S. M., Escors, D. & Akbar, A. N. The kinase p38 activated by the metabolic regulator AMPK and scaffold TAB1 drives the senescence of human T cells. *Nature immunology* 15, 965—U211, doi: 10.1038/ni.2981 (2014).

Lanna, A. et al. A sestrin-dependent Erk-Jnk-p38 MAPK activation complex inhibits immunity during aging. *Nature immunology* 18, 354-363, doi: 10.1038/ni.3665 (2017).

Perez-Chacon, G., Astudillo, A. M., Balgoma, D., Balboa, M. A. & Balsinde, J. Control of free arachidonic acid levels by phospholipases A2 and lysophospholipid acyltransferases. *Biochimica et biophysica acta* 1791, 1103-1113, doi: 10.1016/j.bbalip.2009.08.007 (2009).

Bligh, E. G. & Dyer, W. J. A rapid method of total lipid extraction and purification. *Canadian journal of biochemistry and physiology* 37, 911-917, doi: 10.1139/059-099 (1959).

Quehenberger, O. et al. Lipidomics reveals a remarkable diversity of lipids in human plasma. *Journal of lipid research* 51, 3299-3305, doi: 10.1194/jlr. M009449 (2010).

Peng, W. et al. Transduction of tumor-specific T cells with CXCR2 chemokine receptor improves migration to tumor and antitumor immune responses. *Clin Cancer Res* 16, 5458-5468, doi: 10.1158/1078-0432.CCR-10-0712 (2010).

What is claimed:

1. A method of inhibiting induction of senescence in a cell comprising contacting said cell with an inhibitor of group IVA phosopholipase $A_2$, wherein the inhibitor is not KU55933, and wherein:
  (a) the cell is contacted ex vivo and administered to a subject; or
  (b) the cell is located in a subject.

2. The method of claim 1, wherein said cell is a T cell.

3. The method of claim 2, wherein said T cell is a CD4+ T cell or a CD8+ T cell.

4. The method of claim 1, wherein said inhibitor of group IVA phosopholipase $A_2$ is contacted with said cell more than once.

5. The method of claim 1, wherein said cell is located in a subject.

6. The method of claim 5, wherein the inhibitor of group IVA phosopholipase $A_2$ is delivered systemically.

7. The method of claim 5, wherein the cell is located in a tumor microenvironment.

8. The method of claim 7, wherein the inhibitor or group IVA phosopholipase $A_2$ is delivered to the tumor microenvironment.

9. The method of claim 1, wherein said cell is contacted ex vivo and then administered to a subject.

10. The method of claim 9, wherein the cell was originally obtained from said subject prior to contacting with the inhibitor of group IVA phosopholipase $A_2$.

11. The method of claim 1, wherein said inhibitor of group IVA phosopholipase $A_2$ is a pharmacologic inhibitor of group IVA phosopholipase $A_2$.

12. The method of claim 1, wherein said inhibitor of group IVA phosopholipase $A_2$ is an inhibitory oligonucleotide.

13. The method of claim 12, wherein said inhibitory oligonucleotide is a ribozyme, an antisense oligonucleotide, an shRNA, an siRNA or a CRISPR-Cas9 gRNA.

* * * * *

SEQUENCE LISTING

<160> NUMBER OF SEQ ID NOS: 108

<210> SEQ ID NO 1
<211> LENGTH: 21
<212> TYPE: DNA
<213> ORGANISM: Artificial sequence
<220> FEATURE:
<223> OTHER INFORMATION: Synthetic primer

<400> SEQUENCE: 1
acagatgaag tgctccttcc a                21

<210> SEQ ID NO 2
<211> LENGTH: 21
<212> TYPE: DNA
<213> ORGANISM: Artificial sequence
<220> FEATURE:
<223> OTHER INFORMATION: Synthetic primer

<400> SEQUENCE: 2
gtcggagatt cgtagctgga t                                          21

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
gtcacaaaca gtgcacctac                                            20

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
ccctgggtct taagtgaaag                                            20

<210> SEQ ID NO 5
<211> LENGTH: 18
<212> TYPE: DNA
<213> ORGANISM: Artificial sequence
<220> FEATURE:
<223> OTHER INFORMATION: Synthetic primer

<400> SEQUENCE: 5
gtagccgccc cacacaga                                              18

<210> SEQ ID NO 6
<211> LENGTH: 21
<212> TYPE: DNA
<213> ORGANISM: Artificial sequence
<220> FEATURE:
<223> OTHER INFORMATION: Synthetic primer

<400> SEQUENCE: 6
catgtctcct ttctcagggc t                                          21

<210> SEQ ID NO 7
<211> LENGTH: 27
<212> TYPE: DNA
<213> ORGANISM: Artificial sequence
<220> FEATURE:
<223> OTHER INFORMATION: Synthetic primer

<400> SEQUENCE: 7
ataaagacat actccaaacc tttccac                                    27

<210> SEQ ID NO 8
<211> LENGTH: 27
<212> TYPE: DNA
<213> ORGANISM: Artificial sequence
<220> FEATURE:

-continued

<223> OTHER INFORMATION: Synthetic primer

<400> SEQUENCE: 8
aagctttaca ataatttctg tgttggc                                    27

<210> SEQ ID NO 9
<211> LENGTH: 20
<212> TYPE: DNA
<213> ORGANISM: Artificial sequence
<220> FEATURE:
<223> OTHER INFORMATION: Synthetic primer

<400> SEQUENCE: 9
ggagaagggt gaccgactca                                            20

<210> SEQ ID NO 10
<211> LENGTH: 17
<212> TYPE: DNA
<213> ORGANISM: Artificial sequence
<220> FEATURE:
<223> OTHER INFORMATION: Synthetic primer

<400> SEQUENCE: 10
ctgcccagac tcggcaa                                               17

<210> SEQ ID NO 11
<211> LENGTH: 19
<212> TYPE: DNA
<213> ORGANISM: Artificial sequence
<220> FEATURE:
<223> OTHER INFORMATION: Synthetic primer

<400> SEQUENCE: 11
aagagtgtgg agaccatca                                             19

<210> SEQ ID NO 12
<211> LENGTH: 20
<212> TYPE: DNA
<213> ORGANISM: Artificial sequence
<220> FEATURE:
<223> OTHER INFORMATION: Synthetic primer

<400> SEQUENCE: 12
tgctcttcga ccttgaaaca                                            20

<210> SEQ ID NO 13
<211> LENGTH: 21
<212> TYPE: DNA
<213> ORGANISM: Artificial sequence
<220> FEATURE:
<223> OTHER INFORMATION: Synthetic primer

<400> SEQUENCE: 13
attggctccg gtatcgtcaa c                                          21

<210> SEQ ID NO 14
<211> LENGTH: 23
<212> TYPE: DNA
<213> ORGANISM: Artificial sequence
<220> FEATURE:
<223> OTHER INFORMATION: Synthetic primer

<400> SEQUENCE: 14
gctcagatag gacatccagg gta                                        23

-continued

```
<210> SEQ ID NO 15
<211> LENGTH: 23
<212> TYPE: DNA
<213> ORGANISM: Artificial sequence
<220> FEATURE:
<223> OTHER INFORMATION: Synthetic primer

<400> SEQUENCE: 15
gctctctggg atcaatgctg tgt                                             23

<210> SEQ ID NO 16
<211> LENGTH: 21
<212> TYPE: DNA
<213> ORGANISM: Artificial sequence
<220> FEATURE:
<223> OTHER INFORMATION: Synthetic primer

<400> SEQUENCE: 16
cttcctgccc tttccaccag a                                               21

<210> SEQ ID NO 17
<211> LENGTH: 20
<212> TYPE: DNA
<213> ORGANISM: Artificial sequence
<220> FEATURE:
<223> OTHER INFORMATION: Synthetic primer

<400> SEQUENCE: 17
aacagcctgg acgagagcat                                                 20

<210> SEQ ID NO 18
<211> LENGTH: 20
<212> TYPE: DNA
<213> ORGANISM: Artificial sequence
<220> FEATURE:
<223> OTHER INFORMATION: Synthetic primer

<400> SEQUENCE: 18
gccaacaatg aggccaactt                                                 20

<210> SEQ ID NO 19
<211> LENGTH: 20
<212> TYPE: DNA
<213> ORGANISM: Artificial sequence
<220> FEATURE:
<223> OTHER INFORMATION: Synthetic primer

<400> SEQUENCE: 19
gatggtagct ctctgcagcc                                                 20

<210> SEQ ID NO 20
<211> LENGTH: 18
<212> TYPE: DNA
<213> ORGANISM: Artificial sequence
<220> FEATURE:
<223> OTHER INFORMATION: Synthetic primer

<400> SEQUENCE: 20
gccatggcgg gactcttg                                                   18

<210> SEQ ID NO 21
<211> LENGTH: 20
<212> TYPE: DNA
<213> ORGANISM: Artificial sequence
<220> FEATURE:
<223> OTHER INFORMATION: Synthetic primer
```

-continued

```
<400> SEQUENCE: 21
ggcagccatg cataaagacg                                                    20

<210> SEQ ID NO 22
<211> LENGTH: 20
<212> TYPE: DNA
<213> ORGANISM: Artificial sequence
<220> FEATURE:
<223> OTHER INFORMATION: Synthetic primer

<400> SEQUENCE: 22
aagcttcccc agctgttctc                                                    20

<210> SEQ ID NO 23
<211> LENGTH: 20
<212> TYPE: DNA
<213> ORGANISM: Artificial sequence
<220> FEATURE:
<223> OTHER INFORMATION: Synthetic primer

<400> SEQUENCE: 23
aggcatgtct ttggggagtc                                                    20

<210> SEQ ID NO 24
<211> LENGTH: 21
<212> TYPE: DNA
<213> ORGANISM: Artificial sequence
<220> FEATURE:
<223> OTHER INFORMATION: Synthetic primer

<400> SEQUENCE: 24
agtccttcac gttatctgcg a                                                  21

<210> SEQ ID NO 25
<211> LENGTH: 20
<212> TYPE: DNA
<213> ORGANISM: Artificial sequence
<220> FEATURE:
<223> OTHER INFORMATION: Synthetic primer

<400> SEQUENCE: 25
cgccttagct aggcaggaag                                                    20

<210> SEQ ID NO 26
<211> LENGTH: 21
<212> TYPE: DNA
<213> ORGANISM: Artificial sequence
<220> FEATURE:
<223> OTHER INFORMATION: Synthetic primer

<400> SEQUENCE: 26
ggtgaacttc tagccactgg g                                                  21

<210> SEQ ID NO 27
<211> LENGTH: 20
<212> TYPE: DNA
<213> ORGANISM: Artificial sequence
<220> FEATURE:
<223> OTHER INFORMATION: Synthetic primer

<400> SEQUENCE: 27
acgagaacat cctgtggctg                                                    20

<210> SEQ ID NO 28
<211> LENGTH: 20
```

-continued

```
<212> TYPE: DNA
<213> ORGANISM: Artificial sequence
<220> FEATURE:
<223> OTHER INFORMATION: Synthetic primer

<400> SEQUENCE: 28
aggaagtcgg cacctttctg                                            20

<210> SEQ ID NO 29
<211> LENGTH: 20
<212> TYPE: DNA
<213> ORGANISM: Artificial sequence
<220> FEATURE:
<223> OTHER INFORMATION: Synthetic primer

<400> SEQUENCE: 29
agctgttcca cttaaggccc                                            20

<210> SEQ ID NO 30
<211> LENGTH: 21
<212> TYPE: DNA
<213> ORGANISM: Artificial sequence
<220> FEATURE:
<223> OTHER INFORMATION: Synthetic primer

<400> SEQUENCE: 30
tggaaccaaa aggaatcggg a                                          21

<210> SEQ ID NO 31
<211> LENGTH: 22
<212> TYPE: DNA
<213> ORGANISM: Artificial sequence
<220> FEATURE:
<223> OTHER INFORMATION: Synthetic primer

<400> SEQUENCE: 31
atcaatcgga ctctggaaac gg                                         22

<210> SEQ ID NO 32
<211> LENGTH: 19
<212> TYPE: DNA
<213> ORGANISM: Artificial sequence
<220> FEATURE:
<223> OTHER INFORMATION: Synthetic primer

<400> SEQUENCE: 32
tcagggagta gcgcatggt                                             19

<210> SEQ ID NO 33
<211> LENGTH: 23
<212> TYPE: DNA
<213> ORGANISM: Artificial sequence
<220> FEATURE:
<223> OTHER INFORMATION: Synthetic primer

<400> SEQUENCE: 33
tcacacctga agaccttaaa gcc                                        23

<210> SEQ ID NO 34
<211> LENGTH: 20
<212> TYPE: DNA
<213> ORGANISM: Artificial sequence
<220> FEATURE:
<223> OTHER INFORMATION: Synthetic primer

<400> SEQUENCE: 34
```

-continued

```
agcccacact gcttgtactg                                          20

<210> SEQ ID NO 35
<211> LENGTH: 19
<212> TYPE: DNA
<213> ORGANISM: Artificial sequence
<220> FEATURE:
<223> OTHER INFORMATION: Synthetic primer

<400> SEQUENCE: 35
acagcgggga atgggtact                                           19

<210> SEQ ID NO 36
<211> LENGTH: 20
<212> TYPE: DNA
<213> ORGANISM: Artificial sequence
<220> FEATURE:
<223> OTHER INFORMATION: Synthetic primer

<400> SEQUENCE: 36
gactggtaca acgagcggat                                          20

<210> SEQ ID NO 37
<211> LENGTH: 22
<212> TYPE: DNA
<213> ORGANISM: Artificial sequence
<220> FEATURE:
<223> OTHER INFORMATION: Synthetic primer

<400> SEQUENCE: 37
gtgagatctg gaggatccaa gg                                       22

<210> SEQ ID NO 38
<211> LENGTH: 20
<212> TYPE: DNA
<213> ORGANISM: Artificial sequence
<220> FEATURE:
<223> OTHER INFORMATION: Synthetic primer

<400> SEQUENCE: 38
gatgggaggc cacaaagagg                                          20

<210> SEQ ID NO 39
<211> LENGTH: 21
<212> TYPE: DNA
<213> ORGANISM: Artificial sequence
<220> FEATURE:
<223> OTHER INFORMATION: Synthetic primer

<400> SEQUENCE: 39
gttggcggct ataaagctgg t                                        21

<210> SEQ ID NO 40
<211> LENGTH: 16
<212> TYPE: DNA
<213> ORGANISM: Artificial sequence
<220> FEATURE:
<223> OTHER INFORMATION: Synthetic primer

<400> SEQUENCE: 40
ccttcgggca caagcg                                              16

<210> SEQ ID NO 41
<211> LENGTH: 23
<212> TYPE: DNA
<213> ORGANISM: Artificial sequence
```

-continued

```
<220> FEATURE:
<223> OTHER INFORMATION: Synthetic primer

<400> SEQUENCE: 41
tgacaattct catctgaggt cca                                        23

<210> SEQ ID NO 42
<211> LENGTH: 22
<212> TYPE: DNA
<213> ORGANISM: Artificial sequence
<220> FEATURE:
<223> OTHER INFORMATION: Synthetic primer

<400> SEQUENCE: 42
tcccaaaaga agaacacctc gt                                         22

<210> SEQ ID NO 43
<211> LENGTH: 21
<212> TYPE: DNA
<213> ORGANISM: Artificial sequence
<220> FEATURE:
<223> OTHER INFORMATION: Synthetic primer

<400> SEQUENCE: 43
cggaggctga tcagtgttct a                                          21

<210> SEQ ID NO 44
<211> LENGTH: 20
<212> TYPE: DNA
<213> ORGANISM: Artificial sequence
<220> FEATURE:
<223> OTHER INFORMATION: Synthetic primer

<400> SEQUENCE: 44
tgttgcttgt cgaggtggtt                                            20

<210> SEQ ID NO 45
<211> LENGTH: 22
<212> TYPE: DNA
<213> ORGANISM: Artificial sequence
<220> FEATURE:
<223> OTHER INFORMATION: Synthetic primer

<400> SEQUENCE: 45
taccagaagt aaagcagcat gg                                         22

<210> SEQ ID NO 46
<211> LENGTH: 22
<212> TYPE: DNA
<213> ORGANISM: Artificial sequence
<220> FEATURE:
<223> OTHER INFORMATION: Synthetic primer

<400> SEQUENCE: 46
tcattcagtg tactggcatt gg                                         22

<210> SEQ ID NO 47
<211> LENGTH: 21
<212> TYPE: DNA
<213> ORGANISM: Artificial sequence
<220> FEATURE:
<223> OTHER INFORMATION: Synthetic primer

<400> SEQUENCE: 47
gcggaccatc ataggttcct t                                          21
```

-continued

```
<210> SEQ ID NO 48
<211> LENGTH: 23
<212> TYPE: DNA
<213> ORGANISM: Artificial sequence
<220> FEATURE:
<223> OTHER INFORMATION: Synthetic primer

<400> SEQUENCE: 48
actggcttgt ctaacaggat tct                                           23

<210> SEQ ID NO 49
<211> LENGTH: 20
<212> TYPE: DNA
<213> ORGANISM: Artificial sequence
<220> FEATURE:
<223> OTHER INFORMATION: Synthetic primer

<400> SEQUENCE: 49
cccacgtttg cactcatgtc                                               20

<210> SEQ ID NO 50
<211> LENGTH: 22
<212> TYPE: DNA
<213> ORGANISM: Artificial sequence
<220> FEATURE:
<223> OTHER INFORMATION: Synthetic primer

<400> SEQUENCE: 50
cccagtcaaa ggcttgaaac tt                                            22

<210> SEQ ID NO 51
<211> LENGTH: 23
<212> TYPE: DNA
<213> ORGANISM: Artificial sequence
<220> FEATURE:
<223> OTHER INFORMATION: Synthetic primer

<400> SEQUENCE: 51
aatactgcac aatgcccttt acc                                           23

<210> SEQ ID NO 52
<211> LENGTH: 21
<212> TYPE: DNA
<213> ORGANISM: Artificial sequence
<220> FEATURE:
<223> OTHER INFORMATION: Synthetic primer

<400> SEQUENCE: 52
gcttccaaat aagtcgggag c                                             21

<210> SEQ ID NO 53
<211> LENGTH: 19
<212> TYPE: DNA
<213> ORGANISM: Artificial sequence
<220> FEATURE:
<223> OTHER INFORMATION: Synthetic primer

<400> SEQUENCE: 53
tggcacccag cacaatgaa                                                19

<210> SEQ ID NO 54
<211> LENGTH: 25
<212> TYPE: DNA
<213> ORGANISM: Artificial sequence
<220> FEATURE:
<223> OTHER INFORMATION: Synthetic primer
```

<400> SEQUENCE: 54
ctaagtcata gtccgcctag aagca                                          25

<210> SEQ ID NO 55
<211> LENGTH: 22
<212> TYPE: DNA
<213> ORGANISM: Artificial sequence
<220> FEATURE:
<223> OTHER INFORMATION: Synthetic primer

<400> SEQUENCE: 55
agccgcatct tcttttgcgt cg                                             22

<210> SEQ ID NO 56
<211> LENGTH: 18
<212> TYPE: DNA
<213> ORGANISM: Artificial sequence
<220> FEATURE:
<223> OTHER INFORMATION: Synthetic primer

<400> SEQUENCE: 56
gaccaggcgc ccaatacg                                                  18

<210> SEQ ID NO 57
<211> LENGTH: 20
<212> TYPE: DNA
<213> ORGANISM: Artificial sequence
<220> FEATURE:
<223> OTHER INFORMATION: Synthetic primer

<400> SEQUENCE: 57
gggcctcaca ggaaagaatc                                                20

<210> SEQ ID NO 58
<211> LENGTH: 20
<212> TYPE: DNA
<213> ORGANISM: Artificial sequence
<220> FEATURE:
<223> OTHER INFORMATION: Synthetic primer

<400> SEQUENCE: 58
ggggaactct gcagactcaa                                                20

<210> SEQ ID NO 59
<211> LENGTH: 19
<212> TYPE: DNA
<213> ORGANISM: Artificial sequence
<220> FEATURE:
<223> OTHER INFORMATION: Synthetic primer

<400> SEQUENCE: 59
tccagaacat gccgcagag                                                 19

<210> SEQ ID NO 60
<211> LENGTH: 23
<212> TYPE: DNA
<213> ORGANISM: Artificial sequence
<220> FEATURE:
<223> OTHER INFORMATION: Synthetic primer

<400> SEQUENCE: 60
cctgagcagg atggagaatt aca                                            23

<210> SEQ ID NO 61

```
<211> LENGTH: 20
<212> TYPE: DNA
<213> ORGANISM: Artificial sequence
<220> FEATURE:
<223> OTHER INFORMATION: Synthetic primer

<400> SEQUENCE: 61
gttctctggg aaatcgtgga                                                    20

<210> SEQ ID NO 62
<211> LENGTH: 20
<212> TYPE: DNA
<213> ORGANISM: Artificial sequence
<220> FEATURE:
<223> OTHER INFORMATION: Synthetic primer

<400> SEQUENCE: 62
tgtactccag gtagctatgg                                                    20

<210> SEQ ID NO 63
<211> LENGTH: 20
<212> TYPE: DNA
<213> ORGANISM: Artificial sequence
<220> FEATURE:
<223> OTHER INFORMATION: Synthetic primer

<400> SEQUENCE: 63
accctcacac tcagatcatc                                                    20

<210> SEQ ID NO 64
<211> LENGTH: 20
<212> TYPE: DNA
<213> ORGANISM: Artificial sequence
<220> FEATURE:
<223> OTHER INFORMATION: Synthetic primer

<400> SEQUENCE: 64
gagtagacaa ggtacaaccc                                                    20

<210> SEQ ID NO 65
<211> LENGTH: 21
<212> TYPE: DNA
<213> ORGANISM: Artificial sequence
<220> FEATURE:
<223> OTHER INFORMATION: Synthetic primer

<400> SEQUENCE: 65
atgaacgcta cacactgcat c                                                  21

<210> SEQ ID NO 66
<211> LENGTH: 21
<212> TYPE: DNA
<213> ORGANISM: Artificial sequence
<220> FEATURE:
<223> OTHER INFORMATION: Synthetic primer

<400> SEQUENCE: 66
ccatcctttt gccagttcct c                                                  21

<210> SEQ ID NO 67
<211> LENGTH: 22
<212> TYPE: DNA
<213> ORGANISM: Artificial sequence
<220> FEATURE:
<223> OTHER INFORMATION: Synthetic primer

<400> SEQUENCE: 67
```
cagttcggct ataacactgg tg                                                    22

<210> SEQ ID NO 68
<211> LENGTH: 19
<212> TYPE: DNA
<213> ORGANISM: Artificial sequence
<220> FEATURE:
<223> OTHER INFORMATION: Synthetic primer

<400> SEQUENCE: 68
gcccccgaca gagaagatg                                                        19

<210> SEQ ID NO 69
<211> LENGTH: 21
<212> TYPE: DNA
<213> ORGANISM: Artificial sequence
<220> FEATURE:
<223> OTHER INFORMATION: Synthetic primer

<400> SEQUENCE: 69
ctttggcaga cgcaactcta t                                                     21

<210> SEQ ID NO 70
<211> LENGTH: 21
<212> TYPE: DNA
<213> ORGANISM: Artificial sequence
<220> FEATURE:
<223> OTHER INFORMATION: Synthetic primer

<400> SEQUENCE: 70
accagaatcc caacaacgat g                                                     21

<210> SEQ ID NO 71
<211> LENGTH: 21
<212> TYPE: DNA
<213> ORGANISM: Artificial sequence
<220> FEATURE:
<223> OTHER INFORMATION: Synthetic primer

<400> SEQUENCE: 71
tgatcgcctg cttattcacg g                                                     21

<210> SEQ ID NO 72
<211> LENGTH: 21
<212> TYPE: DNA
<213> ORGANISM: Artificial sequence
<220> FEATURE:
<223> OTHER INFORMATION: Synthetic primer

<400> SEQUENCE: 72
aaccgcctag aaatctccag a                                                     21

<210> SEQ ID NO 73
<211> LENGTH: 21
<212> TYPE: DNA
<213> ORGANISM: Artificial sequence
<220> FEATURE:
<223> OTHER INFORMATION: Synthetic primer

<400> SEQUENCE: 73
tcccctgaga cttccctctt t                                                     21

<210> SEQ ID NO 74
<211> LENGTH: 21
<212> TYPE: DNA

-continued

```
<213> ORGANISM: Artificial sequence
<220> FEATURE:
<223> OTHER INFORMATION: Synthetic primer

<400> SEQUENCE: 74
cgagaaacca ctcctttgct g                                          21

<210> SEQ ID NO 75
<211> LENGTH: 21
<212> TYPE: DNA
<213> ORGANISM: Artificial sequence
<220> FEATURE:
<223> OTHER INFORMATION: Synthetic primer

<400> SEQUENCE: 75
tgtggtccga gttggtatct t                                          21

<210> SEQ ID NO 76
<211> LENGTH: 20
<212> TYPE: DNA
<213> ORGANISM: Artificial sequence
<220> FEATURE:
<223> OTHER INFORMATION: Synthetic primer

<400> SEQUENCE: 76
gcacttccaa tcactgtgcc                                            20

<210> SEQ ID NO 77
<211> LENGTH: 21
<212> TYPE: DNA
<213> ORGANISM: Artificial sequence
<220> FEATURE:
<223> OTHER INFORMATION: Synthetic primer

<400> SEQUENCE: 77
ccaggaagtt cttcgttggg g                                          21

<210> SEQ ID NO 78
<211> LENGTH: 21
<212> TYPE: DNA
<213> ORGANISM: Artificial sequence
<220> FEATURE:
<223> OTHER INFORMATION: Synthetic primer

<400> SEQUENCE: 78
caaagtcgat gtaagcggtg g                                          21

<210> SEQ ID NO 79
<211> LENGTH: 19
<212> TYPE: DNA
<213> ORGANISM: Artificial sequence
<220> FEATURE:
<223> OTHER INFORMATION: Synthetic primer

<400> SEQUENCE: 79
agagtgggag gcgcttagt                                             19

<210> SEQ ID NO 80
<211> LENGTH: 21
<212> TYPE: DNA
<213> ORGANISM: Artificial sequence
<220> FEATURE:
<223> OTHER INFORMATION: Synthetic primer

<400> SEQUENCE: 80
atggcgaatt tctggcagta g                                          21
```

-continued

```
<210> SEQ ID NO 81
<211> LENGTH: 21
<212> TYPE: DNA
<213> ORGANISM: Artificial sequence
<220> FEATURE:
<223> OTHER INFORMATION: Synthetic primer

<400> SEQUENCE: 81
gtggctcggc tgaatttctc t                                         21

<210> SEQ ID NO 82
<211> LENGTH: 19
<212> TYPE: DNA
<213> ORGANISM: Artificial sequence
<220> FEATURE:
<223> OTHER INFORMATION: Synthetic primer

<400> SEQUENCE: 82
caccgcaaca ggacggtag                                            19

<210> SEQ ID NO 83
<211> LENGTH: 22
<212> TYPE: DNA
<213> ORGANISM: Artificial sequence
<220> FEATURE:
<223> OTHER INFORMATION: Synthetic primer

<400> SEQUENCE: 83
tgtctccagc aaagactact gt                                        22

<210> SEQ ID NO 84
<211> LENGTH: 23
<212> TYPE: DNA
<213> ORGANISM: Artificial sequence
<220> FEATURE:
<223> OTHER INFORMATION: Synthetic primer

<400> SEQUENCE: 84
gactgtactt gacaatgttg gga                                       23

<210> SEQ ID NO 85
<211> LENGTH: 22
<212> TYPE: DNA
<213> ORGANISM: Artificial sequence
<220> FEATURE:
<223> OTHER INFORMATION: Synthetic primer

<400> SEQUENCE: 85
tcttgtggaa tgccttgtga tt                                        22

<210> SEQ ID NO 86
<211> LENGTH: 21
<212> TYPE: DNA
<213> ORGANISM: Artificial sequence
<220> FEATURE:
<223> OTHER INFORMATION: Synthetic primer

<400> SEQUENCE: 86
gggttacggg gtttggttta t                                         21

<210> SEQ ID NO 87
<211> LENGTH: 22
<212> TYPE: DNA
<213> ORGANISM: Artificial sequence
<220> FEATURE:
```

-continued

<223> OTHER INFORMATION: Synthetic primer

<400> SEQUENCE: 87
aactggtgca gaaatctcta gc                                                    22

<210> SEQ ID NO 88
<211> LENGTH: 23
<212> TYPE: DNA
<213> ORGANISM: Artificial sequence
<220> FEATURE:
<223> OTHER INFORMATION: Synthetic primer

<400> SEQUENCE: 88
ggttgaatag ctcagaacta gcc                                                   23

<210> SEQ ID NO 89
<211> LENGTH: 20
<212> TYPE: DNA
<213> ORGANISM: Artificial sequence
<220> FEATURE:
<223> OTHER INFORMATION: Synthetic primer

<400> SEQUENCE: 89
gctgggcctt ggagatacag                                                       20

<210> SEQ ID NO 90
<211> LENGTH: 22
<212> TYPE: DNA
<213> ORGANISM: Artificial sequence
<220> FEATURE:
<223> OTHER INFORMATION: Synthetic primer

<400> SEQUENCE: 90
cagtgggtac ggaatttgaa ct                                                    22

<210> SEQ ID NO 91
<211> LENGTH: 20
<212> TYPE: DNA
<213> ORGANISM: Artificial sequence
<220> FEATURE:
<223> OTHER INFORMATION: Synthetic primer

<400> SEQUENCE: 91
cgaaccctcc tcaagaagcc                                                       20

<210> SEQ ID NO 92
<211> LENGTH: 22
<212> TYPE: DNA
<213> ORGANISM: Artificial sequence
<220> FEATURE:
<223> OTHER INFORMATION: Synthetic primer

<400> SEQUENCE: 92
cctagaacac agagattccg gc                                                    22

<210> SEQ ID NO 93
<211> LENGTH: 22
<212> TYPE: DNA
<213> ORGANISM: Artificial sequence
<220> FEATURE:
<223> OTHER INFORMATION: Synthetic primer

<400> SEQUENCE: 93
agatcaatcg gaccctagac ac                                                    22

```
<210> SEQ ID NO 94
<211> LENGTH: 20
<212> TYPE: DNA
<213> ORGANISM: Artificial sequence
<220> FEATURE:
<223> OTHER INFORMATION: Synthetic primer

<400> SEQUENCE: 94
cagcgagtag cgcatagtca                                                          20

<210> SEQ ID NO 95
<211> LENGTH: 22
<212> TYPE: DNA
<213> ORGANISM: Artificial sequence
<220> FEATURE:
<223> OTHER INFORMATION: Synthetic primer

<400> SEQUENCE: 95
aatgaacgtg caatccgatt tg                                                       22

<210> SEQ ID NO 96
<211> LENGTH: 23
<212> TYPE: DNA
<213> ORGANISM: Artificial sequence
<220> FEATURE:
<223> OTHER INFORMATION: Synthetic primer

<400> SEQUENCE: 96
actccacatt tgcgtaattg ttg                                                      23

<210> SEQ ID NO 97
<211> LENGTH: 21
<212> TYPE: DNA
<213> ORGANISM: Artificial sequence
<220> FEATURE:
<223> OTHER INFORMATION: Synthetic primer

<400> SEQUENCE: 97
ggctctatgg attacccaag c                                                        21

<210> SEQ ID NO 98
<211> LENGTH: 19
<212> TYPE: DNA
<213> ORGANISM: Artificial sequence
<220> FEATURE:
<223> OTHER INFORMATION: Synthetic primer

<400> SEQUENCE: 98
ccagtgttcg ttcctcgga                                                           19

<210> SEQ ID NO 99
<211> LENGTH: 20
<212> TYPE: DNA
<213> ORGANISM: Artificial sequence
<220> FEATURE:
<223> OTHER INFORMATION: Synthetic primer

<400> SEQUENCE: 99
caacactggg cgcaggttta                                                          20

<210> SEQ ID NO 100
<211> LENGTH: 23
<212> TYPE: DNA
<213> ORGANISM: Artificial sequence
<220> FEATURE:
<223> OTHER INFORMATION: Synthetic primer
```

<400> SEQUENCE: 100
gcccgtcttt tacaatcagg tct                                                                    23

<210> SEQ ID NO 101
<211> LENGTH: 20
<212> TYPE: DNA
<213> ORGANISM: Artificial sequence
<220> FEATURE:
<223> OTHER INFORMATION: Synthetic primer

<400> SEQUENCE: 101
cccaggacaa ggttgcagtt                                                                        20

<210> SEQ ID NO 102
<211> LENGTH: 21
<212> TYPE: DNA
<213> ORGANISM: Artificial sequence
<220> FEATURE:
<223> OTHER INFORMATION: Synthetic primer

<400> SEQUENCE: 102
cgttcattcc tgatgcgttc g                                                                      21

<210> SEQ ID NO 103
<211> LENGTH: 23
<212> TYPE: DNA
<213> ORGANISM: Artificial sequence
<220> FEATURE:
<223> OTHER INFORMATION: Synthetic primer

<400> SEQUENCE: 103
cagcacatta tagtggaaca cca                                                                    23

<210> SEQ ID NO 104
<211> LENGTH: 21
<212> TYPE: DNA
<213> ORGANISM: Artificial sequence
<220> FEATURE:
<223> OTHER INFORMATION: Synthetic primer

<400> SEQUENCE: 104
agtgtccagc atatcgccaa a                                                                      21

<210> SEQ ID NO 105
<211> LENGTH: 23
<212> TYPE: DNA
<213> ORGANISM: Artificial sequence
<220> FEATURE:
<223> OTHER INFORMATION: Synthetic primer

<400> SEQUENCE: 105
gatcaagatc attgctcctc ctg                                                                    23

<210> SEQ ID NO 106
<211> LENGTH: 20
<212> TYPE: DNA
<213> ORGANISM: Artificial sequence
<220> FEATURE:
<223> OTHER INFORMATION: Synthetic primer

<400> SEQUENCE: 106
agggtgtaaa acgcagctca                                                                        20

<210> SEQ ID NO 107
<211> LENGTH: 23

-continued

```
<212> TYPE: DNA
<213> ORGANISM: Artificial sequence
<220> FEATURE:
<223> OTHER INFORMATION: Synthetic primer

<400> SEQUENCE: 107
gggttcctat aaatacggac tgc                                                        23

<210> SEQ ID NO 108
<211> LENGTH: 20
<212> TYPE: DNA
<213> ORGANISM: Artificial sequence
<220> FEATURE:
<223> OTHER INFORMATION: Synthetic primer

<400> SEQUENCE: 108
atgaaggggt cgttgatggc                                                            20
```